United States Patent
Andrews et al.

(10) Patent No.: US 11,883,471 B2
(45) Date of Patent: *Jan. 30, 2024

(54) ENHANCING HEALTH IN MAMMALS USING TELOMERASE REVERSE TRANSCRIPTASE GENE THERAPY

(71) Applicant: Sierra Sciences, LLC, Reno, NV (US)

(72) Inventors: William H. Andrews, Reno, NV (US); Lancer K. Brown, Sparks, NV (US); Hamid Mohammadpour, Reno, NV (US); Laura A. Briggs, Reno, NV (US)

(73) Assignee: Sierra Sciences, LLC, Reno, NV (US)

( * ) Notice: Subject to any disclaimer, the term of this patent is extended or adjusted under 35 U.S.C. 154(b) by 163 days.

This patent is subject to a terminal disclaimer.

(21) Appl. No.: 17/331,178

(22) Filed: May 26, 2021

(65) Prior Publication Data

US 2021/0361751 A1 Nov. 25, 2021

Related U.S. Application Data

(63) Continuation of application No. 16/803,006, filed on Feb. 27, 2020, now Pat. No. 11,052,134, which is a continuation of application No. 15/220,250, filed on Jul. 26, 2016, now Pat. No. 10,610,574, which is a continuation of application No. 14/655,140, filed as application No. PCT/US2013/077619 on Dec. 23, 2013, now Pat. No. 9,453,209.

(60) Provisional application No. 61/746,438, filed on Dec. 27, 2012.

(51) Int. Cl.
| | |
|---|---|
| *C07H 21/04* | (2006.01) |
| *A61K 38/45* | (2006.01) |
| *C12N 9/12* | (2006.01) |
| *C12N 7/00* | (2006.01) |
| *A61K 48/00* | (2006.01) |
| *A61K 38/00* | (2006.01) |

(52) U.S. Cl.
CPC ............... *A61K 38/45* (2013.01); *A61K 48/00* (2013.01); *A61K 48/005* (2013.01); *A61K 48/0066* (2013.01); *C12N 7/00* (2013.01); *C12N 9/1276* (2013.01); *C12Y 207/07049* (2013.01); *A61K 38/00* (2013.01); *C12N 2710/10341* (2013.01); *C12N 2740/15041* (2013.01); *C12N 2750/14143* (2013.01)

(58) Field of Classification Search
None
See application file for complete search history.

(56) References Cited

U.S. PATENT DOCUMENTS

| | | |
|---|---|---|
| 6,475,789 B1 | 11/2002 | Cech et al. |
| 2009/0175892 A1 | 7/2009 | Langlade-Demoyen et al. |

FOREIGN PATENT DOCUMENTS

| | | |
|---|---|---|
| WO | WO0216555 A2 | 2/2002 |
| WO | WO0216657 A1 | 2/2002 |
| WO | WO0216658 A1 | 2/2002 |
| WO | WO02070668 A2 | 9/2002 |
| WO | WO02072787 A2 | 9/2002 |
| WO | WO02090570 A2 | 11/2002 |
| WO | WO02090571 A2 | 11/2002 |
| WO | WO02101010 A2 | 12/2002 |
| WO | WO03000916 A2 | 1/2003 |
| WO | WO03016474 A2 | 2/2003 |
| WO | WO03034985 A2 | 5/2003 |
| WO | WO2012001170 A1 | 1/2012 |

OTHER PUBLICATIONS

Bernardes et al. ("Telomerase gene therapy in adult and old mice delays aging and increases longevity without increasing cancer." EMBO molecular medicine 4.8 (2012): 691-704).*
Cristofari et al., Telomere length homeostasis requires that telomerase levels are limiting, The EMBO Journal (2006) 25:565-574.
De Jesus et al., Telomerase gene therapy in adult and old mice delays aging and increases longevity without Increasing cancer, EMBO Mol Med (2012) 4(8): 691-704.
Vidale et al., The catalytic and the RNA subunits of human telomerase are required to immortalize equid primary fibroblasts, Chromosoma (2012) 121:475-488.
Sinn et al., Gene therapy progress and prospects: development of improved lentiviral and retroviral vectors—design, biosafety, and production, Gene Ther. Jul. 2005;12(14):1089-98.
Yamaguchi et al., Mutations in TERT, the gene for telomerase reverse transcriptase, in aplastic anemia, N Engl J Med. Apr. 7, 2005;352(14):1413-24.
Bachand et al., Expression of hTERT and hTR in cis reconstitutes and active human telomerase ribonucleoprotein, RNA. May 2000;6(5):778-84.
Li et al., Expression and suppression of human telomerase RNA, Cold Spring Harb Symp Quant Biol. 2006;71:211-5.
Prel et al., Highly efficient in vitro and in vivo delivery of functional RNAs using new versatile MS2-chimeric retrovirus-like particle, Mol Ther Methods Clin Dev. Oct. 21, 2015;2:15039.
Shaw et al., Design and Potential of Non-Integrating Lentiviral Vectors, Biomedicines. Mar. 2014; 2(1): 14-35.

(Continued)

*Primary Examiner* — Kimberly Chong
(74) *Attorney, Agent, or Firm* — Bret E. Field; Bozicevic, Field & Francis LLP

(57) ABSTRACT

Methods of treating an age-related disorder in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

17 Claims, 7 Drawing Sheets

Specification includes a Sequence Listing.

(56) References Cited

OTHER PUBLICATIONS

Chen et al., Episomal lentiviral vectors confer erythropoietin expression in dividing cells, Plasmid. Mar. 2017;90:15-19.

Delluc-Clavieres et al., Efficient gene transfer in skeletal muscle with AAV-derived bicistronic vector using the FGF-1 IRES, Gene Ther. Aug. 2008;15(15):1090-8.

Harley, Telomerase and cancer therapeutics, Nat Rev Cancer. Mar. 2008;8(3):167-79.

Asokan et al., The AAV Vector Toolkit: Poised at the Clinical Crossroads, Molecular Therapy vol. 20 no. 4, 699-708 Apr. 2012.

Armanios, Telomere biology and age-related diseases, Clin Chem Lab Med. Jul. 26, 2018;56(8):1210-1222.

Askou et al., Multigenic lentiviral vectors for combined and tissue-specific expression of miRNA- and protein-based antiangiogenic factors, Mol Ther Methods Clin Dev. Jan. 28, 2015;2:14064.

Puntel et al., Safety profile, efficacy, and biodistribution of a bicistronic high-capacity adenovirus vector encoding a combined immunostimulation and cytotoxic gene therapy as a prelude to a phase I clinical trial for glioblastoma, Toxicol Appl Pharmacol. May 1, 2013;268(3):318-30.

\* cited by examiner

ENHANCING HEALTH IN MAMMALS USING TELOMERASE REVERSE TRANSCRIPTASE GENE THERAPY

INTRODUCTION

The improvement of health during aging is of interest in aging research. Markers of aging include conditions such as epithelial barrier fitness, osteoporosis, glucose intolerance with insulin insensitivity, loss of memory, and neuromuscular degeneration associated with loss of neuromuscular coordination. For example, bone loss is a well-characterized sign of the aging progress both in mammals including humans which results from bone resorption due to osteoblast insufficiency. Therefore, methods that increase life span and ameliorate various age-related parameters are of interest.

Telomeres are regions of repetitive DNA found at the ends of the chromosomes of most eukaryotes. For example, human telomeres include many kilobases of (TTAGGG)n and are associated with various proteins. Small portions of these terminal sequences of telomeric DNA are lost from the tips of the chromosomes during the S phase of the cell cycle because of incomplete DNA replication. Many human cells progressively lose terminal sequences with cell division, a loss that correlates with the apparent absence of telomerase in these cells. The resulting telomere shortening limits cellular lifespan.

Telomerase is a ribonucleoprotein that synthesizes telomeric DNA. Telomerase is made up of two components: (1) an essential structural RNA component (TR or TER) (in humans the component is referred to as hTR or hTER), and (2) a catalytic protein (telomerase reverse transcriptase or TERT) (in humans the component is referred to as hTERT). Telomerase works by adding multiple DNA sequence repeats to the 3' end of DNA in the telomere region, where hTER serves as the template for nucleotide incorporation, and TERT as the catalyst. Both the catalytic protein component and the RNA template component of telomerase are activity-limiting components.

SUMMARY

Methods of treating an age-related disorder or condition in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
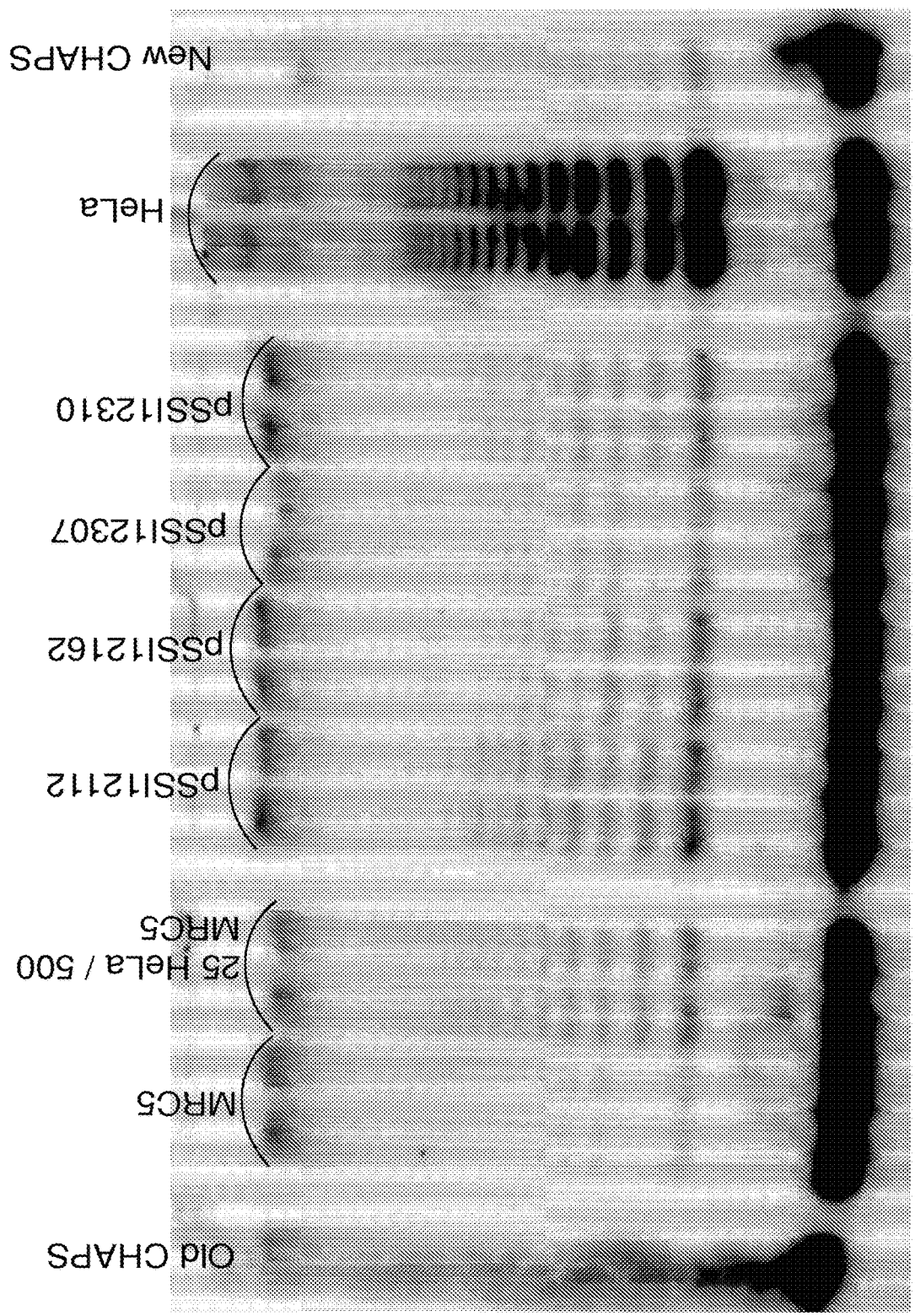
FIG. 1 depicts the results of a TRAP Assay using the vectors pSSI12112, pSSI12162, pSSI12307 and pSSI12310 where sample cells are collected at 7 days post BSD selection, 17 days post infection.

As summarized above, aspects of the invention include methods of treating an age-related disorder in a subject. Aspects of the methods include administering to the subject a nucleic acid vector including a coding sequence for telomerase reverse transcriptase (TERT). In some cases, the vector may include a coding sequence for telomerase RNA (TR). Gene therapy methods that utilize the subject vectors are also provided. Embodiments of the invention include compositions, e.g., nucleic acid vectors and kits, etc., that find use in the subject methods.

The subject methods may lead to increase the expression of telomerase reverse transcriptase and/or telomerase RNA when administered to adult mammals. Administration of the vectors to the subject may extend the lifespan of the subject (e.g., average or maximum lifespan), and may ameliorate one or more markers of ageing, including but not limited to epithelial barrier fitness, osteoporosis, glucose intolerance with insulin insensitivity, loss of memory, and neuromuscular degeneration associated with loss of neuromuscular coordination. The effect may be achieved without increasing the incidence of cancer (malignant neoplastic disease), as assessed by the number of spontaneous neoplasms evident among the population treated.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Vectors

As summarized above, one aspect of the invention is a nucleic acid vector. Application of the subject vector to a subject, e.g. using any convenient method such as a gene therapy method, may result in expression of one or more coding sequences of interest in cells of the subject, to produce a biologically active product that may modulate a biological activity of the cell. In some cases, the vector is a nucleic acid vector comprising a coding sequence for telomerase reverse transcriptase (TERT). In some cases, the nucleic acid vector comprises a coding sequence for one or more telomerase components, such as TERT and telomerase lRNA (TR). In some embodiments, the vector does not include a cancer suppressing sequence.

In some instances, the vector comprises a coding sequence for telomerase reverse transcriptase (TERT) suitable for use in gene therapy. Gene therapy vectors of interest include any kind of particle that comprises a polynucleotide fragment encoding the telomerase reverse transcriptase (TERT) protein, operably linked to a regulatory element such as a promoter, which allows the expression of a functional TERT protein demonstrating telomerase reverse transcriptase activity in the targeted cells. In some cases, TERT is encoded by the nucleic acid sequence as set forth in SEQ ID NO:1 of WO2012001170 or SEQ ID NO:3 of WO2012001170, or is an active fragment or functional equivalent of TERT. In some instances, the vector include a regulatory sequence which is a constitutive promoter such as the cytomegalovirus (CMV) promoter.

The TERT and/or TR sequence used in the gene therapy vector may be derived from the same species as the subject. Any convenient TERT and/or TR sequences, or fragments or functional equivalents thereof, may be utilized in the subject vectors, including sequences from any convenient animal, such as a primate, ungulate, cat, dog, or other domestic pet or domesticated mammal, rabbit, pig, horse, sheep, cow, or a human. For example, gene therapy in humans may be carried out using the human TERT sequence. In some embodiments, the TERT and/or TR sequence is not a murine sequence.

As used herein, "functional equivalent" refers to a nucleic acid molecule that encodes a polypeptide that has TERT activity or a polypeptide that has TERT activity. The functional equivalent may displays 50%, 60%, 70%, 80%, 90%, 95%, 98%, 99%, 100% or more activity compared to a parent TERT sequence. Functional equivalents may be artificial or naturally-occurring. For example, naturally-occurring variants of the TERT sequence in a population fall within the scope of functional equivalent. TERT sequences derived from other species also fall within the scope of the term "functional equivalent", e.g., a murine TERT sequence. In a particular embodiment, the functional equivalent is a nucleic acid with a nucleotide sequence having at least 75%, 80%, 85%, 90%, 95%, 96%, 97%, 98%, 99%, 99.5%, 99.9% identity to the parent sequence. In a further embodiment, the functional equivalent is a polypeptide with an amino acid sequence having at least 75%, 80%, 85%, 90%, 95%, 96%, 97%, 98%, 99%, 99.5%, 99.9% identity to a parent sequence. In the case of functional equivalents, sequence identity should be calculated along the entire length of the nucleic acid. Functional equivalents may contain one or more, e.g. 2, 3, 4, 5, 10, 15, 20, 30 or more, nucleotide insertions, deletions and/or substitutions when compared to a parent sequence.

The term "functional equivalent" also encompasses nucleic acid sequences that encode a TERT polypeptide with at least 75%, 80%, 85%, 90%, 95%, 96%, 97%, 98%, 99%, 99.5%, 99.9% sequence identity to the parent amino acid sequence, but that show little homology to the parent nucleic acid sequence because of the degeneracy of the genetic code.

As used herein, the term "active fragment" refers to a nucleic acid molecule that encodes a polypeptide that has TERT activity or polypeptide that has TERT activity, but which is a fragment of the nucleic acid as set forth in the parent polynucleotide sequence or the amino acid sequence as set forth in parent polypeptide sequence. An active fragment may be of any size provided that TERT activity is retained. A fragment will have at least 75%, 80%, 85%, 90%, 95%, 96%, 97%, 98%, 99%, 99.5%, 100% identity to the parent sequence along the length of the alignment between the shorter fragment and longer parent sequence.

Fusion proteins including these fragments can be comprised in the nucleic acid vectors needed to carry out the invention. For example, an additional 5, 10, 20, 30, 40, 50 or even 100 amino acid residues from the polypeptide sequence, or from a homologous sequence, may be included at either or both the C terminal and/or N terminus without prejudicing the ability of the polypeptide fragment to fold correctly and exhibit biological activity. Sequence identity may be calculated by any one of the various methods in the art, including for example BLAST (Altschul S F, Gish W, Miller W, Myers E W, Lipman D J (1990). "Basic local alignment search tool". J Mol Biol 215 (3): 403-410) and PASTA (Lipman, D J; Pearson, W R (1985). "Rapid and sensitive protein similarity searches". Science 227 (4693): 1435-41; http://fasta.bioch.virginia.edu/fasta www2/fasta list2.shtml) and variations on these alignment programs.

The vector may further include one or more regulatory sequences. Any convenient regulatory sequences or promoter sequences may be utilized in the subject vectors, e.g., as described herein. In some embodiments, the regulatory sequence that is operatively linked to the coding sequence (e.g., the TERT and/or TR sequence) is the cytomegalovirus promoter (CMV), although any other convenient regulatory sequences may be utilized.

Viral Vectors

Any convenient viruses may be utilized in delivering the vector of interest to the subject. Viruses of interest include, but are not limited to a retrovirus, an adenovirus, an adeno-associated virus (AAV), a herpes simplex virus and a lentivirus. Viral gene therapy vectors are well known in the art, see e.g., Heilbronn & Weger (2010) Handb Exp Pharmacal. 197:143-70. Vectors of interest include integrative and non-integrative vectors such as those based on retroviruses, adenoviruses (AdV), adeno-associated viruses (AAV), lentiviruses, pox viruses, alphaviruses, and herpes viruses.

In some cases, non-integrative viral vectors, such as AAV, may be utilized. In one aspect, non-integrative vectors do not cause any permanent genetic modification. The vectors may be targeted to adult tissues to avoid having the subjects under the effect of constitutive telomerase expression from early stages of development. In some instances, non-integrative vectors effectively incorporate a safety mechanism to avoid over-proliferation of TERT expressing cells. The cells may lose the vector (and, as a consequence, the telomerase expression) if they start proliferating quickly.

Non-integrative vectors of interest include those based on adenoviruses (AdV) such as gutless adenoviruses, adeno-associated viruses (AAV), integrase deficient lentiviruses, pox viruses, alphaviruses, and herpes viruses. In certain embodiments, the non-integrative vector used in the invention is an adeno-associated virus-based non-integrative vector, similar to natural adeno-associated virus particles. Examples of adena-associated virus-based non integrative vectors include vectors based on any AAV serotype, i.e. AAVI, AAV2, AAV3, AAV4, AAV5, AAV6, AAV7, AAV8, AAV9, AAVIO, AAVII and pseudotyped AAV. Vectors of interest include those capable of transducing a broad range of tissues at high efficiency, with poor immunogenicity and an excellent safety profile. In some cases, the vectors transduce post-mitotic cells and can sustain long-term gene expression (up to several years) both in small and large animal models of age-related disorders.

Methods

As summarized above, aspects of the invention include methods of administering a nucleic acid vector to a subject. As such, aspects of the invention include contacting the subject with a viral vector, e.g., as described above, under conditions by which expression of one or more telomerase components (such as TERT and/or TR) in the subject results in a beneficial effect on one or more aspects of the subject's health, including increased longevity, delayed osteoporosis, improved epithelial barrier fitness, improved glucose tolerance, improved memory function, and improved neuromuscular coordination. In some cases, the subject did not develop increased incidence of cancer, illustrating the safety of this type of strategy.

In gene therapy methods, genes are directly inserted into cells affected by an age-related condition so that the function of the cells is normalized by expressing the inserted genes. The gene therapy methods may be used to prevent various diseases or age-related conditions or to reinforce treatment by inserting a specific gene into a body cell and granting a new function to the body cell. One aspect in the treatment of such conditions using gene therapy is that the inserted gene be successfully delivered to the nucleus of the target cell and that the gene be expressed strongly. The gene enters the target cell through endocytosis and is transported into the nucleus to be expressed. The gene can be inserted using a carrier such as a liposome since most DNAs are destroyed when entering the cell. However, most of the liposomes are also destroyed when entering the nucleus, thereby decreasing the transporting efficiency. A virus capable of infecting a human can be treated using gene therapy because the virus effectively inserts exogeneous genes into the human body. Specifically, the gene can effectively be transported and expressed by inserting the gene for the gene therapy into the DNA of the virus using gene recombination and infecting the subject (e.g., a human) with the recombinant virus, which can be mass produced in vitro. In some cases, an adenovirus can be effectively used for the gene therapy by using a mechanism of transporting the gene into the nucleus of the target cell with a high efficiency. In addition, retroviruses are being used in many internationally permissible clinical trials (Wiley—The Journal of Gene Medicine Website: http://www.wiley.co.uk/genetherapy). Retroviruses are effective for gene therapy when inserted into cell chromosomal DNA to allow long term expression of the desired protein.

In certain instances, the expression of the TERT and/or TR following gene therapy according to the invention persists for a time of one or more weeks, such as one or more months, e.g., several months to several years.

When treating specific age related disorders, it is advantageous to target the treatment to the effected tissues. The serotype of the capsid protein of the gene therapy vector may thus be selected based on the desired site of gene therapy, e.g., skeletal muscle tissue for treating neuromuscular coordination.

Any convenient methods may be employed. Methods and vectors of interest that may be adapted for use in the subject invention include, but are not limited to the methods and vectors of WO 2012/001170 and Vidale et al. "The catalytic and the IRNA subunits of human telomerase are required to immortalize equid primary fibroblasts." Chromosoma. 2012 Jul. 14. Epub, the disclosures of which are herein incorporated by reference.

In some embodiments, the method of treatment is a gene therapy method and/or the nucleic acid vector used is a gene therapy vector. Gene therapy methods and vectors are well known in the art and generally include delivering a nucleic acid encoding a therapeutically active protein to a subject. The nucleic acid may be delivered in a number of ways including delivering naked DNA such as plasmid or minicircles, the use of liposomes or cationic polymers or other engineered nano-particles containing the nucleic acid, or viral vectors that encapsidate the nucleic acid.

In a further embodiment, the gene therapy is achieved using stable transformation of organisms with an inducible expression system. In certain embodiments, this aspect of the invention does not extend to human subjects. Expression of TERT or TR can be induced at a later date following transformation, for example, once the subject is an adult or an aged adult, or begins to show signs of age-related disorders. Suitable inducible expression systems are known in the art and include the CRE-LOX recombinase based system and the tetracycline-regulated system.

In some embodiments, the present invention is limited to the expression of TERT an/or TR in adult or aged subjects. In certain embodiments, the methods and vectors are utilized with post-mitotic cells within the subjects, and avoid any increased incidence of cancer.

Any convenient subjects may be treated according to the subject methods. The subject may be an adult animal, such as an adult mammal. The mammal may be a primate, ungulate, cat, dog, domestic pet or domesticated mammal. In some cases, the mammal may be a rabbit, pig, horse, sheep, cow, cat or dog, or a human. In certain embodiments the subject is not a murine mammal. An adult subject treated according to the invention may be aged. The term "aged" is applied to an individual who is older than the period of life during which the individuals of its species are generally healthy and free of chronic illness. According to the present application, an "adult" should be a fully developed individual who has attained reproductive ability, is fertile, or who evidences secondary sex characteristics. As used herein, the term adult when applied to humans, for example, describes early adulthood commencing at around 20 years of age and extending to 39; middle adulthood (40 to 59) and late adulthood (60+). As a comparison, a one year old mouse can be considered to be approximately equivalent in age to a 45 year old human. A 2 year old mouse can be considered to be approximately equivalent to an 80 year old human.

The particular protocol that is employed may vary. Administration of the vectors may be achieved using any convenient protocol. Vectors as described above (e.g., retroviral vectors and lentiviral vectors) may be administered in vivo to subjects by any convenient route. The term "administration" refers to the route of introduction of a formulated vector into the body. For example, administration may be intravenous, intramuscular, topical, oral, or by gene gun or hypospray instrumentation. Thus, administration can be direct to a target tissue or through systemic delivery. Administration directly to the target tissue can involve needle injection, hypospray, electroporation, or the gene gun. See, e.g., WO 93/18759, hereby incorporated by reference herein. Alternatively, vectors of the invention can be administered ex vivo or in vitro to cells or tissues using any convenient transfection techniques.

The vectors of the invention can also be transduced into host cells, including but not limited to, embryonic stem cells, somatic stem cells, or progenitor cells. Examples of progenitor host cells which can be transduced by the vectors of the invention include precursors of erythrocytes and hematopoietic stem cells. In another embodiment, the host cell is an erythrocyte. Transduced host cells can be used as a method of achieving erythroid-specific expression of the gene of interest in the treatment of hemoglobinopathies.

In some embodiments, the method does not include concomitant use of a cancer suppressor.

The step of facilitating the production of infectious viral particles in the cells may be carried out using conventional techniques, such as standard cell culture growth techniques. If desired by the skilled artisan, lentiviral stock solutions may be prepared using the vectors and methods of the present invention. Methods of preparing viral stock solutions are known in the art and are illustrated by, e.g., Y. Soneoka et al. (1995) Nucl. Acids Res. 23:628-633, and N. R. Landau et al. (1992) J. Virol. 66:5110-5113. In a method of producing a stock solution in the present invention, lentiviral-permissive cells (referred to herein as producer cells) are transfected with the vector system of the present invention. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The step of collecting the infectious virus particles also can be carried out using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Other methods relating to the use of viral vectors in gene therapy can be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58; Brody, S. L. and Crystal, R. G. (1994) Ann. N.Y. Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration directly into an affected joint. The carrier can be suitable for intravenous, intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Another aspect of the invention pertains to pharmaceutical compositions of the vectors of the invention. In one embodiment, the composition includes a vector in a therapeutically effective amount sufficient to treat or prevent (e.g. ameliorate one or more age-related conditions), and a pharmaceutically acceptable carrier. A "therapeutically effective amount" refers to an amount effective, at dosages and for periods of time necessary, to achieve the desired therapeutic result, such as treatment or amelioration of an age-related condition. A therapeutically effective amount of vector may vary according to factors such as the disease state, age, sex, and weight of the individual, and the ability of the viral vector to elicit a desired response in the individual. Dosage regimens may be adjusted to provide the optimum therapeutic response. A therapeutically effective amount is also one in which any toxic or detrimental effects of the viral vector are outweighed by the therapeutically beneficial effects. The potential toxicity of the viral vectors of the invention can be assayed using cell-based assays or art recognized animal models and a therapeutically effective modulator can be selected which does not exhibit significant toxicity. In a preferred embodiment, a therapeutically effective amount of a viral vector is sufficient to treat or ameliorate one or more age-related conditions in as subject.

Sterile injectable solutions can be prepared by incorporating viral vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

It is to be noted that dosage values may vary with the severity of the condition to be ameliorated. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition.

The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In Vitro Methods

Also included are in vitro methods, where the subject vectors, e.g., as described above are contacted with a sample. The particular protocol that is employed may vary, e.g., depending on the sample. For in vitro protocols, contact of the vector with the sample may be achieved using any convenient protocol. In some instances, the sample includes cells that are maintained in a suitable culture medium, and the vector is introduced into the culture medium. Depending upon the nature of the vector (e.g., a viral vector), the response desired, the manner of contacting or administration, the number of cells present, various protocols may be employed. The term "sample" as used herein relates to a material or mixture of materials, typically, although not necessarily, in fluid form, containing one or more components of interest.

Utility

The vectors and methods of the invention, e.g., as described above, find use in a variety of applications. Applications of interest include, but are not limited to: research applications and therapeutic applications. Methods of the invention find use in a variety of different applications including any convenient application where the subject is experiencing one or more age-related conditions. In some cases, age-related disorders or conditions that may be modulated or ameliorated using the subject vectors and methods include, but are not limited to, osteoporosis, arthrosis, glucose intolerance, insulin resistant, reduced heart, circulatory and/or lung function, cardiovascular disease, loss of memory, loss of neuromuscular coordination and decrease of longevity, or combinations thereof.

The subject vectors and methods find use in a variety of research applications. The subject vectors and methods may be used to analyze the role of telomerase various biological processes including age-related disorders and conditions.

The subject vectors and methods find use in a variety of therapeutic applications. Therapeutic applications of interest include those applications in which the subject is suffering from one or more age-related disorders or conditions. As such, the subject vectors find use in the treatment of a variety of different age-related conditions in various subjects, and may lead to an extended lifespan. For example, the subject vectors and methods may find use in regulated gene therapy.

Extended lifespan may be an increase in the maximum lifespan possible for any particular species of subject. Extended lifespan may be an increase in the average lifespan of an individual of that species who reaches adulthood. Thus, extended lifespan may be a 5%, 10%, 15%, 20% or more increase in maximum lifespan and/or a 5%, 10%, 15%, 20% or more increase in average lifespan.

The application of the invention extends the period of time for which an individual is generally healthy and free of chronic illness and/or the invention ameliorates disorders that appear often in aged and ageing adult population, including reduced epithelial barrier fitness, osteoporosis, glucose intolerance and neuromuscular degeneration associated with loss of neuromuscular coordination. These are well established indicators of ageing progression.

Accordingly, the invention has beneficial effects in at least one of the following group: reducing the incidence of cancer, on delaying and/or ameliorating osteoporosis, improving epithelial barrier fitness, improving glucose tolerance, improving memory function, and improving neuromuscular coordination. The amelioration of age-related disorders provided by the invention can be as a result of reduction of symptoms in an affected subject or a reduction of incidence of the disease or disorder in a population as compared to an untreated population. The application of gene therapy according to the invention has the effect of treating and/or preventing various age-related conditions and diseases, as assessed by particular markers and disorders of ageing. In a further aspect, therefore, the invention refers to a gene therapy method or the used of a nucleic acid vector as described above, for use in the treatment or prevention in a subject of at least a disorder or marker of ageing that is selected from the group of reduced epithelial barrier fitness, osteoporosis, arthrosis, glucose intolerance, insulin resistanance, loss of memory, loss of neuromuscular coordination, increase in cardiovascular disease, decrease in heart, circulatory or lung function and decrease in longevity, or combinations thereof. The gene therapy ameliorates at least one marker of ageing, selected for example, from the group of reduced epithelial barrier fitness, osteoporosis, arthrosis, glucose intolerance, insulin resistance, cardiovascular disease, reduced heart and circulatory function, reduced lung function, loss of memory, loss of neuromuscular coordination or decrease of longevity or combinations thereof.

Kits

Aspects of the invention further include kits, where the kits include one or more components employed in methods of the invention, e.g., vectors, as described herein. In some embodiments, the subject kit includes a vector (as described herein), and one or more components selected from a promoter, a virus, a cell, and a buffer. Any of the components described herein may be provided in the kits, e.g., cells, constructs (e.g., vectors) encoding for TERT and/or TR, components suitable for use in expression systems (e.g., cells, cloning vectors, multiple cloning sites (MSC), bi-directional promoters, an internal ribosome entry site (IRES), etc.), etc. A variety of components suitable for use in making and using constructs, cloning vectors and expression systems may find use in the subject kits. Kits may also include tubes, buffers, etc., and instructions for use. The various reagent components of the kits may be present in separate containers, or some or all of them may be precombined into a reagent mixture in a single container, as desired.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

Aspects of the invention include providing a virus particle that includes a nucleic acid vector, e.g., as described above. Any convenient virus particles may be utilized, and include viral vector particles described above.

Aspects of the invention include providing a cell that includes a nucleic acid vector. The cell that is provided with the vector of interest may vary depending on the specific application being performed. Target cells of interest include eukaryotic cells, e.g., animal cells, where specific types of animal cells include, but are not limited to: insect, worm or mammalian cells. Various mammalian cells may be used, including, by way of example, equine, bovine, ovine, canine, feline, murine, non-human primate and human cells. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells).

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Construction of Vectors pSSI14342: Adeno vector containing hTR and hTERT was constructed.

LITR-U1-hTR-CMV-hTERT-SV40pA-RITR

Region Base Locations:
 Adeno RITR: 2928-3030
 U1 promoter: 6459-6668
 hTR: 6850-7300
 U1-3'box: 7458-7472
 CMV promoter: 7485-8073
 Kozak: 8082-8098
 hTERT: 8087-11482
 SV40pA: 11558-11679
 Adeno LITR: 5973-6075 pSSI10902: Lentiviral vector pSSI10902 was constructed and contains hTERT, Puro gene (for selection of infected cells) and AmCyan gene (a fluorescent protein for color). In pSSI10902, hTERT is expressed using the CMV promoter, Puro gene is expressed using the SV40 promoter, and AmCyan gene is expressed using the CMV promoter. Below is shown the schematic for the pSSI10902 expression cassette. The sequence of this entire vector is also provided (SEQ ID NO: 2).

pSSI10902: 5'-LTR-CMV-hTERT-SV40-Puro-CMV-AmCyan-LTR-3'

Region Base Locations:
 5' LTR: 230-410
 CMV promoter: 1883-2374
 Kozak: 2627-2643
 hTERT: 2632-6027
 SV40 promoter: 6053-6286
 CMV promoter: 7242-7830
 AmCyan: 7891-8577
 3' LTR: 9315-9495 pSSI12112: The lentiviral vector pSSI12112 was constructed as a dual vector containing both hTR and hTERT in the same vector. hTR is expressed using the U1 promoter and hTERT is expressed using the CMV promoter. Note: this plasmid also contains the BSD gene being expressed by the PGK promoter which allows selection for cells infected with the lentivirus created using this plasmid. Below is shown a schematic of the expression cassette for pSSI12112. The sequence of this entire vector is also attached (SEQ ID NO:3).

pSSI12112: 5'-LTR-U1-hTR-PGK-BSD-CMV-hTERT-LTR-3'

Region Base Locations:
  5' LTR: 230-410
  U1 promoter: 1876-2085
  hTR: 2267-2717
  U1-3'box: 2875-2889
  PGK promoter: 2916-3421
  BSD: 3499-3894
  CMV promoter: 4023-4611
  Kozak: 4620-4636
  hTERT: 4625-8020
  3' LTR: 8200-8380

Further vectors were constructed and tested as described herein.
  pSSI12112=LTR-U1-hTR-PGK-BSD-CMV-TSS-hTERT-LTR
  pSSI12162=LTR-U1-hTR-PGK-BSD-CMV-TSS-nonhTERT-LTR
  pSSI12307=LTR-PGK-BSD-CMV-TSS-hTERT-LTR
  pSSI12310=LTR-PGK-BSD-CMV-TSS-nonhTERT-LTR The viral vectors are tested in vitro or in vivo using any convenient methods. Methods of interest that are adapted for use in testing the viral vectors described herein include those methods described by WO 2012/001170 and Vidale et al. "The catalytic and the RNA subunits of human telomerase are required to immortalize equid primary fibroblasts." Chromosoma. 2012 Jul. 14. Epub.
Project 2273 pSSI12112 (hTR+hTERT) was tested in MRC5 cells. At 7 days post BSD selection, the TRAP activity from pSSI12112 is slightly stronger than the other 3 test samples (pSSI12162 (hTR+non-functional hTERT), pSSI12307 (hTERT), and pSSI12310 (non-functional hTERT)). At 14 days post selection, the pSSI12112 TRAP activity is less than the other 3 samples and eventually diminishes to no TRAP signal at 21 days post BSD selection.

FIG. 1 depicts the results of a TRAP Assay using the vectors pSSI12112, pSSI12162, pSSI12307 and pSSI12310 where sample cells are collected at 7 days post BSD selection, 17 days post infection.

Figure 2:
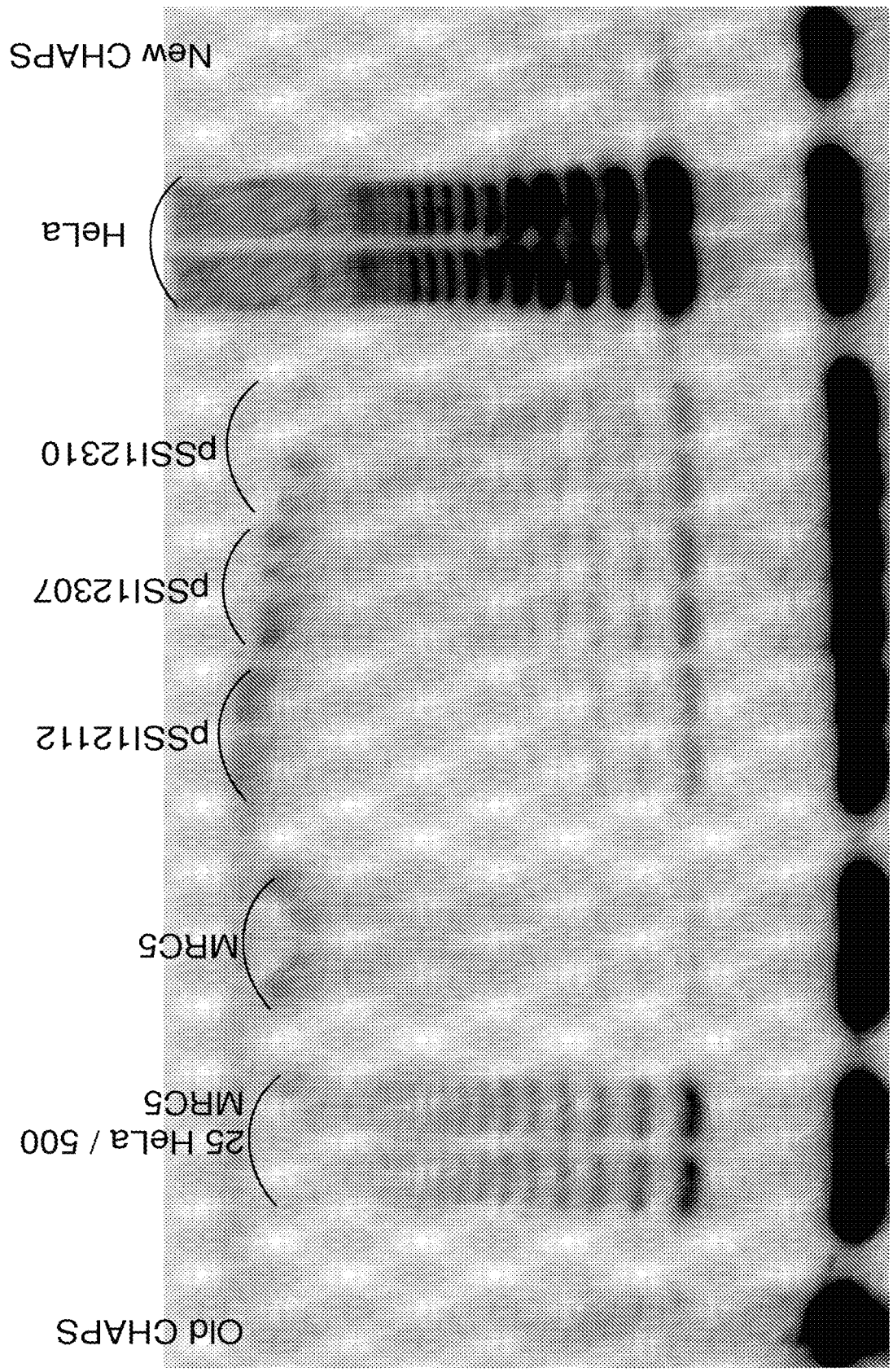
FIG. 2 depicts the results of a TRAP Assay using the vectors pSSI12112, pSSI12307 and pSSI12310 where sample cells are collected at 14 days post BSD selection, 24 days post infection.

FIG. 2 depicts the results of a TRAP Assay using the vectors pSSI12112, pSSI12307 and pSSI12310 where sample cells are collected at 14 days post BSD selection, 24 days post infection.

Figure 3:
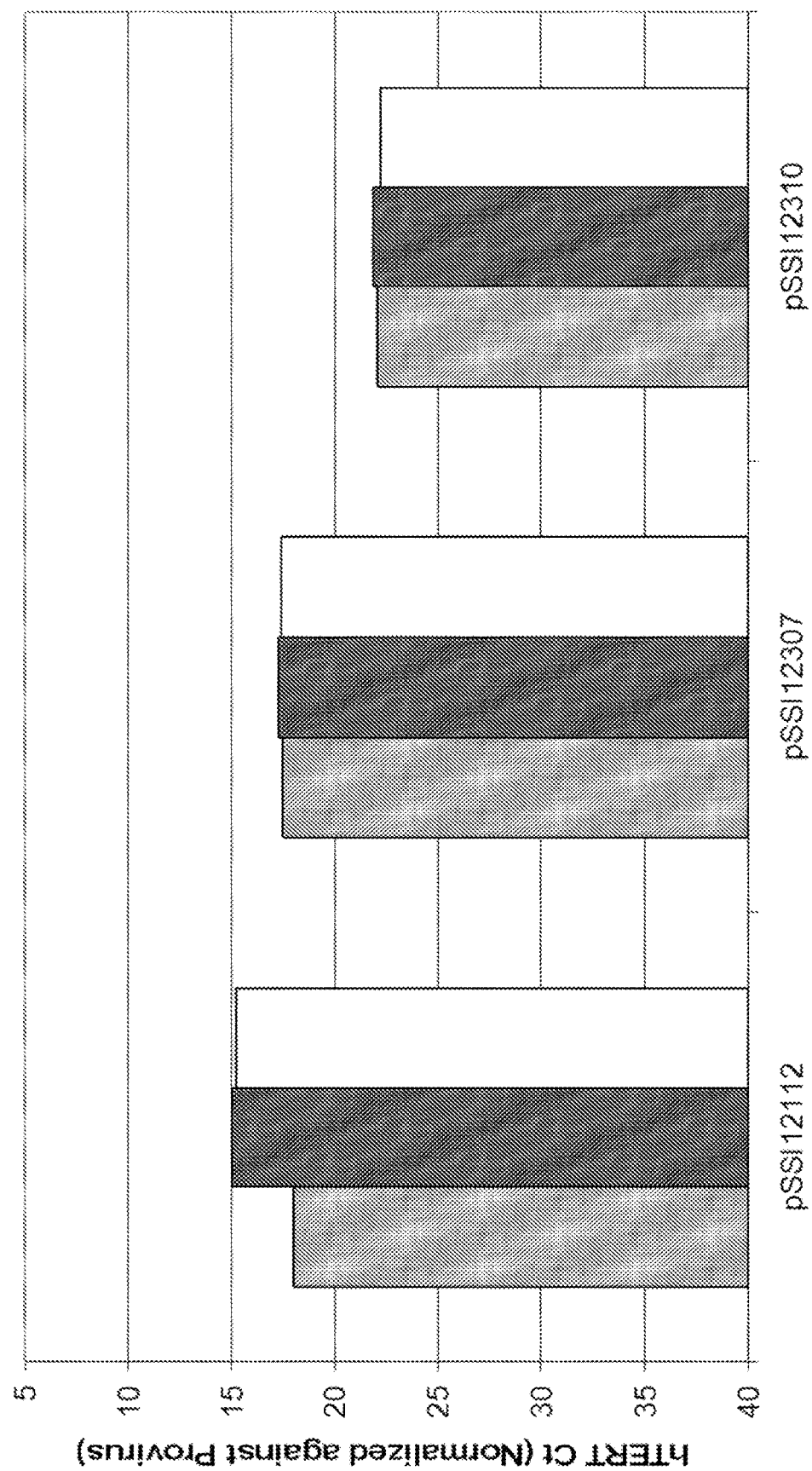
FIG. 3 illustrates RT-PCR results for hTERT Ct (normalized against provirus) using the vectors pSSI12112, pSSI12307 and pSSI12310 where sample cells are collected at 14 days post BSD selection, 24 days post infection.

FIG. 3 illustrates RT-PCR results for hTERT Ct (normalized against provirus) using the vectors pSSI12112, pSSI12307 and pSSI12310 where sample cells are collected at 14 days post BSD selection, 24 days post infection.

Figure 4:
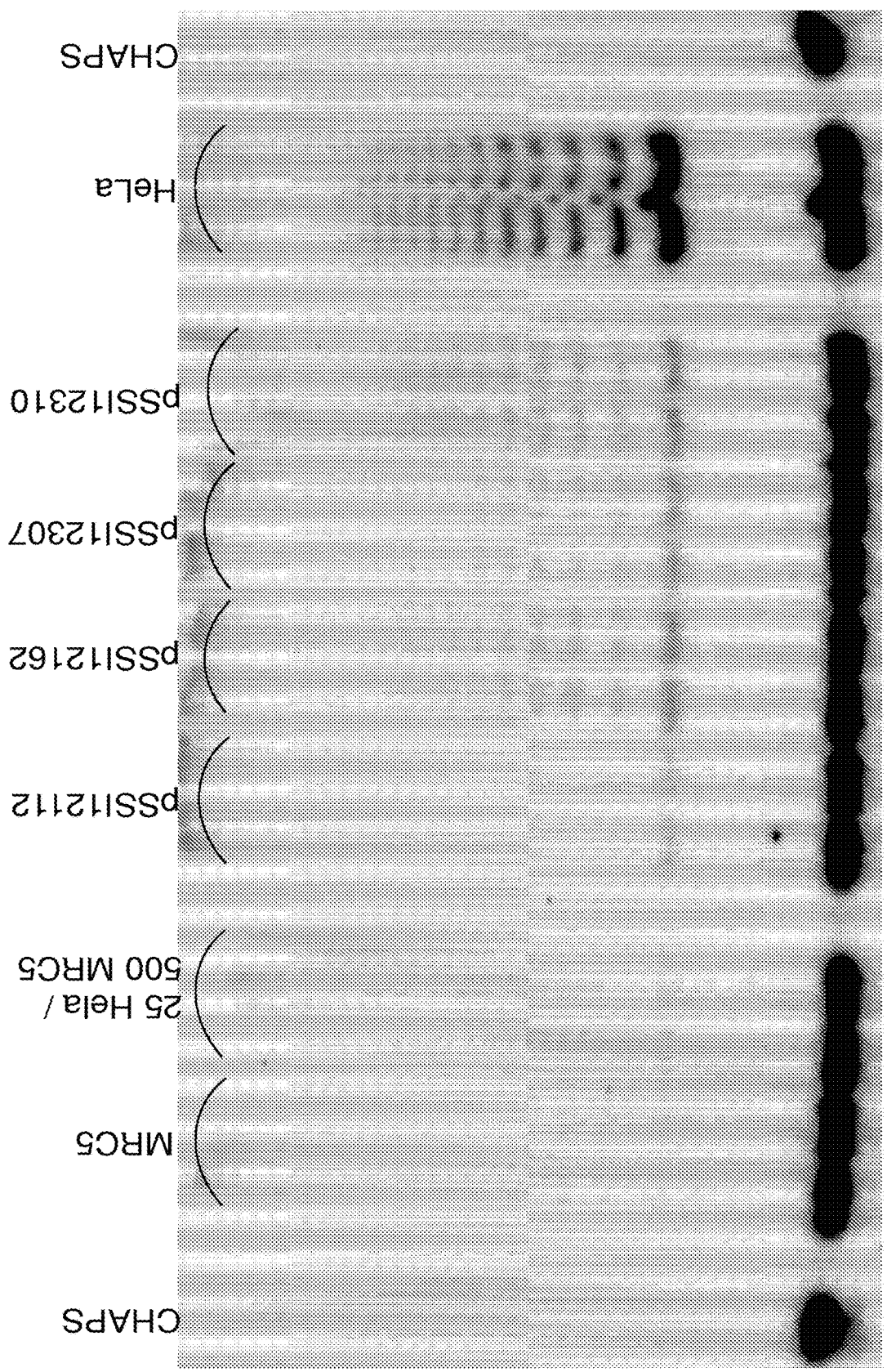
FIG. 4 depicts the results of a TRAP Assay using the vectors pSSI12112, pSSI12162, pSSI12307 and pSSI12310 where sample cells are collected at 21 days post BSD selection, 31 days post infection.

FIG. 4 depicts the results of a TRAP Assay using the vectors pSSI12112, pSSI12162, pSSI12307 and pSSI12310 where sample cells are collected at 21 days post BSD selection, 31 days post infection.

Figure 5:
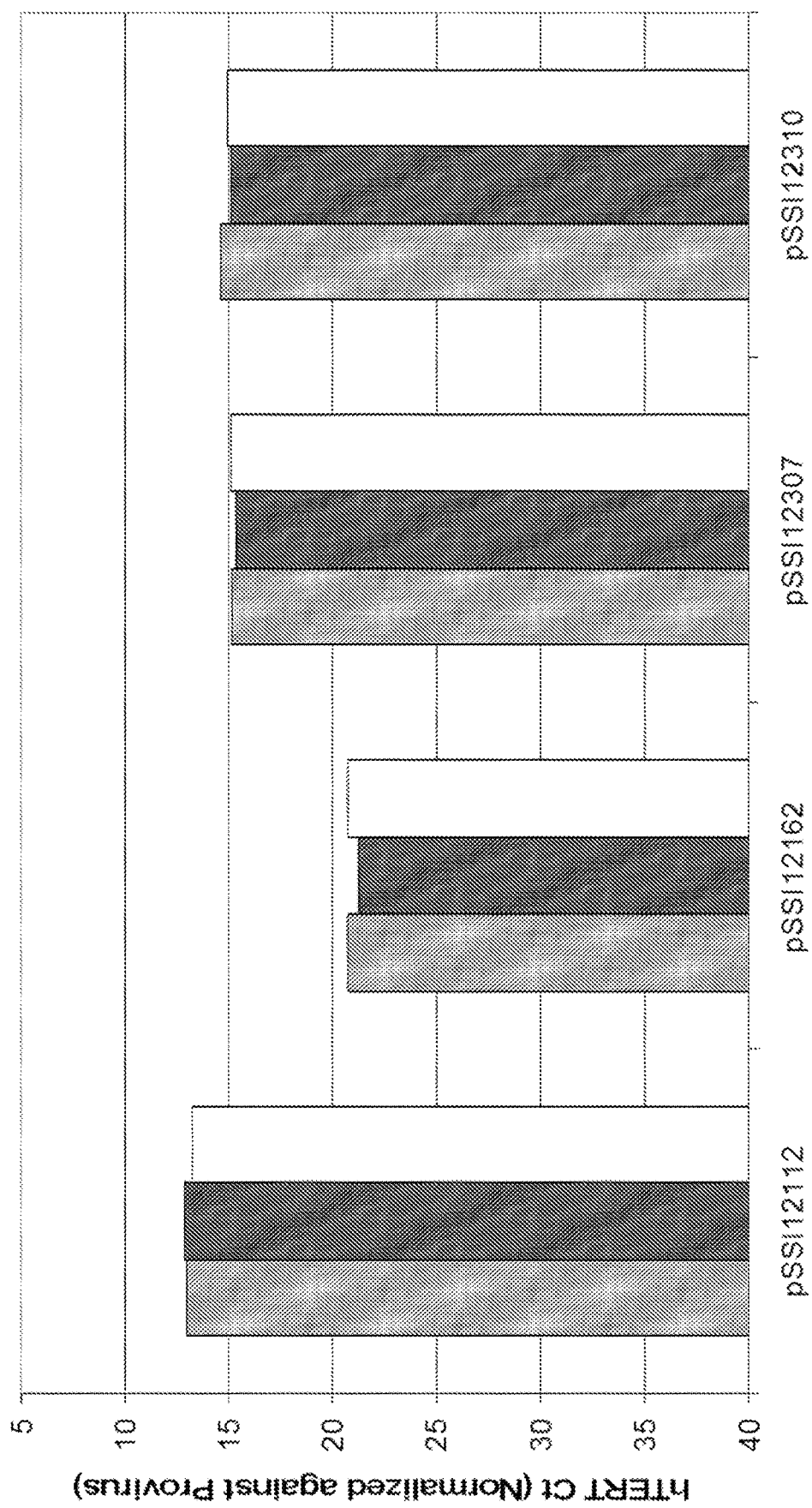
FIG. 5 illustrates RT-PCR results for hTERT Ct (normalized against provirus) using the vectors pSSI12112, pSSI12162, pSSI12307 and pSSI12310 where sample cells are collected at 14 days post BSD selection, 24 days post infection.

FIG. 5 illustrates RT-PCR results for hTERT Ct (normalized against provirus) using the vectors pSSI12112, pSSI12162, pSSI12307 and pSSI12310 where sample cells are collected at 14 days post BSD selection, 24 days post infection.

Figure 6:
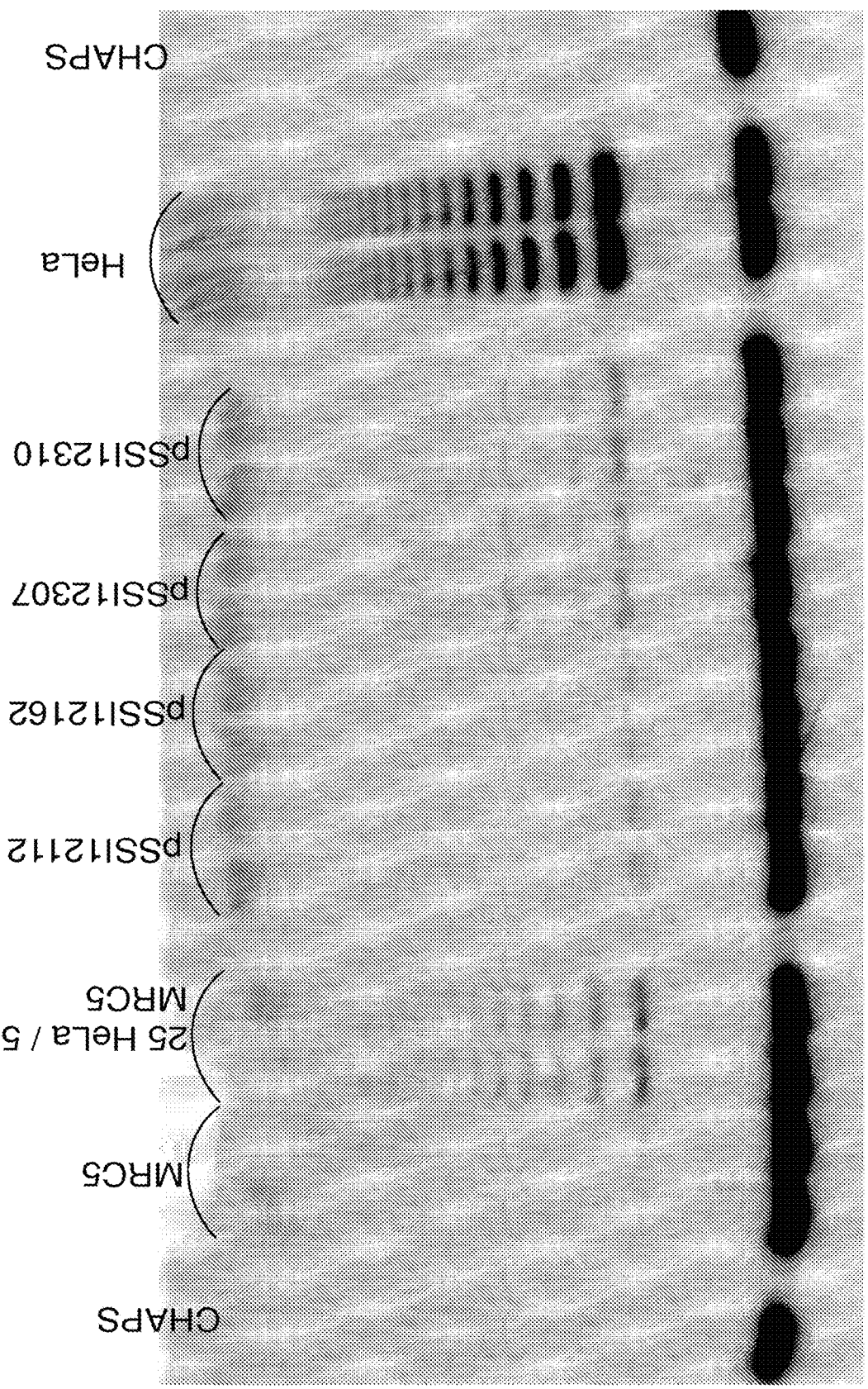
FIG. 6 depicts the results of a TRAP Assay using the vectors pSSI12112, pSSI12162, pSSI12307 and pSSI12310 where sample cells are collected at 49 days post BSD selection, 59 days post infection.

FIG. 6 depicts the results of a TRAP Assay using the vectors pSSI12112, pSSI12162, pSSI12307 and pSSI12310 where sample cells are collected at 49 days post BSD selection, 59 days post infection.

Figure 7:
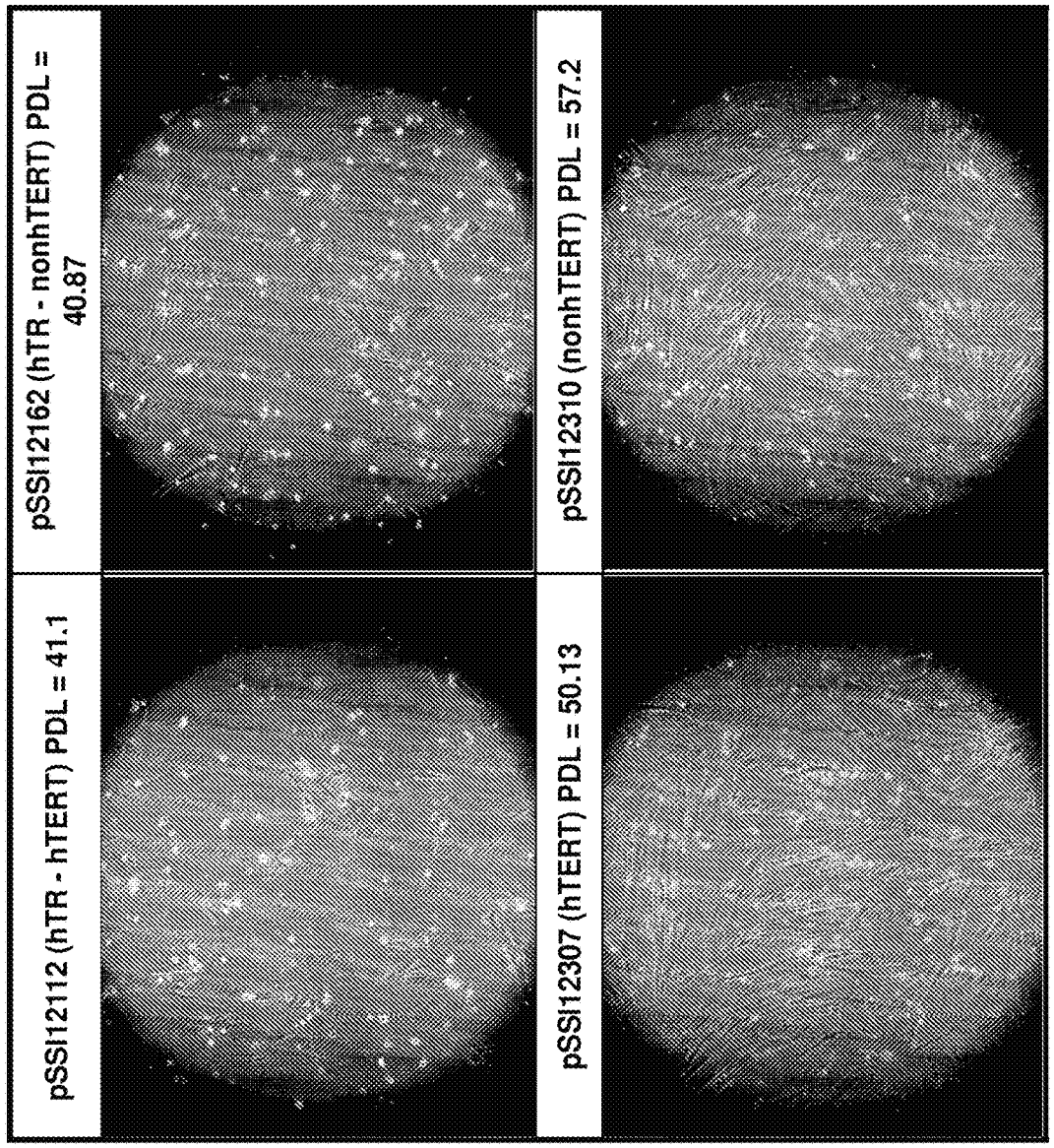
FIG. 7 depicts images comparing cell growth of cells that were maintained in 1.5 ug/ml BSD for 55 days post selection using the vectors pSSI12112, pSSI12162, pSSI12307 and pSSI12310.

FIG. 7 depicts images comparing cell growth of cells that were maintained in 1.5 ug/ml BSD for 55 days post selection using the vectors pSSI12112, pSSI12162, pSSI12307 and pSSI12310.

```
pSSI14342
                                                           (SEQ ID NO: 1)
TCACAGAACCCTAGTATTCAACCTGCCACCTCCCTCCCAACACACAGAGTACACAGTCCTTTCTC

CCCGGCTGGCCTTAAAAAGCATCATATCATGGGTAACAGACATATTCTTAGGTGTTATATTCCACA

CGGTTTCCTGTCGAGCCAAACGCTCATCAAGTGATATTAATAAACTCCCCGGGCAGCTCACTTAA

GTTCATGTCGCTGTCCAGCTGCTGAGCCACAGGCTGCTGTCCAACTTGCGGTTGCTTAACGGGC

GGCGAAGGAGAAGTCCACGCCTACATGGGGGGAGAGTCATAATCGTGCATCAGGATAGGGCGG

TGGTGCTGCAGCAGCGCGCGAATAAACTGCTGCCGCCGCCGCTCCGTCCTGCAGGAATACAACA

TGGCAGTGGTCTCCTCAGCGATGATTCGCACCGCCCGCAGCATAAGGCGCTTGTCCTCCGGGCA

CAGCAGCGCACCCTGATCTCACTTAAATCAGCACAGTAACTGCAGCACAGCACCACAATATTGTT

CAAAATCCCACAGTGCAAGGCGCTGTATCCAAAGCTCATGGCGGGGACCACAGAACCCACGTGG

CCATCATACCACAAGCGCAGGTAGATTAAGTGGCGACCCCTCATAAACACGCTGGACATAAACAT

TACCTCTTTTGGCATGTTGTAATTCACCACCTCCCGGTACCATATAAACCTCTGATTAAACATGGC

GCCATCCACCACCATCCTAAACCAGCTGGCCAAAACCTGCCCCGCCGGGNTATACACTGCAGGG

AACCGGGACTTGGACAATGACAAGTGGGAGAGCCCAGGACTCGTAACCATGGATCATCATGCTC

GTCATGATATCAATGTTGGCACAACACAGGCACACGTGCATACACTTCCTCAGGATTACAAGCTC

CTCCCGCGTTAGAACCATATCCCAGGGAACAACCCATTCCTGAATCAGCGTAAATCCCACACTGC

AGGGAAGACCTCGCACGTAACTCACGTTGTGCATTGTCAAAGTGTTACATTCGGGCAGCAGCGG

ATGATCCTCCAGTATGGTAGCGCGGGTTTCTGTCTCAAAAGGAGGTAGACGATCCCTACTGTACG

GAGTGCGCCGAGACAACCGAGATCGTGTTGGTCGTAGTGTCATGCCAAATGGAACGCCGGACGT

AGTCATATTTCCTGAAGCAAAACCAGGTGCGGGCGTGACAAACAGATCTGCGTCTCCGGTCTCG
```

-continued

```
CCGCTTAGATCGCTCTGTGTAGTAGTTGTAGTATATCCACTCTCTCAAAGCATCCAGGCGCCCCC

TGGCTTCGGGTTCTATGTAAACTCCTTCATGCGCCGCTGCCCTGATAACATCCACCACCGCAGAA

TAAGCCACACCCAGCCAACCTACACATTCGTTCTGCGAGTCACACACGGGAGGAGCGGGAAGAG

CTGGAAGAACCATGTTTTTTTTTTATTCCAAAAGATTATCCAAAACCTCAAAATGAAGATCTATTA

AGTGAACGCGCTCCCCTCCGGTGGCGTGGTCAAACTCTACAGCCAAAGAACAGATAATGGCATT

TGTAAGATGTTGCACAATGGCTTCCAAAAGGCAAACGGCCCTCACGTCCAAGTGGACGTAAAGG

CTAAACCCTTCAGGGTGAATCTCCTCTATAAACATTCCAGCACCTTCAACCATGCCCAATAATTC

TCATCTCGCCACCTTCTCAATATATCTCTAAGCAAATCCCGAATATTTAAGTCCGGGCCATTGTAA

AAAATTTGGCTCCAGAGCGCCCTCCACCTTCAGCCTCAAGCAGCGAATCATGATTGCAAAAATTC

AGGTTCCTCACAGACCTGTATAAGATTCAAAAGCGGAACATTAACAAAAATACCGCGATCCCGTA

GGTCCCTTCGCAGGGCCAGCTGAACATAATCGTGCAGGTCTGCACGGACCAGCGCGGCCACTT

CCCCGCCAGGAACCATGACAAAAGAACCCACACTGATTATGACACGCATACTCGGAGCTATGCTA

ACCAGCGTAGCCCCGATGTAAGCTTGTTGCATGGGCGGCGATATAAAATGCAAGGTGCTGCTCA

AAAAATCAGGCAAAGCCTCGCGCAAAAAAGAAAGCACATCGTAGTCATGCTCATGCAGATAAAGG

CAGGTAAGCTCCGGAACCACCACAGAAAAAGACACCATTTTTCTCTCAAACATGTCTGCGGGTTT

CTGCATAAACACAAAATAAAATAACAAAAAAACATTTAAACATTAGAAGCCTGTCTTACAACAGGAA

AAACAACCCTTATAAGCATAAGACGGACTACGGCCATGCCGGCGTGACCGTAAAAAAACTGGTCA

CCGTGATTAAAAAGCACCACCGACAGCTCCTCGGTCAGTCCGGAGTCATAATGTAAGACTCGGTA

AACACATCAGGTTGATTCACATCGGTCAGTGTTAAAAAGCGACCGAAATAGCCNGGGGGAATACA

ATACCCGCAGGCGTAGAGACAACATTACAGCCCCCATAGGAGGTATAACAAAATTAATAGGAGAG

AAAAACACATAAACACCTGAAAAACCCTCCTGCCTAGGCAAAATAGCACCCTCCCGCTCCAGAAC

AACATACAGCGCTTCCACAGCGGCAGCCATAACAGTCAGCCTTACCAGTAAAAAAGAAAACCTAT

TAAAAAAACACCACTCGACACGGCACCAGCTCAATCAGTCACAGTGTAAAAAAGGGCCAAGTGCA

GAGCGAGTATATATAGGACTAAAAAATGACGGTAACGGTTAAAGTCCACAAAAAACACCCAGAAA

ACCGCACGCGAACCTACGCCCAGAAACGAAAGCCAAAAAACCCACAACTTCCTCAAATCGTCACT

TCCGTTTTCCCACGTTACGTCACTTCCCATTTTAAGAAAACTACAATTCCCAACACATACAAGTTAC

TCCGCCCTAAAACCTACGTCACCCGCCCCGTTCCCACGCCCCGCGCCACGTCACAAACTCCACC

CCCTCATTATCATATTGGCTTCAATCCAAAATAAGGTATATTATTGATGATGTTAATTAACATGCAT

GGATCCATATGCGGTGTGAAATACCGCACAGATGCGTAAGGAGAAAATACCGCATCAGGCGCTC

TTCCGCTTCCTCGCTCACTGACTCGCTGCGCTCGGTCGTTCGGCTGCGGCGAGCGGTATCAGCT

CACTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGGCT

CCGCCCCCCTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCGACCCTGCC

GCTTACCGGATACCTGTCCGCCTTTCTCCCTTCGGGAAGCGTGGCGCTTTCTCATAGCTCACGCT

GTAGGTATCTCAGTTCGGTGTAGGTCGTTCGCTCCAAGCTGGGCTGTGTGCACGAACCCCCCGT

TCAGCCCGACCGCTGCGCCTTATCCGGTAACTATCGTCTTGAGTCCAACCCGGTAAGACACGAC

TTATCGCCACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGGACAGTATTTGGTATCTGCGCT

CTGCTGAAGCCAGTTACCTTCGGAAAAAGAGTTGGTAGCTCTTGATCCGGCAAACAAACCACCGC

TGGTAGCGGTGGTTTTTTTGTTTGCAAGCAGCAGATTACGCGCAGAAAAAAAGGATCTCAAGAAG
```

-continued

```
ATCCTTTGATCTTTTCTACGGGGTCTGACGCTCAGTGGAACGAAAACTCACGTTAAGGGATTTTG

GTCATGAGATTATCAAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCTGCAACTTT

ATCCGCCTCCATCCAGTCTATTAATTGTTGCCGGGAAGCTAGAGTAAGTAGTTCGCCAGTTAATA

GTTTGCGCAACGTTGTTGCCATTGCTGCAGCCATGAGATTATCAAAAAGGATCTTCACCTAGATC

CTTTTCACGTAGAAAGCCAGTCCGCAGAAACGGTGCTGACCCCGGATGAATGTCAGCTACTGGG

CTATCTGGACAAGGGAAAACGCAAGCGCAAAGAGAAAGCAGGTAGCTTGCAGTGGGCTTACATG

GCGATAGCTAGACTGGGCGGTTTTATGGACAGCAAGCGAACCGGAATTGCCAGCTGGGGCGCC

CTCTGGTAAGGTTGGGAAGCCCTGCAAAGTAAACTGGATGGCTTTCTTGCCGCCAAGGATCTGAT

GGCGCAGGGGATCAAGCTCTGATCAAGAGACAGGATGAGGATCGTTTCGCATGATTGAACAAGA

TGGATTGCACGCAGGTTCTCCGGCCGCTTGGGTGGAGAGGCTATTCGGCTATGACTGGGCACAA

CAGACAATCGGCTGCTCTGATGCCGCCGTGTTCCGGCTGTCAGCGCAGGGGCGCCCGGTTCTTT

TTGTCAAGACCGACCTGTCCGGTGCCCTGAATGAACTGCAAGACGAGGCAGCGCGGCTATCGTG

GCTGGCCACGACGGGCGTTCCTTGCGCAGCTGTGCTCGACGTTGTCACTGAAGCGGGAAGGGA

CTGGCTGCTATTGGGCGAAGTGCCGGGGCAGGATCTCCTGTCATCTCACCTTGCTCCTGCCGAG

AAAGTATCCATCATGGCTGATGCAATGCGGCGGCTGCATACGCTTGATCCGGCTACCTGCCCATT

CGACCACCAAGCGAAACATCGCATCGAGCGAGCACGTACTCGGATGGAAGCCGGTCTTGTCGAT

CAGGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGACCGCTA

TCAGGACATAGCGTTGGCTACCCGTGATATTGCTGAAGAGCTTGGCGGCGAATGGGCTGACCGC

TTCCTCGTGCTTTACGGTATCGCCGCTCCCGATTCGCAGCGCATCGCCTTCTATCGCCTTCTTGA

CGAGTTCTTCTGAATTTTGTTAAAATTTTTGTTAAATCAGCTCATTTTTTAACCAATAGGCCGAAAT

CGGCAACATCCCTTATAAATCAAAAGAATAGACCGCGATAGGGTTGAGTGTTGTTCCAGTTTGGA

ACAAGAGTCCACTATTAAAGAACGTGGACTCCAACGTCAAAGGGCGAAAAACCGTCTATCAGGGC

GATGGCCCACTACGTGAACCATCACCCAAATCAAGTTTTTTGCGGTCGAGGTGCCGTAAAGCTCT

AAATCGGAACCCTAAAGGGAGCCCCCGATTTAGAGCTTGACGGGGAAAGCCGGCGAACGTGGC

GAGAAAGGAAGGGAAGAAAGCGAAAGGAGCGGGCGCTAGGGCGCTGGCAAGTGTAGCGGTCA

CGCTGCGCGTAACCACCACACCCGCGCGCTTAATGCGCCGCTACAGGGCGCGTCCATTCGCCA

TTCAGGATCGAATTAATTCTTAATTAACATCATCAATAATATACCTTATTTTGGATTGAAGCCAATAT

GATAATGAGGGGGTGGAGTTTGTGACGTGGCGCGGGGCGTGGGAACGGGGCGGGTGACGTAG

TAGTGTGGCGGAAGTGTGATGTTGCAAGTGTGGCGGAACACATGTAAGCGACGGATGTGGCAAA

AGTGACGTTTTTGGTGTGCGCCGGTGTACACAGGAAGTGACAATTTTCGCGCGGTTTTAGGCGG

ATGTTGTAGTAAATTTGGGCGTAACCGAGTAAGATTTGGCCATTTTCGCGGGAAAACTGAATAAG

AGGAAGTGAAATCTGAATAATTTTGTGTTACTCATAGCGCGTAATACTGGTACCGCGGCCGCCTC

GAGTCTAGAGATATCGAATTCAAGCTTAAGGTGCACGGCCCACGTGGCCACTAGTAATTTTTCTG

CAGAAAACGTACCCGGGGATCCTCTAGGATCCCACCGAAAGGTTGCTCCTTAACACAGGCTAAG
```

```
-continued
GACCAGCTTCTTTGGGAGAGAACAGACGCAGGGGCGGGAGGGAAAAAGGGAGAGGCAGACGTC
ACTTCCCCTTGGCGGCTCTGGCAGCAGATTGGTCGGTTGAGTGGCAGAAAGGCAGACGGGGAC
TGGGCAAGGCACTGTCGGTGACATCACGGACAGGGCGACTTCTATGTAGATGAGGCAGCGCAG
AGGCTGCTGCTTCGCCACTTGCTGCTTCGCCACGAAGGAGTTCCCGTGCCCTGGGAGCGGGTTC
AGGACCGCGGATCGGAAGTGAGAATCCCAGCTGTGTGTCAGGGCTGGAAAGGGCTCGGGAGTG
CGCGGGGCAAGTGACCGTGTGTGTAAAGAGTGAGGCGTATGAGGCTGTGTCGGGGCAGAGCCC
GAAGATCCGGGTTGCGGAGGGTGGGCCTGGGAGGGGTGGTGGCCATTTTTTGTCTAACCCTAAC
TGAGAAGGGCGTAGGCGCCGTGCTTTTGCTCCCCGCGCGCTGTTTTTCTCGCTGACTTTCAGCG
GGCGGAAAAGCCTCGGCCTGCCGCCTTCCACCGTTCATTCTAGAGCAAACAAAAAATGTCAGCT
GCTGGCCCGTTCGCCCCTCCCGGGGACCTGCGGCGGGTCGCCTGCCCAGCCCCCGAACCCCG
CCTGGAGGCCGCGGTCGGCCCGGGGCTTCTCCGGAGGCACCCACTGCCACCGCGAAGAGTTG
GGCTCTGTCAGCCGCGGGTCTCTCGGGGGCGAGGGCGAGGTTCAGGCCTTTCAGGCCGCAGG
AAGAGGAACGGAGCGAGTCCCCGCGCGCGGCGCGATTCCCTGAGCTGTGGGACGTGCACCCA
GGACTCGGCTCACACATGCAGTTCGCTTTCCTGTTGGTGGGGGAACGCCGATCGTGCGCATCC
GTCACCCCTCGCCGGCAATGGGGGCTTGTGAACCCCCAAACCTGACTGACTGGGCCAGTGTGCT
GCAAATTGGCAGGAGACGTGAAGGCACCTCCAAAGTCGACTTTCTGGAGTTTCAAAAACAGACC
GTACGATGCATTAGTTATTAATAGTAATCAATTACGGGGTCATTAGTTCATAGCCCATATATGGAG
TTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCAAGTACGCC
CCCTATTGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTGGTTTA
GTGAACCGTCAGATCCGCTAGCCCCACCATGCCGCGCGCTCCCCGCTGCCGAGCCGTGCGCTC
CCTGCTGCGCAGCCACTACCGCGAGGTGCTGCCGCTGGCCACGTTCGTGCGGCGCCTGGGGC
CCCAGGGCTGGCGGCTGGTGCAGCGCGGGGACCCGGCGGCTTTCCGCGCGCTGGTGGCCCAG
TGCCTGGTGTGCGTGCCCTGGGACGCACGGCCGCCCCCGCCGCCCCCTCCTTCCGCCAGGTG
TCCTGCCTGAAGGAGCTGGTGGCCCGAGTGCTGCAGAGGCTGTGCGAGCGCGGCGCGAAGAAC
GTGCTGGCCTTCGGCTTCGCGCTGCTGGACGGGCCCGCGGGGCGCCCCGAGGCCTTCAC
CACCAGCGTGCGCAGCTACCTGCCCAACACGGTGACCGACGCACTGCGGGGAGCGGGCGT
GGGGGCTGCTGTTGCGCCGCGTGGGCGACGACGTGCTGGTTCACCTGCTGGCACGCTGCGCG
CTCTTTGTGCTGGTGGCTCCCAGCTGCGCCTACCAGGTGTGCGGGCCGCCGCTGTACCAGCTC
GGCGCTGCCACTCAGGCCCGGCCCCCGCCACACGCTAGTGGACCCCGAAGGCGTCTGGGATG
CGAACGGGCCTGGAACCATAGCGTCAGGGAGGCCGGGGTCCCCCTGGGCCTGCCAGCCCCGG
GTGCGAGGAGGCGCGGGGGCAGTGCCAGCCGAAGTCTGCCGTTGCCCAAGAGGCCCAGGCGT
GGCGCTGCGCCTGAGCCGGAGCGGACGCCCGTTGGGCAGGGGTCCTGGGCCCACCCGGGCAG
GACGCGTGGACCGAGTGACCGTGGTTTCTGTGTGGTGTCACCTGCCAGACCCGCCGAAGAAGC
CACCTCTTTGGAGGGTGCGCTCTCTGGCACGCGCCACTCCCACCCATCCGTGGGCCGCCAGCA
CCACGCGGGCCCCCCATCCACATCGCGGCCACCACGTCCCTGGGACACGCCTTGTCCCCCGGT
```

-continued

```
GTACGCCGAGACCAAGCACTTCCTCTACTCCTCAGGCGACAAGGAGCAGCTGCGGCCCTCCTTC

CTACTCAGCTCTCTGAGGCCCAGCCTGACTGGCGCTCGGAGGCTCGTGGAGACCATCTTTCTGG

GTTCCAGGCCCTGGATGCCAGGGACTCCCCGCAGGTTGCCCCGCCTGCCCCAGCGCTACTGGC

AAATGCGGCCCCTGTTTCTGGAGCTGCTTGGGAACCACGCGCAGTGCCCCTACGGGGTGCTCCT

CAAGACGCACTGCCCGCTGCGAGCTGCGGTCACCCCAGCAGCCGGTGTCTGTGCCCGGGAGAA

GCCCCAGGGCTCTGTGGCGGCCCCGAGGAGGAGGACACAGACCCCCGTCGCCTGGTGCAGC

TGCTCCGCCAGCACAGCAGCCCCTGGCAGGTGTACGGCTTCGTGCGGGCCTGCCTGCGCCGGC

TGGTGCCCCAGGCCTCTGGGGCTCCAGGCACAACGAACGCCGCTTCCTCAGGAACACCAAGA

AGTTCATCTCCCTGGGGAAGCATGCCAAGCTCTCGCTGCAGGAGCTGACGTGGAAGATGAGCGT

GCGGGGCTGCGCTTGGCTGCGCAGGAGCCCAGGGGTTGGCTGTGTTCCGGCCGCAGAGCACC

GTCTGCGTGAGGAGATCCTGGCCAAGTTCCTGCACTGGCTGATGAGTGTGTACGTCGTCGAGCT

GCTCAGGTCTTTCTTTTATGTCACGGAGACCACGTTTCAAAAGAACAGGCTCTTTTTCTACCGGAA

GAGTGTCTGGAGCAAGTTGCAAAGCATTGGAATCAGACAGCACTTGAAGAGGGTGCAGCTGCGG

GAGCTGTCGGAAGCAGAGGTCAGGCAGCATCGGGAAGCCAGGCCCGCCCTGCTGACGTCCAGA

CTCCGCTTCATCCCCAAGCCTGACGGGCTGCGGCCGATTGTGAACATGGACTACGTCGTGGGAG

CCAGAACGTTCCGCAGAGAAAAGAGGGCCGAGCGTCTCACCTCCAGGGTGAAGGCACTGTTCA

GCGTGCTCAACTACGAGCGGGCGCGGCGCCCCGGCCTCCTGGGCGCCTCTGTGCTGGGCCTG

GACGATATCCACAGGGCCTGGCGCACCTTCGTGCTGCGTGTGCGGGCCCAGGACCCGCCGCCT

GAGCTGTACTTTGTCAAGGTGGATGTGACGGGCGCGTACGACACCATCCCCCAGGACAGGCTCA

CGGAGGTCATCGCCAGCATCATCAAACCCCAGAACACGTACTGCGTGCGTCGGTATGCCGTGGT

CCAGAAGGCCGCCCATGGGCACGTCCGCAAGGCCTTCAAGAGCCACGTCTCTACCTTGACAGAC

CTCCAGCCGTACATGCGACAGTTCGTGGCTCACCTGCAGGAGACCAGCCCGCTGAGGGATGCC

GTCGTCATCGAGCAGAGCTCCTCCCTGAATGAGGCCAGCAGTGGCCTCTTCGACGTCTTCCTAC

GCTTCATGTGCCACCACGCCGTGCGCATCAGGGGCAAGTCCTACGTCCAGTGCCAGGGGATCC

CGCAGGGCTCCATCCTCTCCACGCTGCTCTGCAGCCTGTGCTACGGCGACATGGAGAACAAGCT

GTTTGCGGGGATTCGGCGGACGGGCTGCTCCTGCGTTTGGTGGATGATTTCTTGTTGGTGAGA

CCTCACCTCACCCACGCGAAAACCTTCCTCAGGACCCTGGTCCGAGGTGTCCCTGAGTATGGCT

GCGTGGTGAACTTGCGGAAGACAGTGGTGAACTTCCCTGTAGAAGACGAGGCCCTGGGTGGCA

CGGCTTTTGTTCAGATGCCGGCCCACGGCCTATTCCCTGGTGCGGCCTGCTGCTGGATACCCG

GACCCTGGAGGTGCAGAGCGACTACTCCAGCTATGCCCGGACCTCCATCAGAGCCAGTCTCACC

TTCAACCGCGGCTTCAAGGCTGGGAGGAACATGCGTCGCAAACTCTTTGGGGTCTTGCGGCTGA

AGTGTCACAGCCTGTTTCTGGATTTGCAGGTGAACAGCCTCCAGACGGTGTGCACCAACATCTAC

AAGATCCTCCTGCTGCAGGCGTACAGGTTTCACGCATGTGTGCTGCAGCTCCCATTTCATCAGCA

AGTTTGGAAGAACCCCACATTTTTCCTGCGCGTCATCTCTGACACGGCCTCCCTCTGCTACTCCA

TCCTGAAAGCCAAGAACGCAGGGATGTCGCTGGGGGCCAAGGGCGCCGCCGGCCCTCTGCCCT

CCGAGGCCGTGCAGTGGCTGTGCCACCAAGCATTCCTGCTCAAGCTGACTCGACACCGTGTCAC

CTACGTGCCACTCCTGGGGTCACTCAGGACAGCCCAGACGCAGCTGAGTCGGAAGCTCCCGGG

GACGACGCTGACTGCCCTGGAGGCCGCAGCCAACCCGGCACTGCCCTCAGACTTCAAGACCAT

CCTGGACTGAGTCGAAACTCGCGGCCGCCATATGCATCCTAGGCCTATTAATATTCCGGAGTATA

CGTAGCCGGCTAACGTTAACTTGTTTATTGCAGCTTATAATGGTTACAAATAAAGCAATAGCATCA
```

-continued

```
CAAATTTCACAAATAAAGCATTTTTTTCACTGCATTCTAGTTGTGGTTTGTCCAAACTCATCAATGT
ATCTTAACGCGGATCTGGGCGTGGTTAAGGGTGGGAAAGAATATATAAGGTGGGGGTCTTATGTA
GTTTTGTATCTGTTTTGCAGCAGCCGCCGCCGCCATGAGCACCAACTCGTTTGATGGAAGCATTG
TGAGCTCATATTTGACAACGCGCATGCCCCCATGGGCCGGGGTGCGTCAGAATGTGATGGGCTC
CAGCATTGATGGTCGCCCCGTCCTGCCCGCAAACTCTACTACCTTGACCTACGAGACCGTGTCT
GGAACGCCGTTGGAGACTGCAGCCTCCGCCGCCGCTTCAGCCGCTGCAGCCACCGCCCGCGG
GATTGTGACTGACTTTGCTTTCCTGAGCCCGCTTGCAAGCAGTGCAGCTTCCCGTTCATCCGCCC
GCGATGACAAGTTGACGGCTCTTTTGGCACAATTGGATTCTTTGACCCGGGAACTTAATGTCGTT
TCTCAGCAGCTGTTGGATCTGCGCCAGCAGGTTTCTGCCCTGAAGGCTTCCTCCCCTCCCAATG
CGGTTTAAAACATAAATAAAAAACCAGACTCTGTTTGGATTTGGATCAAGCAAGTGTCTTGCTGTC
TTTATTTAGGGGTTTTGCGCGCGCGGTAGGCCCGGGACCAGCGGTCTCGGTCGTTGAGGGTCCT
GTGTATTTTTTCCAGGACGTGGTAAAGGTGACTCTGGATGTTCAGATACATGGGCATAAGCCCGT
CTCTGGGGTGGAGGTAGCACCACTGCAGAGCTTCATGCTGCGGGGTGGTGTTGTAGATGATCCA
GTCGTAGCAGGAGCGCTGGGCGTGGTGCCTAAAAATGTCTTTCAGTAGCAAGCTGATTGCCAGG
GGCAGGCCCTTGGTGTAAGTGTTTACAAAGCGGTTAAGCTGGGATGGGTGCATACGTGGGGATA
TGAGATGCATCTTGGACTGTATTTTTAGGTTGGCTATGTTCCCAGCCATATCCCTCCGGGGATTCA
TGTTGTGCAGAACCACCAGCACAGTGTATCCGGTGCACTTGGGAAATTTGTCATGTAGCTTAGAA
GGAAATGCGTGGAAGAACTTGGAGACGCCCTTGTGACCTCCAAGATTTTCCATGCATTCGTCCAT
AATGATGGCAATGGGCCCACGGGCGGCGGCCTGGGCGAAGATATTTCTGGGATCACTAACGTCA
TAGTTGTGTTCCAGGATGAGATCGTCATAGGCCATTTTTACAAAGCGCGGGCGGAGGGTGCCAG
ACTGCGGTATAATGGTTCCATCCGGCCCAGGGGCGTAGTTACCCTCACAGATTTGCATTTCCCAC
GCTTTGAGTTCAGATGGGGGGATCATGTCTACCTGCGGGGCGATGAAGAAAACGGTTTCCGGGG
TAGGGGAGATCAGCTGGGAAGAAAGCAGGTTCCTGAGCAGCTGCGACTTACCGCAGCCGGTGG
GCCCGTAAATCACACCTATTACCGGGTGCAACTGGTAGTTAAGAGAGCTGCAGCTGCCGTCATC
CCTGAGCAGGGGGGCCACTTCGTTAAGCATGTCCCTGACTCGCATGTTTTCCCTGACCAAATCC
GCCAGAAGGCGCTCGCCGCCCAGCGATAGCAGTTCTTGCAAGGAAGCAAAGTTTTTCAACGGTT
TGAGACCGTCCGCCGTAGGCATGCTTTTGAGCGTTTGACCAAGCAGTTCCAGGCGGTCCCACAG
CTCGGTCACCTGCTCTACGGCATCTCGATCCAGCATATCTCCTCGTTTCGCGGGTTGGGGCGGC
TTTCGCTGTACGGCAGTAGTCGGTGCTCGTCCAGACGGGCCAGGGTCATGTCTTTCCACGGGCG
CAGGGTCCTCGTCAGCGTAGTCTGGGTCACGGTGAAGGGGTGCGCTCCGGGCTGCGCGCTGGC
CAGGGTGCGCTTGAGGCTGGTCCTGCTGGTGCTGAAGCGCTGCCGGTCTTCGCCCTGCGCGTC
GGCCAGGTAGCATTTGACCATGGTGTCATAGTCCAGCCCCTCCGCGGCGTGGCCCTTGGCGCG
CAGCTTGCCCTTGGAGGAGGCGCCGCACGAGGGGCAGTGCAGACTTTTGAGGGCGTAGAGCTT
GGGCGCGAGAAATACCGATTCCGGGGAGTAGGCATCCGCGCCGCAGGCCCCGCAGACGGTCTC
GCATTCCACGAGCCAGGTGAGCTCTGGCCGTTCGGGGTCAAAAACCAGGTTTCCCCCATGCTTT
TTGATGCGTTTCTTACCTCTGGTTTCCATGAGCCGGTGTCCACGCTCGGTGACGAAAAGGCTGTC
CGTGTCGCCGTATACAGACTTGAGAGGCCTGTCCTCGAGCGGTGTTCCGCGGTCCTCCTCGTAT
AGAAACTCGGACCACTCTGAGACAAAGGCTCGCGTCCAGGCCAGCACGAAGGAGGCTAAGTGG
GAGGGGTAGCGGTCGTTGTCCACTAGGGGGTCCACTCGCTCCAGGGTGTGAAGACACATGTCG
CCCTCTTCGGCATCAAGGAAGGTGATTGGTTTGTAGGTGTAGGCCACGTGACCGGGTGTTCCTG
AAGGGGGGCTATAAAAGGGGGTGGGGGCGCGTTCGTCCTCACTCTCTTCCGCATCGCTGTCTGC
```

```
GAGGGCCAGCTGTTGGGGTGAGTACTCCCTCTGAAAAGCGGGCATGACTTCTGCGCTAAGATTG

TCAGTTTCCAAAAACGAGGAGGATTTGATATTCACCTGGCCCGCGGTGATGCCTTTGAGGGTGG

CCGCATCCATCTGGTCAGAAAAGACAATCTTTTTGTTGTCAAGCTTGGTGGCAAACGACCCGTAG

AGGGCGTTGGACAGCAACTTGGCGATGGAGCGCAGGGTTTGGTTTTTGTCGCGATCGGCGCGC

TCCTTGGCCGCGATGTTTAGCTGCACGTATTCGCGCGCAACGCACCGCCATTCGGGAAAGACGG

TGGTGCGCTCGTCGGGCACCAGGTGCACGCGCCAACCGCGGTTGTGCAGGGTGACAAGGTCAA

CGCTGGTGGCTACCTCTCCGCGTAGGCGCTCGTTGGTCCAGCAGAGGCGGCCGCCCTTGCGCG

AGCAGAATGGCGGTAGGGGGTCTAGCTGCGTCTCGTCCGGGGGGTCTGCGTCCACGGTAAAGA

CCCCGGGCAGCAGGCGCGCGTCGAAGTAGTCTATCTTGCATCCTTGCAAGTCTAGCGCCTGCTG

CCATGCGCGGGCGGCAAGCGCGCGCTCGTATGGGTTGAGTGGGGGACCCCATGGCATGGGGT

GGGTGAGCGCGGAGGCGTACATGCCGCAAATGTCGTAAACGTAGAGGGGCTCTCTGAGTATTCC

AAGATATGTAGGGTAGCATCTTCCACCGCGGATGCTGGCGCGCACGTAATCGTATAGTTCGTGC

GAGGGAGCGAGGAGGTCGGGACCGAGGTTGCTACGGGCGGGCTGCTCTGCTCGGAAGACTATC

TGCCTGAAGATGGCATGTGAGTTGGATGATATGGTTGGACGCTGGAAGACGTTGAAGCTGGCGT

CTGTGAGACCTACCGCGTCACGCACGAAGGAGGCGTAGGAGTCGCGCAGCTTGTTGACCAGCT

CGGCGGTGACCTGCACGTCTAGGGCGCAGTAGTCCAGGGTTTCCTTGATGATGTCATACTTATC

CTGTCCCTTTTTTTTCCACAGCTCGCGGTTGAGGACAAACTCTTCGCGGTCTTTCCAGTACTCTTG

GATCGGAAACCCGTCGGCCTCCGAACGGTAAGAGCCTAGCATGTAGAACTGGTTGACGGCCTGG

TAGGCGCAGCATCCCTTTTCTACGGGTAGCGCGTATGCCTGCGCGGCCTTCCGGAGCGAGGTGT

GGGTGAGCGCAAAGGTGTCCCTGACCATGACTTTGAGGTACTGGTATTTGAAGTCAGTGTCGTC

GCATCCGCCCTGCTCCCAGAGCAAAAAGTCCGTGCGCTTTTTGGAACGCGGATTTGGCAGGGCG

AAGGTGACATCGTTGAAGAGTATCTTTCCCGCGCGAGGCATAAAGTTGCGTGTGATGCGGAAGG

GTCCCGGCACCTCGGAACGGTTGTTAATTACCTGGGCGGCGAGCACGATCTCGTCAAAGCCGTT

GATGTTGTGGCCCACAATGTAAAGTTCCAAGAAGCGCGGGATGCCGTTGATGGAAGGCAATTTTT

TAAGTTCCTCGTAGGTGAGCTCTTCAGGGGAGCTGAGCCCGTGCTCTGAAAGGGCCCAGTCTGC

AAGATGAGGGTTGGAAGCGACGAATGAGCTCCACAGGTCACGGGCCATTAGCATTTGCAGGTGG

TCGCGAAAGGTCCTAAACTGGCGACCTATGGCCATTTTTTCTGGGGTGATGCAGTAGAAGGTAAG

CGGGTCTTGTTCCGAGGGGTCCCATCCAAGGTTCGCGGCTAGGTCTCGCGCGGCAGTCACTAGA

GGCTCATCTCCGCCGAACTTCATGACCAGCATGAAGGGCACGAGCTGCTTCCCAAAGGCCCCCA

TCCAAGTATAGGTCTCTACATCGTAGGTGACAAAGAGACGCTCGGTGCGAGGATGCGAGCCGAT

CGGGAAGAACTGGATCTCCCGCCACCAATTGGAGGAGTGGCTATTGATGTGGTGAAAGTAGAAG

TCGCTGCGAGGGGCCGAACACTCGTGCTGGCTTTTGTAAAAACGTGCGCAGTACTGGCAGGGGT

GCACGGGCTGTACATCCTGCACGAGGTTGACCTGACGACCGCGCACAAGGAAGCAGAGTGGGA

ATTTGAGCCCCTCGCCTGGCGGGTTTGGCTGGTGGTCTTCTACTTCGGCTGCTTGTCCTTGACC

GTCTGGCTGCTCGAGGGGAGTTACGGTGGATCGGACCACCACGCCGCGCGAGCCCAAAGTCCA

GATGTCCGCGCGCGGCGGTCGGAGCTTGATGACAACATCGCGCAGATGGGAGCTGTCCATGGT

CTGGAGCTCCCGCGGCGTCAGGTCAGGCGGGAGCTCCTGCAGGTTTACCTCGCATAGACGGGT

CAGGGCGCGGGCTAGATCCAGGTGATACCTAATTTCCAGGGGCTGGTTGGTGGCGGCGTCGAT

GGCTTGCAAGAGGCCGCATCCCCGCGCGCGACTACGGTACCGCGCGGCGGGCGGTGGGCCG

CGGGGGTGTCCTTGGATGATGCATCTAAAAGCGGTGACGCGGGCGAGCCCCCGGAGGTAGGGG
```

-continued

```
GGGCTCCGGACCCGCCGGGAGAGGGGGCAGGGGCACGTCGGCGCCGCGCGCGGGCAGGAGC

TGGTGCTGCGCGCGTAGGTTGCTGGCGAACGCGACGACGCGGCGGTTGATCTCCTGAATCTGG

CGCCTCTGCGTGAAGACGACGGGCCCGGTGAGCTTGAGCCTGAAAGAGAGTTCGACAGAATCAA

TTTCGGTGTCGTTGACGGCGGCCTGGCGCAAAATCTCCTGCACGTCTCCTGAGTTGTCTTGATAG

GCGATCTCGGCCATGAACTGCTCGATCTCTTCCTCCTGGAGATCTCCGCGTCCGGCTCGCTCCA

CGGTGGCGGCGAGGTCGTTGGAAATGCGGGCCATGAGCTGCGAGAAGGCGTTGAGGCCTCCCT

CGTTCCAGACGCGGCTGTAGACCACGCCCCCTTCGGCATCGCGGGCGCGCATGACCACCTGCG

CGAGATTGAGCTCCACGTGCCGGGCGAAGACGGCGTAGTTTCGCAGGCGCTGAAAGAGGTAGT

TGAGGGTGGTGGCGGTGTGTTCTGCCACGAAGAAGTACATAACCCAGCGTCGCAACGTGGATTC

GTTGATATCCCCCAAGGCCTCAAGGCGCTCCATGGCCTCGTAGAAGTCCACGGCGAAGTTGAAA

AACTGGGAGTTGCGCGCCGACACGGTTAACTCCTCCTCCAGAAGACGGATGAGCTCGGCGACA

GTGTCGCGCACCTCGCGCTCAAAGGCTACAGGGGCCTCTTCTTCTTCTTCAATCTCCTCTTCCAT

AAGGGCCTCGCCTTCTTCTTCTTCTGGCGGCGGTGGGGGAGGGGGACAGGGCGGCGAGGAC

GGCGCACCGGGAGGCGGTCGACAAAGCGCTCGATCATCTCCCCGCGGCGACGGCGCATGGTCT

CGGTGACGGCGCGGCCGTTCTCGCGGGGGCGCAGTTGGAAGACGCCGCCCGTCATGTCCCGG

TTATGGGTTGGCGGGGGGCTGCCATGCGGCAGGGATACGGCGCTAACGATGCATCTCAACAATT

GTTGTGTAGGTACTCCGCCGCCGAGGGACCTGAGCGAGTCCGCATCGACCGGATCGGAAAACC

TCTCGAGAAAGGCGTCTAACCAGTCACAGTCGCAAGGTAGGCTGAGCACCGTGGCGGGCGGCA

GCGGGCGGCGGTCGGGGTTGTTTCTGGCGGAGGTGCTGCTGATGATGTAATTAAAGTAGGCGG

TCTTGAGACGGCGGATGGTCGACAGAAGCACCATGTCCTTGGGTCCGGCCTGCTGAATGCGCAG

GCGGTCGGCCATGCCCCAGGCTTCGTTTTGACATCGGCGCAGGTCTTTGTAGTAGTCTTGCATG

AGCCTTTCTACCGGCACTTCTTCTTCTCCTTCCTCTTGTCCTGCATCTCTTGCATCTATCGCTGCG

GCGGCGGCGGAGTTTGGCCGTAGGTGGCGCCCTCTTCCTCCCATGCGTGTGACCCCGAAGCCC

CTCATCGGCTGAAGCAGGGCTAGGTCGGCGACAACGCGCTCGGCTAATATGGCCTGCTGCACCT

GCGTGAGGGTAGACTGGAAGTCATCCATGTCCACAAAGCGGTGGTATGCGCCCGTGTTGATGGT

GTAAGTGCAGTTGGCCATAACGGACCAGTTAACGGTCTGGTGACCCGGCTGCGAGAGCTCGGTG

TACCTGAGACGCGAGTAAGCCCTCGAGTCAAATACGTAGTCGTTGCAAGTCCGCACCAGGTACT

GGTATCCCACCAAAAAGTGCGGCGGCGGCTGGCGGTAGAGGGGCCAGCGTAGGGTGGCCGGG

GCTCCGGGGCGAGATCTTCCAACATAAGGCGATGATATCCGTAGATGTACCTGGACATCCAGG

TGATGCCGGCGGCGGTGGTGGAGGCGCGCGGAAAGTCGCGGACGCGGTTCCAGATGTTGCGC

AGCGGCAAAAAGTGCTCCATGGTCGGGACGCTCTGGCCGGTCAGGCGCGCGCAATCGTTGACG

CTCTACCGTGCAAAAGGAGAGCCTGTAAGCGGGCACTCTTCCGTGGTCTGGTGGATAAATTCGC

AAGGGTATCATGGCGGACGACCGGGGTTCGAGCCCCGTATCCGGCCGTCCGCCGTGATCCATG

CGGTTACCGCCCGCGTGTCGAACCCAGGTGTGCGACGTCAGACAACGGGGGAGTGCTCCTTTT

GGCTTCCTTCCAGGCGCGGCGGCTGCTGCGCTAGCTTTTTTGGCCACTGGCCGCGCGCAGCGT

AAGCGGTTAGGCTGGAAAGCGAAAGCATTAAGTGGCTCGCTCCCTGTAGCCGGAGGGTTATTTT

CCAAGGGTTGAGTCGCGGGACCCCCGGTTCGAGTCTCGGACCGGCCGGACTGCGGCGAACGG

GGGTTTGCCTCCCCGTCATGCAAGACCCCGCTTGCAAATTCCTCCGGAAACAGGGACGAGCCCC

TTTTTTGCTTTTCCCAGATGCATCCGGTGCTGCGGCAGATGCGCCCCCCTCCTCAGCAGCGGCA

AGAGCAAGAGCAGCGGCAGACATGCAGGGCACCCTCCCCTCCTCCTACCGCGTCAGGAGGGGC

GACATCCGCGGTTGACGCGGCAGCAGATGGTGATTACGAACCCCCGCGGCGCCGGGCCCGGC
```

-continued

```
ACTACCTGGACTTGGAGGAGGGCGAGGGCCTGGCGCGGCTAGGAGCGCCCTCTCCTGAGCGGT
ACCCAAGGGTGCAGCTGAAGCGTGATACGCGTGAGGCGTACGTGCCGCGGCAGAACCTGTTTC
GCGACCGCGAGGGAGAGGAGCCCGAGGAGATGCGGGATCGAAAGTTCCACGCAGGGCGCGAG
CTGCGGCATGGCCTGAATCGCGAGCGGTTGCTGCGCGAGGAGGACTTTGAGCCCGACGCGCGA
ACCGGGATTAGTCCCGCGCGCACACGTGGCGGCCGCCGACCTGGTAACCGCATACGAGCAG
ACGGTGAACCAGGAGATTAACTTTCAAAAAAGCTTTAACAACCACGTGCGTACGCTTGTGGCGCG
CGAGGAGGTGGCTATAGGACTGATGCATCTGTGGGACTTTGTAAGCGCGCTGGAGCAAAACCCA
AATAGGAAGCCGCTCATGGCGCAGCTGTTCCTTATAGTGCAGCACAGCAGGGACAACGAGGCAT
TCAGGGATGCGCTGCTAAACATAGTAGAGCCCGAGGGCCGCTGGCTGCTCGATTTGATAAACAT
CCTGCAGAGCATAGTGGTGCAGGAGCGCAGCTTGAGCCTGGCTGACAAGGTGGCCGCCATCAA
CTATTCCATGCTTAGCCTGGGCAAGTTTTACGCCCGCAAGATATACCATACCCCTTACGTTCCCAT
AGACAAGGAGGTAAAGATCGAGGGGTTCTACATGCGCATGGCGCTGAAGGTGCTTACCTTGAGC
GACGACCTGGGCGTTTATCGCAACGAGCGCATCCACAAGGCCGTGAGCGTGAGCCGGCGGCGC
GAGCTCAGCGACCGCGAGCTGATGCACAGCCTGCAAAGGGCCCTGGCTGGCACGGGCAGCGG
CGATAGAGAGGCCGAGTCCTACTTTGACGCGGGCGCTGACCTGCGCTGGGCCCCAAGCCGAGG
CGCCCTGGAGGCAGCTGGGGCCGGACCTGGGCTGGCGGTGGCACCCGCGCGCGCTGGCAACG
TCGGCGGCGTGGAGGAATATGACGAGGACGATGAGTACGAGCCAGAGGACGGCGAGTACTAAG
CGGTGATGTTTCTGATCAGATGATGCAAGACGCAACGGACCCGGCGGTGCGGGCGGCGCTGCA
GAGCCAGCCGTCCGGCCTTAACTCCACGGACGACTGGCGCCAGGTCATGGACCGCATCATGTC
GCTGACTGCGCGCAATCCTGACGCGTTCCGGCAGCAGCCGCAGGCCAACCGGCTCTCCGCAAT
TCTGGAAGCGGTGGTCCCGGCGCGCGCAAACCCCACGCACGAGAAGGTGCTGGCGATCGTAAA
CGCGCTGGCCGAAAACAGGGCCATCCGGCCCGACGAGGCCGGCCTGGTCTACGACGCGCTGC
TTCAGGGCGTGGCTCGTTACAACAGCGGCAAGGTGCAGACCAACCTGGACCGGCTGGTGGGGG
ATGTGCGCGAGGCCGTGGCGCAGCGTGAGCGCGCGCAGCAGCAGGGCAACCTGGGCTCCATG
GTTGCACTAAACGCCTTCCTGAGTACACAGCCCGCCAACGTGCCGCGGGGACAGGAGGACTACA
CCAACTTTGTGAGCGCACTGCGGCTAATGGTGACTGAGACACCGCAAAGTGAGGTGTACCAGTC
TGGGCCAGACTATTTTTTCCAGACCAGTAGACAAGGCCTGCAGACCGTAAACCTGAGCCAGGCTT
TCAAAAACTTGCAGGGGCTGTGGGGGGTGCGGGCTCCCACAGGCGACCGCGCGACCGTGTCTA
GCTTGCTGACGCCCAACTCGCGCCTGTTGCTGCTGCTAATAGCGCCCTTCACGGACAGTGGCAG
CGTGTCCCGGGACACATACCTAGGTCACTTGCTGACACTGTACCGCGAGGCCATAGGTCAGGCG
CATGTGGACGAGCATACTTTCCAGGAGATTACAAGTGTCAGCCGCGCGCTGGGGCAGGAGGACA
CGGGCAGCCTGGAGGCAACCCTAAACTACCTGCTGACCAACCGGCGGCAGAAGATCCCCTCGTT
GCACAGTTTAAACAGCGAGGAGGAGCGCATTTTGCGCTACGTGCAGCAGAGCGTGAGCCTTAAC
CTGATGCGCGACGGGGTAACGCCCAGCGTGGCGCTGGACATGACCGCGCGCAACATGGAACCG
GGCATGTATGCCTCAAACCGGCCGTTTATCAACCGCCTAATGGACTACTTGCATCGCGCGGCCG
CCGTGAACCCCGAGTATTTCACCAATGCCATCTTGAACCCGCACTGGCTACCGCCCCCTGGTTTC
TACACCGGGGGATTCGAGGTGCCCGAGGGTAACGATGGATTCCTCTGGGACGACATAGACGACA
GCGTGTTTTCCCCGCAACCGCAGACCCTGCTAGAGTTGCAACAGCGCGAGCAGGCAGAGGCGG
CGCTGCGAAAGGAAAGCTTCCGCAGGCCAAGCAGCTTGTCCGATCTAGGCGCTGCGGCCCCGC
GGTCAGATGCTAGTAGCCCATTTCCAAGCTTGATAGGGTCTCTTACCAGCACTCGCACCACCCGC
```

-continued

```
CCGCGCCTGCTGGGCGAGGAGGAGTACCTAAACAACTCGCTGCTGCAGCCGCAGCGCGAAAAA

AACCTGCCTCCGGCATTTCCCAACAACGGGATAGAGAGCCTAGTGGACAAGATGAGTAGATGGA

AGACGTACGCGCAGGAGCACAGGGACGTGCCAGGCCCGCGCCCGCCCACCCGTCGTCAAAGG

CACGACCGTCAGCGGGGTCTGGTGTGGGAGGACGATGACTCGGCAGACGACAGCAGCGTCCTG

GATTTGGGAGGGAGTGGCAACCCGTTTGCGCACCTTCGCCCCAGGCTGGGGAGAATGTTTTAAA

AAAAAAAAGCATGATGCAAAATAAAAAACTCACCAAGGCCATGGCACCGAGCGTTGGTTTTCTT

GTATTCCCCTTAGTATGCGGCGCGCGGCGATGTATGAGGAAGGTCCTCCTCCCTCCTACGAGAG

TGTGGTGAGCGCGGCGCCAGTGGCGGCGGCGCTGGGTTCTCCCTTCGATGCTCCCCTGGACCC

GCCGTTTGTGCCTCCGCGGTACCTGCGGCCTACCGGGGGAGAAACAGCATCCGTTACTCTGA

GTTGGCACCCCTATTCGACACCACCCGTGTGTACCTGGTGGACAACAAGTCAACGGATGTGGCA

TCGCTGAACTACCAGAACGACCACAGGAACTTTCTGACCAGGGTCATTGAAAACAATGACTACAG

CCCGGGGAGGCAAGCACACAGACCATCAATCTTGACGACCGGTCGCACTGGGGCGGCGACCT

GAAAACCATCCTGCATACCAACATGCCAAATGTGAACGAGTTCATGTTTACCAATAAGTTTAAGGC

GCGGGTGATGGTGTCGCGCTTGCCTACTAAGGACAATCAGGTGGAGCTGAAATACGAGTGGGTG

GAGTTGAGGCTGCCCGAGGGCAACTACTCCGAGACCATGACCATAGACCTTATGAACAACGCGA

TCGTGGAGCACTACTTGAAAGTGGGCAGACAGAACGGGGTTCTGGAAAGCGACATCGGGGTAAA

GTTTGACACCCGCAACTTCAGACTGGGGTTTGACCCCGTCACTGGTCTTGTCATGCCTGGGGTAT

ATACAAACGAAGCCTTCCATCCAGACATCATTTTGCTGCCAGGATGCGGGGTGGACTTCACCCAC

AGCCGCCTGAGGAACTTGTTGGGCATCCGCAAGGGGCAACCCTTCCAGGAGGGCTTTAGGATCA

CCTACGATGATCTGGAGGGTGGTAACATTCCCGCACTGTTGGATGTGGACGCCTACCAGGCGAG

CTTGAAAGATGACACCGAACAGGGCGGGGGTGGCGCAGGCGGCAGCAACAGCAGTGGCAGCG

GCGCGGAAGAGAACTCCAACGCGGCAGCCGCGGCAATGCAGCCGGTGGAGGACATGAACGATC

ATGCCATTCGCGGCGAGACCTTTGCCAGAGGGGCTGAGGAGAAGCGCGCTGAGGCCGAAGGAG

CGGCCGAAGCTGCCGCCCCCGCTGCGCAACCCGAGGTCGAGAAGCCTCAGAAGAAACCGGTGA

TCAAACCCCTGACAGAGGACAGCAAGAAACGCAGTTACAACCCTAATAAGCAATGACAGCACCTTC

ACCCAGTACCGCAGCTGGTACCTTGCATACAACTACGGCGACCCTCAGACCGGAATCCGCTCAT

GGACCCTGCTTTGCACTCCTGACGTAACCTGCGGCTCGGAGCAGGTCTACTGGTCGTTGCCAGA

CATGATGCAAGACCCCGTGACCTTCCGCTCCACGCGCCAGATCAGCAACTTTCCGGTGGTGGGC

GCCGAGCTGTTGCCCGTGCACTCCAAGAGCTTCTACAACGACCAGGCCGTCTACTCCCAACTCA

TCCGCCAGTTTACCTCTCTGACCCACGTGTTCAATCGCTTTCCCGAGAACCAGATTTTGGCGCGC

CCGCCAGCCCCCACCATCACCACCGTCAGTGAAAACGTTCCTGCTCTCACAGATCACGGGACGC

TACCGCTGCGCAACAGCATCGGAGGAGTCCAGCGAGTGACCATTACTGACGCCAGACGCCGCA

CCTGCCCCTACGTTTACAAGGCCCTGGGCATAGTCTCGCCGCGCGTCCTATCGAGCCGCACTTT

TTGAGCAAGCATGTCCATCCTTATATCGCCCAGCAATAACACAGGCTGGGGCCTGCGCTTCCCAA

GCAAGATGTTTGGCGGGGCCAAGAAGCGCTCCGACCAACACCCAGTGCGCGTGCGCGGGCACT

ACCGCGCGCCCTGGGGCGCGCACAAACGCGGCCGCACTGGGCGCACCACCGTCGATGACGCC

ATCGACGCGGTGGTGGAGGAGGCGCGCAACTACACGCCCACGCCGCCACCAGTGTCCACAGTG

GACGCGGCCATTCAGACCGTGGTGCGCGGAGCCCGGCGCTATGCTAAAATGAAGAGACGGCGG

AGGCGCGTAGCACGTCGCCACCGCCGCCGACCCGGCACTGCCGCCCAACGCGCGGCGGCGGC

CCTGCTTAACCGCGCACGTCGCACCGGCCGAGGGGCGGCCATGCGGGCCGCTCGAAGGCTGG

CCGCGGGTATTGTCACTGTGCCCCCCAGGTCCAGGCGACGAGCGGCCGCCGCAGCAGCCGCG
```

-continued

```
GCCATTAGTGCTATGACTCAGGGTCGCAGGGGCAACGTGTATTGGGTGCGCGACTCGGTTAGCG

GCCTGCGCGTGCCCGTGCGCACCCGCCCGCCGCGCAACTAGATTGCAAGAAAAAACTACTTAGA

CTCGTACTGTTGTATGTATCCAGCGGCGGCGGCGCGCAACGAAGCTATGTCCAAGCGCAAAATC

AAAGAAGAGATGCTCCAGGTCATCGCGCCGGAGATCTATGGCCCCCCGAAGAAGGAAGAGCAG

GATTACAAGCCCCGAAAGCTAAAGCGGGTCAAAAAGAAAAAGAAAGATGATGATGATGAACTTGA

CGAGGAGGTGGAACTGCTGCAGGCTACCGCGCCCAGGCGAGGGGTAGAGTGGAAAGGTCGAGG

CGTAAAACGTGTTTTGCGACCCGGCACCACCGTAGTCTTTACGCCCGGTGAGCGCTCCACCCGC

ACCTACAAGCGCGTGTATGATGAGGTGTACGGCGACGAGGACCTGCTTGAGCAGGCCAACGAG

CGCCTCGGGGAGTTTGCCTACGGAAAGCGGCATAAGGACATGCTGGCGTTGCCGCTGGACGAG

GGCAACCCAACACCTAGGCTAAAGCCCGTAACACTGCAGGAGGTGCTGCCCGCGCTTGCACCGT

CCGAAGAAAAGCGCGGCCTAAAGCGCGAGTCTGGTGACTTGGCACCCACCGTGCAGCTGATGG

TACCCAAGCGCCAGCGACTGGAAGATGTCTTGGAAAAAATGACCGTGGAACCTGGGCTGGAGCC

CGAGGTCCGCGTGCGGCCAATCAAGCAGGTGGCGCCGGGACTGGGCGTGCAGACCGTGGACG

TTCAGATACCCACTACCAGTAGGACCAGTATTGCCACCGCCACAGAGGGCATGGAGACACAAAC

GTCCCCGGTTGCCTCAGCGGTGGCGGATGCCGCGGTGCAGGCGGTCGCTGCGGCCGCGTCCA

AGACCTCTACGGAGGTGCAAACGGACCCGTGGATGTTTCGCGTTTCAGCCCCCCGGCGCCCGC

GCGGTTCGAGGAAGTACGGCGCCGCCAGCGCGCTACTGCCCGAATATGCCCTACATCCTTCCAT

TGCGCCTACCCGCGGCTATCGTGGCTACACCTACCGCCCCAGAAGAGGAGGAACTACCCGACGC

CGAACCACCACTGGAACCCGCCGCCGCCGTCGCCGTCGCCAGCCCGTGCTGGCCCCGATTTCC

GTGCGCAGGGTGGCTCGCGAAGGAGGCAGGACCCTGGTGCTGCCAACAGCGCGCTACCACCC

CAGCATCGTTTAAAAGCCGGTCTTTGTGGTTCTTGCAGATATGGCCCTCACCTGCCGCCTCCGTT

TCCCGGTGCCGGGATTCCGAGGAAGAATGCACCGTAGGAGGGGCATGGCCGGCCACGGCCTGA

CGGGCGGCATGCGTCGTGCGCACCACCGGCGGCGGCGCGCGTCGCACCGTCGCATGCGCGGC

GGTATCCTGCCCCTCCTTATTCCACTGATCGCCGCGGCGATTGGCGCCGTGCCCGGAATTGCAT

CCGTGGCCTTGCAGGCGCAGAGACACTGATTAAAAACAAGTTGCATGTGGAAAAATCAAATAAA

AAGTCTGGACTCTCACGCTCGCTTGGTCCTGTAACTATTTTGTAGAATGGAAGACATCAACTTTGC

GTCTCTGGCCCCGCGACACGGCTCGCGCCCGTTCATGGGAAACTGGCAAGATATCGGCACCAG

CAATATGAGCGGTGGCGCCTTCAGCTGGGGCTCGCTGTGGAGCGGCATTAAAAATTTCGGTTCC

ACCGTTAAGAACTATGGCAGCAAGGCCTGGAACAGCAGCACAGGCCAGATGCTGAGGGATAAGT

TGAAAGAGCAAAATTTCCAACAAAAGGTGGTAGATGGCCTGGCCTCTGGCATTAGCGGGGTGGT

GGACCTGGCCAACCAGGCAGTGCAAAATAAGATTAACAGTAAGCTTGATCCCCGCCCTCCCGTA

GAGGAGCCTCCACCGGCCGTGGAGACAGTGTCTCCAGAGGGGCGTGGCGAAAAGCGTCCGCG

CCCCGACAGGGAAGAAACTCTGGTGACGCAAATAGACGAGCCTCCCTCGTACGAGGAGGCACTA

AAGCAAGGCCTGCCCACCACCCGTCCCATCGCGCCCATGGCTACCGGAGTGCTGGGCCAGCAC

ACACCCGTAACGCTGGACCTGCCTCCGCCCGCCGAGACCCAGGAGAAACCTGTGCTGCCAGGC

CCGACCGCCGTTGTTGTAACCCGTCCTAGCCGCGCGTCCCTGCGCCGCGCCGCCAGCGGTCCG

CGATCGTTGCGGCCCGTAGCCAGTGGCAACTGGCAAAGCACACTGAACAGCATCGTGGGTCTG

GGGGTGCAATCCCTGAAGCGCCGACGATGCTTCTGAATAGCTAACGTGTCGTATGTGTGTCATGT

ATGCGTCCATGTCGCCGCCAGAGGAGCTGCTGAGCCGCCGCGCGCCCGCTTTCCAAGATGGCT

ACCCCTTCGATGATGCCGCAGTGGTCTTACATGCACATCTCGGGCCAGGACGCCTCGGAGTACC
```

-continued

```
TGAGCCCCGGGCTGGTGCAGTTTGCCCGCGCCACCGAGACGTACTTCAGCCTGAATAACAAGTT

TAGAAACCCCACGGTGGCGCCTACGCACGACGTGACCACAGACCGGTCCGAGGGTTTGAGGCT

GCGGTTCATCCCTGTGGACCGTGAGGATACTGCGTACTCGTACAAGGCGCGGTTCACCCTAGCT

GTGGGTGATAACCGTGTGCTGGACATGGCTTCCACGTACTTTGACATCCGCGGCGTGCTGGACA

GGGGCCCTACTTTTAAGCCCTACTCTGGCACTGCCTACAACGCCCTGGCTCCCAAGGGTGCCCC

AAATCCTTGCGAATGGGATGAAGCTGCTACTGCTCTTGAAATAAACCTAGAAGAAGAGGAGGATG

ACAACGAAGACGAAGTAGACGAGCAAGCTGAGCAGCAAAAAACTCACGTATTTGGGCAGGCGCC

TTATTCTGGTATAAATATTACAAAGGAGGGTATTCAAATAGGTGTCGAAGGTCAAACACCTAAATA

TGCCGATAAAACATTTCAACCTGAACCTCAAATAGGAGAATCTCAGTGGTACGAAACTGAAATTAA

TCATGCAGCTGGGAGAGTCCTTAAAAAGACTACCCCAATGAAACCATGTTAGGGTTCATATGCAA

AACCCACAAATGAAATGGAGGGCAAGGCATTCTTGTAAAGCAACAAAATGGAAAGCTAGAAAGT

CAAGTGGAAATGCAATTTTTCTCAACTACTGAGGCGACCGCAGGCAATGGTGATAACTTGACTCC

TAAAGTGGTATTGTACAGTGAAGATGTAGATATAGAAACCCCAGACACTCATATTTCTTACATGCC

CACTATTAAGGAAGGTAACTGAGGAGAACTAATGGGCCAACAATCTATGCCCAACAGGCCTAATT

ACATTGCTTTTAGGGACAATTTTATTGGTCTAATGTATTACAACAGCACGGGTAATATGGGTGTTC

TGGCGGGCCAAGCATCGCAGTTGAATGCTGTTGTAGATTTGCAAGACAGAAACACAGAGCTTTCA

TACCAGCTTTTGCTTGATTCCATTGGTGATAGAACCAGGTACTTTTCTATGTGGAATCAGGCTGTT

GACAGCTATGATCCAGATGTTAGAATTATTGAAAATCATGGAACTGAAGATGAACTTCCAAATTAC

TGCTTTCCACTGGGAGGTGTGATTAATACAGAGACTCTTACCAAGGTAAAACCTAAAACAGGTCA

GGAAAATGGATGGGAAAAAGATGCTACAGAATTTTCAGATAAAAATGAAATAAGAGTTGGAAATAA

TTTTGCCATGGAAATCAATCTAAATGCCAACCTGTGGAGAAATTTCCTGTACTCCAACATAGCGCT

GTATTTGCCCGACAAGCTAAAGTACAGTCCTTCCAACGTAAAAATTTCTGATAACCCAAACACCTA

CGACTACATGAACAAGCGAGTGGTGGCTCCCGGGTTAGTGGACTGCTACATTAACCTTGGAGCA

CGCTGGTCCCTTGACTATATGGACAACGTCAACCCATTTAACCACCACCGCAATGCTGGCCTGCG

CTACCGCTCAATGTTGCTGGGCAATGGTCGCTATGTGCCCTTCCACATCCAGGTGCCTCAGAAGT

TCTTTGCCATTAAAAACCTCCTTCTCCTGCCGGGCTCATACACCTACGAGTGGAACTTCAGGAAG

GATGTTAACATGGTTCTGCAGAGCTCCCTAGGAAATGACCTAAGGGTTGAGGGAGCCAGGATTAA

GTTTGATAGCATTTGCCTTTACGCCACCTTCTTCCCCATGGCCCACAACACCGCCTCCACGCTTG

AGGCCATGCTTAGAAACGACACCAACGACCAGTCCTTTAACGACTATCTCTCCGCCGCCAACATG

CTCTACCCTATACCCGCCAACGCTACCAACGTGCCCATATCCATCCCTCCCGCAACTGGGCGG

CTTTCCGCGGCTGGGCCTTGAGGCGCCTTAAGACTAAGGAAACCCCATCACTGGGCTCGGGCTA

CGACCCTTATTACACCTACTCTGGCTCTATACCCTACCTAGATGGAACCTTTTACCTCAACCACAC

CTTTAAGAAGGTGGCCATTACCTTTGACTCTTCTGTCAGCTGGCCTGGCAATGACCGCCTGCTTA

CCCCCAACGAGTTTGAAATTAAGCGCTCAGTTGACGGGGAGGGTTACAACGTTGCCCAGTGTAA

CATGACCAAAGACTGGTTCCTGGTACAAATGCTAGCTAACTACAACATTGGCTACCAGGGCTTCT

ATATCCCAGAGAGCTACAAGGACCGCATGTACTCCTTCTTTAGAAACTTCCAGCCCATGAGCCGT

CAGGTGGTGGATGATACTAAATACAAGGACTACCAACAGGTGGGCATCCTACACCAACACAACAA

CTCTGGATTTGTTGGCTACCTTGCCCCCACCATGCGCGAAGGACAGGCCTACCCTGCTAACTTCC

CCTATCCGCTTATAGGCAAGACCGCAGTTGACAGCATTACCCAGAAAAAGTTTCTTTGCGATCGC

ACCCTTTGGCGCATCCCATTCTCCAGTAACTTTATGTCCATGGGCGCACTCACAGACCTGGGCCA

AAACCTTCTCTACGCCAACTCCGCCCACGCGCTAGACATGACTTTTGAGGTGGATCCCATGGACG
```

-continued

```
AGCCCACCCTTCTTTATGTTTTGTTTGAAGTCTTTGACGTGGTCCGTGTGCACCGGCCGCACCGC
GGCGTCATCGAAACCGTGTACCTGCGCACGCCCTTCTCGGCCGGCAACGCCACAACATAAAGAA
GCAAGCAACATCAACAACAGCTGCCGCCATGGGCTCCAGTGAGCAGGAACTGAAAGCCATTGTC
AAAGATCTTGGTTGTGGGCCATATTTTTTGGGCACCTATGACAAGCGCTTTCCAGGCTTTGTTTCT
CCACACAAGCTCGCCTGCGCCATAGTCAATACGGCCGGTCGCGAGACTGGGGGCGTACACTGG
ATGGCCTTTGCCTGGAACCCGCACTCAAAAACATGCTACCTCTTTGAGCCCTTTGGCTTTTCTGA
CCAGCGACTCAAGCAGGTTTACCAGTTTGAGTACGAGTCACTCCTGCGCCGTAGCGCCATTGCTT
CTTCCCCCGACCGCTGTATAACGCTGGAAAAGTCCACCCAAAGCGTACAGGGGCCCAACTCGGC
CGCCTGTGGACTATTCTGCTGCATGTTTCTCCAGGCCTTTGCCAACTGGCCCCAAACTCCCATGG
ATCACAACCCCACCATGAACCTTATTACCGGGGTACCCAACTCCATGCTCAACAGTCCCCAGGTA
CAGCCCACCCTGCGTCGCAACCAGGAACAGCTCTACAGCTTCCTGGAGCGCCACTCGCCCTACT
TCCGCAGCCACAGTGCGCAGATTAGGAGCGCCACTTCTTTTTGTCACTTGAAAAACATGTAAAAA
TAATGTACTAGAGACACTTTCAATAAAGGCAAATGCTTTTATTTGTACACTCTCGGGTGATTATTTA
CCCCCACCCTTGCCGTCTGCGCCGTTTAAAAATCAAAGGGGTTCTGCCGCGCATCGCTATGCGC
CACTGGCAGGGACACGTTGCGATACTGGTGTTTAGTGCTCCACTTAAACTCAGGCACAACCATCC
GCGGCAGCTCGGTGAAGTTTTCACTCCACAGGCTGCGCACCATCACCAACGCGTTTAGCAGGTC
GGGCGCCGATATCTTGAAGTCGCAGTTGGGGCCTCCGCCCTGCGCGCGCGAGTTGCGATACAC
AGGGTTGCAGCACTGGAACACTATCAGCGCCGGGTGGTGCACGCTGGCCAGCACGCTCTTGTC
GGAGATCAGATCCGCGTCCAGGTCCTCCGCGTTGCTCAGGGCGAACGGAGTCAACTTTGGTAGC
TGCCTTCCCAAAAAGGGCGCGTGCCCAGGCTTTGAGTTGCACTCGCACCGTAGTGGCATCAAAA
GGTGACCGTGCCCGGTCTGGGCGTTAGGATACAGCGCCTGCATAAAAGCCTTGATCTGCTTAAA
AGCCACCTGAGCCTTTGCGCCTTCAGAGAAGAACATGCCGCAAGACTTGCCGGAAAACTGATTG
GCCGGACAGGCCGCGTCGTGCACGCAGCACCTTGCGTCGGTGTTGGAGATCTGCACCACATTTC
GGCCCCACCGGTTCTTCACGATCTTGGCCTTGCTAGACTGCTCCTTCAGCGCGCGCTGCCCGTT
TTCGCTCGTCACATCCATTTCAATCACGTGCTCCTTATTTATCATAATGCTTCCGTGTAGACACTTA
AGCTCGCCTTCGATCTCAGCGCAGGGGTGCAGCCACAAGGCGCAGCCCGTGGGCTCGTGATGC
TTGTAGGTCACCTCTGCAAACGACTGCAGGTACGCCTGCAGGAATCGCCCCATCATCGTCACAAA
GGTCTTGTTGCTGGTGAAGGTCAGCTGCAACCCGCGGTGCTCCTCGTTCAGCCAGGTCTTGCAT
ACGGCCGCCAGAGCTTCCACTTGGTCAGGCAGTAGTTTGAAGTTCGCCTTTAGATCGTTATCCAC
GTGGTACTTGTCCATCAGCGCGCGCAGCCTCCATGCCCTTCTCCCACGCAGACACGATCGGC
ACACTCAGCGGGTTCATCACCGTAATTTCACTTTCCGCTTCGCTGGGCTCTTCCTCTTCCTCTTGC
GTCCGCATACCACGCGCCACTGGGTCGTCTTCATTCAGCCGCCGCACTGTGCGCTTACCTCCTT
TGCCATGCTTGATTAGCACCGGTGGGTTGCTGAAACCCACCATTTGTAGCGCCACATCTTCTCTT
TCTTCCTCGCTGTCCACGATTACCTCTGGTGATGGCGGGCGCTCGGGCTTGGGAGAAGGGCGCT
TCTTTTTCTTCTTGGGCGCAATGGCCAAATCCGCCGCCGAGGTCGATGGCCGCGGGCTGGGTGT
GCGCGGCACCAGCGCGTCTTGTGATGAGTCTTCCTCGTCCTCGGACTCGATACGCCGCCTCATC
CGCTTTTTTGGGGGCGCCCGGGGAGGCGGCGGCGACGGGGACGGGGACGACACGTCCTCCAT
GGTTGGGGGACGTCGCGCCGCACCGCGTCCGCGCTCGGGGGTGGTTTCGCGCTGCTCCTCTTC
CCGACTGGCCATTTCCTTCTCCTATAGGCAGAAAAAGATCATGGAGTCAGTCGAGAAGAAGGACA
GCCTAACCGCCCCCTCTGAGTTCGCCACCACCGCCTCCACCGATGCCGCCAACGCGCCTACCAC
```

-continued

```
CTTCCGCGTCGAGGCACCCCCGCTTGAGGAGGAGGAAGTGATTATCGAGCAGGACCCAGGTTTT

GTAAGCGAAGACGACGAGGACCGCTCAGTACCAACAGAGGATAAAAAGCAAGACCAGGACAACG

CAGAGGCAAACGAGGAACAAGTCGGGCGGGGGGACGAAAGGCATGGCGACTACCTAGATGTGG

GAGACGACGTGCTGTTGAAGCATCTGCAGCGCCAGTGCGCCATTATCTGCGACGCGTTGCAAGA

GCGCAGCGATGTGCCCCTCGCCATAGCGGATGTGAGCCTTGCCTACGAACGCCACCTATTCTCA

CCGCGCGTACCCCCAAACGCCAAGAAAACGGCACATGCGAGCCCAACCCGCGCCTCAACTTCT

ACCCCGTATTTGCCGTGCCAGAGGTGCTTGCCACCTATCACATCTTTTTCCAAAACTGCAAGATA

CCCCTATCCTGCCGTGCCAACCGCAGCCGAGCGGACAAGCAGCTGGCCTTGCGGCAGGGCGCT

GTCATACCTGATATCGCCTCGCTCAACGAAGTGCCAAAAATCTTTGAGGGTCTTGGACGCGACGA

GAAGCGCGCGGCAAACGCTCTGCAACAGGAAAACAGCGAAAATGAAAGTCACTCTGGAGTGTTG

GTGGAACTCGAGGGTGACAACGCGCGCCTAGCCGTACTAAAACGCAGCATCGAGGTCACCCACT

TTGCCTACCCGGCACTTAACCTACCCCCCAAGGTCATGAGCACAGTCATGAGTGAGCTGATCGT

GCGCCGTGCGCAGCCCTGGAGAGGGATGCAAATTTGCAAGAACAAACAGAGGAGGGCCTACC

CGCAGTTGGCGACGAGCAGCTAGCGCGCTGGCTTCAAACGCGCGAGCCTGCCGACTTGGAGGA

GCGACGCAAACTAATGATGGCCGCAGTGCTCGTTACCGTGGAGCTTGAGTGCATGCAGCGGTTC

TTTGCTGACCCGGAGATGCAGCGCAAGCTAGAGGAAACATTGCACTACACCTTTCGACAGGGCT

ACGTACGCCAGGCCTGCAAGATCTCCAACGTGGAGCTCTGCAACCTGGTCTCCTACCTTGGAATT

TTGCACGAAAACCGCCTTGGGCAAAACGTGCTTCATTCCACGCTCAAGGGCGAGGCGCGCCGC

GACTACGTCCGCGACTGCGTTTACTTATTTCTATGCTACACCTGGCAGACGGCCATGGGCGTTTG

GCAGCAGTGCTTGGAGGAGTGCAACCTCAAGGAGCTGCAGAAACTGCTAAAGCAAAACTTGAAG

GACCTATGGACGGCCTTCAACGAGCGCTCCGTGGCCGCGCACCTGGCGGACATCATTTTCCCCG

AACGCCTGCTTAAAACCCTGCAACAGGGTCTGCCAGACTTCACCAGTCAAAGCATGTTGCAGAAC

TTTAGGAACTTTATCCTAGAGCGCTCAGGAATCTTGCCCGCCACCTGCTGTGCACTTCCTAGCGA

CTTTGTGCCCATTAAGTACCGCGAATGCCCTCCGCCGCTTTGGGGCCACTGCTACCTTCTGCAG

CTAGCCAACTACCTTGCCTACCACTCTGACATAATGGAAGACGTGAGCGGTGACGGTCTACTGGA

GTGTCACTGTCGCTGCAACCTATGCACCCCGCACCGCTCCCTGGTTTGCAATTCGCAGCTGCTTA

ACGAAAGTCAAATTATCGGTACCTTTGAGCTGCAGGGTCCCTCGCCTGACGAAAAGTCCGCGGC

TCCGGGGTTGAAACTCACTCCGGGGCTGTGGACGTCGGCTTACCTTCGCAAATTTGTACCTGAG

GACTACCACGCCCACGAGATTAGGTTCTACGAAGACCAATCCCGCCCGCCAAATGCGGAGCTTA

CCGCCTGCGTCATTACCCAGGGCCACATTCTTGGCCAATTGCAAGCCATCAACAAAGCCCGCCA

AGAGTTTCTGCTACGAAAGGGACGGGGGGTTTACTTGGACCCCCAGTCCGGCGAGGAGCTCAAC

CCAATCCCCCCGCCGCCGCAGCCCTATCAGCAGCAGCCGCGGGCCCTTGCTTCCCAGGATGGC

ACCCAAAAAGAAGCTGCAGCTGCCGCCGCCACCCACGGAGGAGGAGGAATACTGGGACAGTCA

GGCAGAGGAGGTTTTGGACGAGGAGGAGGAGGACATGATGGAAGACTGGGAGAGCCTAGACGA

GGAAGCTTCCGAGGTCGAAGAGGTGTCAGACGAAACACCGTCACCCTCGGTCGCATTCCCCTCG

CCGGCGCCCCAGAAATCGGCAACCGGTTCCAGCATGGCTACAACCTCCGCTCCTCAGGCGCCG

CCGGCACTGCCCGTTCGCCGACCCAACCGTAGATGGGACACCACTGGAACCAGGGCCGGTAAG

TCCAAGCAGCCGCCGCCGTTAGCCCAAGAGCAACAACAGCGCCAAGGCTACCGCTCATGGCGC

GGGCACAAGAACGCCCATAGTTGCTTGCTTGCAAGACTGTGGGGGCAACATCTCCTTCGCCCGCC

GCTTTCTTCTCTACCATCACGCGTGGCCTTCCCCCGTAACATCCTGCATTACTACCGTCATCTCT

ACAGCCCATACTGCACCGGCGGCAGCGGCAGCGGCAGCAACAGCAGCGGCCACACAGAAGCAA
```

-continued

```
AGGCGACCGGATAGCAAGACTCTGACAAAGCCCAAGAAATCCACAGCGGCGGCAGCAGCAGGA

GGAGGAGCGCTGCGTCTGGCGCCCAACGAACCCGTATCGACCCGCGAGCTTAGAAACAGGATT

TTTCCCACTCTGTATGCTATATTTCAACAGAGCAGGGGCCAAGAACAAGAGCTGAAAATAAAAAAC

AGGTCTCTGCGATCCCTCACCCGCAGCTGCCTGTATCACAAAAGCGAAGATCAGCTTCGGCGCA

CGCTGGAAGACGCGGAGGCTCTCTTCAGTAAATACTGCGCGCTGACTCTTAAGGACTAGTTTCG

CGCCCTTTCTCAAATTTAAGCGCGAAAACTACGTCATCTCCAGCGGCCACACCCGGCGCCAGCA

CCTGTCGTCAGCGCCATTATGAGCAAGGAAATTCCCACGCCCTACATGTGGAGTTACCAGCCACA

AATGGGACTTGCGGCTGGAGCTGCCCAAGACTACTCAACCCGAATAAACTACATGAGCGCGGGA

CCCCACATGATATCCCGGGTCAACGGAATCCGCGCCCACCGAAACCGAATTCTCTTGGAACAGG

CGGCTATTACCACCACACCTCGTAATAACCTTAATCCCCGTAGTTGGCCCGCTGCCCTGGTGTAC

CAGGAAAGTCCCGCTCCCACCACTGTGGTACTTCCCAGAGACGCCCAGGCCGAAGTTCAGATGA

CTAACTCAGGGGCGCAGCTTGCGGGCGGCTTTCGTCACAGGGTGCGGTCGCCCGGGCAGGGTA

TAACTCACCTGACAATCAGAGGGCGAGGTATTCAGCTCAACGACGAGTCGGTGAGCTCCTCGCT

TGGTCTCCGTCCGGACGGGACATTTCAGATCGGCGGCGCCGGCCGTCCTTCATTCACGCCTCGT

CAGGCAATCCTAACTCTGCAGACCTCGTCCTCTGAGCCGCGCTCTGGAGGCATTGGAACTCTGC

AATTTATTGAGGAGTTTGTGCCATCGGTCTACTTTAACCCCTTCTCGGGACCTCCCGGCCACTAT

CCGGATCAATTTATTCCTAACTTTGACGCGGTAAAGGACTCGGCGGACGGCTACGACTGAATGTT

AAGTGGAGAGGCAGAGCAACTGCGCCTGAAACACCTGGTCCACTGTCGCCGCCACAAGTGCTTT

GCCCGCGACTCCGGTGAGTTTTGCTACTTTGAATTGCCCGAGGATCATATCGAGGGCCCGGCGC

ACGGCGTCCGGCTTACCGCCCAGGGAGAGCTTGCCCGTAGGCTGATTCGGGAGTTTACCCAGG

GCCCCCTGCTAGTTGAGCGGGACAGGGGACCCTGTGTTCTCACTGTGATTTGCAACTGTCCTAA

CCTTGGATTACATCAAGATCCTCTAGTTATAACTAGAGTACCCGGGGATCTTATTCCCTTTAACTA

ATAAAAAAAAATAATAAAGCATCACTTACTTAAAATCAGTTAGCAAATTTCTGTCCAGTTTATTCAG

GAGCACCTCCTTGCGCTCCTCCCAGCTCTGGTATTGGAGCTTCCTCCTGGCTGCAAACTTTCTCC

ACAATCTAAATGGAATGTCAGTTTCCTCCTGTTCCTGTCCATCCGCACCCACTATCTTCATGTTGT

TGCAGATGAAGCGCGCAAGACCGTCTGAAGATACCTTCAACCCCGTGTATCCATATGACACGGAA

ACCGGTCCTCCAACTGTGCCTTTTCTTACTCCTCCCTTTGTATCCCCCAATGGGTTTCAAGAGAGT

CCGCCTGGGGTACTCTCTTTGCGCCTATCCGAACCTCTAGTTACCTCCAATGGCATGCTTGCGCT

CAAAATGGGCAACGGCCTCTCTCTGGACGAGGCCGGCAACCTTACCTCCCAAAATGTAACCACT

GTGAGCCCACCTCTCAAAAAAACCAAGTCAAACATAAACCTGGAAATATCTGCACCCCTCACAGT

TACCTCAGAAGCCCTAACTGTGGCTGCCGCCGCACCTCTAATGGTCGCGGGCAACACACTCACC

ATGCAATCAGAGGCCGCGCTAACCGTGCAGGACTCCAAACTTAGGATTGCCACCCAAGGACCCC

TCACAGTGTCAGAAGGAAAGCTAGCCCTGCAAACATCAGGCCCCCTCACCACCACCGATAGCAG

TACCCTTACTATCACTGCCTCACCCCCTCTAACTACTGCCACTGGTAGCTTGGGCATTGACTTGAA

AGAGCCCATTTATACACAAAATGGAAAACTAGGACTAAAGTACGGGGCTCCTTTGCATGTAACAG

ACGAGCTAAACACTTTGACCGTAGCAACTGGTCCAGGTGTGACTATTAATAATACTTCCTTGCAAA

CTAAAGTTACTGGAGCCTTGGGTTTTGATTCACAAGGCAATATGCAACTTAATGTAGCAGGAGGA

CTAAGGATTGATTCTCAAAACAGACGCCTTATACTTGATGTTAGTTATCCGTTTGATGCTCAAAAC

CAACTAAATCTAAGACTAGGACAGGGCCCTCTTTTTATAAACTCAGCCCACAACTTGGATATTAAC

TACAACAAAGGCCTTTACTTGTTTACAGCTTCAAACAATTCCAAAAAGCTTGAGGTTAACCTAAGC
```

ACTGCCAAGGGGTTGATGTTTGACGCTACAGCCATAGCCATTAATGCAGGAGATGGGCTTGAATT

TGGTTCACCTAATGCACCAAACACAAATCCCCTCAAAACAAAAATTGGCCATGGCCTAGAATTTGA

TTCAAACAAGGCTATGGTTCCTAAACTAGGAACTGGCCTTAGTTTTGACAGCACAGGTGCCATTA

CAGTAGGAAACAAAAATAATGATAAGCTAACTTTGTGGACCACACCAGCTCCATCTCCTAACTGTA

GACTAAATGCAGAGAAAGATGCTAAACTCACTTTGGTCTTAACAAAATGTGGCAGTCAAATACTTG

CTACAGTTTCAGTTTTGGCTGTTAAAGGCAGTTTGGCTCCAATATCTGGAACAGTTCAAAGTGCTC

ATCTTATTATAAGATTTGACGAAAATGGAGTGCTACTAAACAATTCCTTCCTGGACCCAGAATATT

GGAACTTTAGAAATGGAGATCTTACTGAAGGCACAGCCTATACAAACGCTGTTGGATTTATGCCTA

ACCTATCAGCTTATCCAAAATCTCACGGTAAAACTGCCAAAAGTAACATTGTCAGTCAAGTTTACT

TAAACGGAGACAAAACTAAACCTGTAACACTAACCATTACACTAAACGGTACACAGGAAACAGGA

GACACAACTCCAAGTGCATACTCTATGTCATTTTCATGGGACTGGTCTGGCCACAACTACATTAAT

GAAATATTTGCCACATCCTCTTACACTTTTTCATACATTGCCCAAGAATAAAGAATCGTTTGTGTTA

TGTTTGAACGTGTTTATTTTTCAATTGCAGAAAATTTCAAGTCATTTTTGATTGAGTAGTATAGGCC

CACCACCACATAGCTTATACAGATCACCGTACCTTAATCAAAC pSSI10902 (SEQ ID NO: 2):
AATGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCTGGTTAGACCAGATCTGAGCCT

GGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGGGAAACCAGAGG

AGCTCTCTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTGCGAGAGCG

TCAGTATTAAGCGGGGGAGAATTAGATCGCGATGGGAAAAAATTCGGTTAAGGCCAGGGGGAAA

GAAAAAATATAAATTAAAACATATAGTATGGGCAAGCAGGGAGCTAGAACGATTCGCAGTTAATCC

TGGCCTGTTAGAAACATCAGAAGGCTGTAGACAAATACTGGGACAGCTACAACCATCCCTTCAGA

CAGGATCAGAAGAACTTAGATCATTATATAATACAGTAGGAACCCTCTATTGTGTGCATCAAAGGA

TAGAGATAAAAGACACCAAGGAAGCTTTAGACAAGATAGAGGAAGAGCAAAACAAAAGTAAGACC

ACCGCACAGCAAGCGGCCGCTGATCTTCAGACCTGGAGGAGGAGATATGAGGGACAATTGGAG

AAGTGAATTATATAAATATAAAGTAGTAAAAATTGAACCATTAGGAGTAGCACCCACCAAGGCAAA

GAGAAGAGTGGTGCAGAGAGAAAAAAGAGGAGTGGGAATAGGAGCTTTGTTCCTTGGGTTCTTG

GGAGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTGTTG

CAACTCACAGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTGCTGTGCCT

TGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCA

AGAAAAGAATGAACAAGAATTATTGGAATTAGATAAATGGGCAAGTTTGTGGAATTGGTTTAACAT

AACAAATTGGCTGTGGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCATTATCGTTTCAGAC

-continued

```
CCACCTCCCAACCCCGAGGGGACCCGACAGGCCCGAAGGAATAGAAGAAGAAGGTGGAGAGAG

AGACAGAGACAGATCCATTCGATTAGTGAACGGATCTCGACGGTATCGATTGGGCCCGAGATCT

CGCGCGCGAGGCCTGCCATGGGCATGCCTGCAGGTCGATGCGTGGCCGGCCTAGGATCCATAT

GGTACCGGTAAATGGCCCGCCTGGCTGACCGCCCAACGACCCCCGCCCATTGACGTCAATAATG

ACGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTTGG

CAGTACATCTAGTATTAGTCATCGCTATTACCATGGTGATGCGGTTTTGGCAGTACATCAATGGGC

GTGGATAGCGGTTTGACTCACGGGGATTTCCAAGTCTCCACCCCATTGACGTCAATGGGAGTTTG

TTTTGGCACCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCGTTTAGTGAACCGTCAGATC

GCCTGGAGACGCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACGTAAGTACCGCCT

ATAGACTCTATAGGCACACCCCTTTGGCTCTTATGCATGAATTAATAGGACTCACTATAGGGAGAC

AGACTGTTCCTTTCCTGGGTCTTTTCTGCAGGCTAGCCCCACCATGCCGCGCGCTCCCCGCTGC

CGAGCCGTGCGCTCCCTGCTGCGCAGCCACTACCGCGAGGTGCTGCCGCTGGCCACGTTCGTG

CGGCGCCTGGGGCCCCAGGGCTGGCGGCTGGTGCAGCGCGGGGACCCGGCGGCTTTCCGCG

CGCTGGTGGCCCAGTGCCTGGTGTGCGTGCCCTGGGACGCACGGCCGCCCCCCGCCGCCGCC

TCCTTCCGCCAGGTGTCCTGCCTGAAGGAGCTGGTGGCCCGAGTGCTGCAGAGGCTGTGCGAG

CGCGGCGCGAAGAACGTGCTGGCCTTCGGCTTCGCGCTGCTGGACGGGGCCCGCGGGGGCCC

CCCCGAGGCCTTCACCACCAGCGTGCGCAGCTACCTGCCCAACACGGTGACCGACGCACTGCG

GGGGAGCGGGGCGTGGGGGCTGCTGTTGCGCCGCGTGGGCGACGACGTGCTGGTTCACCTGC

TGGCACGCTGCGCGCTCTTTGTGCTGGTGGCTCCCAGCTGCGCCTACCAGGTGTGCGGGCCGC

CGCTGTACCAGCTCGGCGCTGCCACTCAGGCCCGGCCCCCGCCACACGCTAGTGGACCCCGAA

GGCGTCTGGGATGCGAACGGGCCTGGAACCATAGCGTCAGGGAGGCCGGGGTCCCCCTGGGC

CTGCCAGCCCCGGGTGCGAGGAGGCGCGGGGCAGTGCCAGCCGAAGTCTGCCGTTGCCCAA

GAGGCCCAGGCGTGGCGCTGCCCCTGAGCCGGAGCGGACGCCCGTTGGGCAGGGGTCCTGGG

CCCACCCGGGCAGGACGCGTGGACCGAGTGACCGTGGTTTCTGTGTGGTGTCACCTGCCAGAC

CCGCCGAAGAAGCCACCTCTTTGGAGGGTGCGCTCTCTGGCACGCGCCACTCCCACCCATCCGT

GGGCCGCCAGCACCACGCGGGCCCCCATCCACATCGCGGCCACCACGTCCCTGGGACACGC

CTTGTCCCCGGTGTACGCCGAGACCAAGCACTTCCTCTACTCCTCAGGCGACAAGGAGCAGCT

GCGGCCCTCCTTCCTACTCAGCTCTCTGAGGCCCAGCCTGACTGGCGCTCGGAGGCTCGTGGA

GACCATCTTTCTGGGTTCCAGGCCCTGGATGCCAGGGACTCCCCGCAGGTTGCCCCGCCTGCC

CCAGCGCTACTGGCAAATGCGGCCCCTGTTTCTGGAGCTGCTTGGGAACCACGCGCAGTGCCC

CTACGGGGTGCTCCTCAAGACGCACTGCCCGCTGCGAGCTGCGGTCACCCCAGCAGCCGGTGT

CTGTGCCCGGGAGAAGCCCCAGGGCTCTGTGGCGGCCCCGAGGAGGAGGACACAGACCCCC

GTCGCCTGGTGCAGCTGCTCCGCCAGCACAGCAGCCCTGGCAGGTGTACGGCTTCGTGCGGG

CCTGCCTGCGCCGGCTGGTGCCCCAGGCCTCTGGGGCTCCAGGCACAACGAACGCCGCTTCC

TCAGGAACACCAAGAAGTTCATCTCCCTGGGGAAGCATGCCAAGCTCTCGCTGCAGGAGCTGAC

GTGGAAGATGAGCGTGCGGGCTGCGCTTGGCTGCGCAGGAGCCCAGGGGTTGGCTGTGTTCC

GGCCGCAGAGCACCGTCTGCGTGAGGAGATCCTGGCCAAGTTCCTGCACTGGCTGATGAGTGT
```

-continued

```
GTACGTCGTCGAGCTGCTCAGGTCTTTCTTTTATGTCACGGAGACCACGTTTCAAAAGAACAGGC

TCTTTTTCTACCGGAAGAGTGTCTGGAGCAAGTTGCAAAGCATTGGAATCAGACAGCACTTGAAG

AGGGTGCAGCTGCGGGAGCTGTCGGAAGCAGAGGTCAGGCAGCATCGGGAAGCCAGGCCCGC

CCTGCTGACGTCCAGACTCCGCTTCATCCCCAAGCCTGACGGGCTGCGGCCGATTGTGAACATG

GACTACGTCGTGGGAGCCAGAACGTTCCGCAGAGAAAAGAGGGCCGAGCGTCTCACCTCCAGG

GTGAAGGCACTGTTCAGCGTGCTCAACTACGAGCGGGCGCGGCGCCCCGGCCTCCTGGGCGCC

TCTGTGCTGGGCCTGGACGATATCCACAGGGCCTGGCGCACCTTCGTGCTGCGTGTGCGGGCC

CAGGACCCGCCGCCTGAGCTGTACTTTGTCAAGGTGGATGTGACGGGCGCGTACGACACCATCC

CCCAGGACAGGCTCACGGAGGTCATCGCCAGCATCATCAAACCCCAGAACACGTACTGCGTGCG

TCGGTATGCCGTGGTCCAGAAGGCCGCCCATGGGCACGTCCGCAAGGCCTTCAAGAGCCACGT

CTCTACCTTGACAGACCTCCAGCCGTACATGCGACAGTTCGTGGCTCACCTGCAGGAGACCAGC

CCGCTGAGGGATGCCGTCGTCATCGAGCAGAGCTCCTCCCTGAATGAGGCCAGCAGTGGCCTC

TTCGAGGTCTTCCTACGCTTCATGTGCCACCACGCCGTGCGCATCAGGGGCAAGTCCTACGTCC

AGTGCCAGGGGATCCCGCAGGGCTCCATCCTCTCCACGCTGCTCTGCAGCCTGTGCTACGGCG

ACATGGAGAACAAGCTGTTTGCGGGGATTCGGCGGGACGGGCTGCTCCTGCGTTTGGTGGATG

ATTTCTTGTTGGTGACACCTCACCTCACCCACGCGAAAACCTTCCTCAGGACCCTGGTCCGAGGT

GTCCCTGAGTATGGCTGCGTGGTGAACTTGCGGAAGAGAGTGGTGAACTTCCCTGTAGAAGACG

AGGCCCTGGGTGGCACGGCTTTTGTTCAGATGCCGGCCCACGGCCTATTCCCCTGGTGCGGCC

TGCTGCTGGATACCCGGACCCTGGAGGTGCAGAGCGACTACTCCAGCTATGCCCGGACCTCCAT

CAGAGCCAGTCTCACCTTCAACCGCGGCTTCAAGGCTGGGAGGAACATGCGTCGCAAACTCTTT

GGGGTCTTGCGGCTGAAGTGTCACAGCCTGTTTCTGGATTTGCAGGTGAACAGCCTCCAGAGGG

TGTGCACCAACATCTACAAGATCCTCCTGCTGCAGGCGTACAGGTTTCACGCATGTGTGCTGCAG

CTCCCATTTCATCAGCAAGTTTGGAAGAACCCCACATTTTTCCTGCGCGTCATCTCTGACACGGC

CTCCCTCTGCTACTCCATCCTGAAAGCCAAGAACGCAGGGATGTCGCTGGGGGCCAAGGGCGC

CGCCGGCCCTCTGCCCTCCGAGGCCGTGCAGTGGCTGTGCCACCAAGCATTCCTGCTCAAGCT

GACTCGACACCGTGTCACCTACGTGCCACTCCTGGGGTCACTCAGGACAGCCCAGACGCAGCTG

AGTCGGAAGCTCCCGGGACGACGCTGACTGCCCTGGAGGCCGCAGCCAACCCGGCACTGCC

CTCAGACTTCAAGACCATCCTGGACTGAGTCGAAACTCGAGGATCCGGCTGTGGAATGTGTGTC

AGTTAGGGTGTGGAAAGTCCCCAGGCTCCCCAGCAGGCAGAAGTATGCAAAGCATGCATCTCAA

TTAGTCAGCAACCAGGTGTGGAAAGTCCCCAGGCTCCCCAGCAGGCAGAAGTATGCAAAGCATG

CATCTCAATTAGTCAGCAACCATAGTCCCGCCCCTAACTCCGCCCATCCCGCCCCTAACTCCGCC

CAGTTCCGCCCATTCTCCGCCCCATGGCTGACTAATTTTTTTATTTATGCAGAGGCCGAGGCCG

CCTCGGCCTCTGAGCTATTCCAGAAGTAGTGAGGAGGCTTTTTTGGAGGCCGTCGGCCGCCACG

ACCGGTGCCGCCACCATCCCCTGACCCACGCCCCTGACCCCTCACAAGGAGACGACCTTCCATG

ACCGAGTACAAGCCCACGGTGCGCCTCGCCACCCGCGACGACGTCCCCGGGCCGTACGCACC

CTCGCCGCCGCGTTCGCCGACTACCCTGCAACACGCCATACAGTGGACCCTGACCGCCACATCG

AGCGGGTCACCGAGCTGCAAGAACTCTTCCTCACGCGCGTCGGGCTCGACATCGGCAAGGTGT

GGGTCGCGGACGACGGCGCCGCGGTGGCGGTCTGGACCACGCCGGAGAGCGTCGAAGCGGG

GGCGGTGTTCGCCGAGATCGGCCCGCGCATGGCCGAGTTGAGCGGTTCCCGGCTGGCCGCGC

AGCAACAGATGGAAGGCCTCCTGGCGCCGCACCGGCCCAAGGAGCCCGCGTGGTTCCTGGCCA
```

-continued

```
CCGTCGGCGTCTCGCCCGACCACCAGGGCAAGGGTCTGGGCAGCGCCGTCGTGCTCCCCGGA
GTGGAGGCGGCCGAGCGCGCCGGGGTGCCCGCCTTCCTGGAGACCTCCGCGCCCCGCAACCT
CCCCTTCTACGAGCGGCTCGGCTTCACCGTCACCGCCGACGTCGAGGTGCCCGAAGGACCGCG
CACCTGGTGCATGACCCGCAAGCCCGGTGCCTGACGCCCGCCCCACGACCCGCAGCGCCCGAC
CGAAAGGAGGGCACGACCCCATGCATCGATAAAATAAAAGATTTTATTTAGTCTCCAGAAAAGG
GGGGAATGAAAGACCCCACCTGTAGGTTTGGCAAGCTAGGCCTATTAATATTCCGGAGTATACGT
AGCCGGCTAACGTTAACAACCGGTACGATGCATTAGTTATTAATAGTAATCAATTACGGGGTCATT
AGTTCATAGCCCATATATGGAGTTCCGCGTTACATAACTTACGGTAAATGGCCCGCCTGGCTGAC
CGCCCAACGACCGCCGCCCATTGACGTCAATAATGACGTATGTTCCCATAGTAAGGCCAATAGGG
ACTTTCCATTGACGTCAATGGGTGGAGTATTTACGGTAAACTGCCCACTTGGCAGTACATCAAGT
GTATCATATGCCAAGTACGCCCCCTATTGACGTCAATGACGGTAAATGGCCCGCCTGGCATTATG
CCCAGTACATGACCTTATGGGACTTTCCTACTTGGCAGTACATCTACGTATTAGTCATCGCTATTA
CCATGGTGATGCGGTTTTGGCAGTACATCAATGGGCGTGGATAGGGGTTTGACTGAGGGGGATT
TCCAAGTCTCCACCCCATTGACGTCAATGGGAGTTTGTTTTGGCACCAAAATCAACGGGACTTTC
CAAAATGTCGTAACAACTCCGCCCCATTGACGCAAATGGGCGGTAGGCGTGTACGGTGGGAGGT
CTATATAAGCAGAGCTGGTTTAGTGAACCGTCAGATCCGCTAGCGCTACCGGACTCAGATCTCGA
GCTCAAGGTTCGAATTCTGCAGTCGACCCACCATGGCTCTTTCAAACAAGTTTATCGGAGATGAC
ATGAAAATGACCTACCATATGGATGGCTGTGTCAATGGGCATTACTTTACCGTCAAAGGTGAAGG
CAGCGGGAAGCCATACGAAGGGACGCAGACCTCGACTTTTAAAGTCACCATGGCCAACGGTGGG
CCCCTTGCATTCTCCTTTGACATACTATCTACAGTGTTCATGTATGGAAATCGATGCTTTACTGCG
TATCCTACCAGTATGCCCGACTATTTCAAACAAGCATTTCCTGACGGAATGTCATATGAAAGGACT
TTTACCTATGAAGATGGAGGAGTTGCTACAGCCAGTTGGGAAATAAGCCTTAAAGGCAACTGCTT
TGAGCACAAATCCACGTTTCATGGAGTGAACTTTCCTGCTGATGGACCTGTGATGGCGAAGATGA
CAACTGGTTGGGACCCATCTTTTGAGAAAATGACTGTCTGCGATGGAATATTGAAGGGTGATGTC
ACCGCGTTCCTCATGCTGCAAGGAGGTGGCAATTACAGATGCCAATTCCACACTTCTTACAAGAC
AAAAAAACCGGTGACGATGCCACCAAACCATGCGGTGGAACATCGCATTGCGAGGACCGACCTT
GACAAAGGTGGCAACAGTGTTCAGCTGACGGAGCACGCTGTTGCACATATAACCTCTGTTGTCCC
TTTCTAGCGGCCGCGATAATCAACCTCTGGATTACAAAATTTGTGAAAGATTGACTGGTATTCTTA
ACTATGTTGCTCCTTTTACGCTATGTGGATACGCTGCTTTAATGCCTTTGTATCATGCTATTGCTTC
CCGTATGGCTTTCATTTTCTCCTCCTTGTATAAATCCTGGTTGCTGTCTCTTTATGAGGAGTTGTG
GCCCGTTGTCAGGCAACGTGGCGTGGTGTGCACTGTGTTTGCTGACGCAACCCCCACTGGTTGG
GGCATTGCCACCACCTGTCAGCTCCTTTCCGGGACTTTCGCTTTCCCCCTCCCTATTGCCACGGC
GGAACTCATCGCCGCCTGCCTTGCCCGCTGCTGGACAGGGGCTCGGCTGTTGGGCACTGACAA
TTCCGTGGTGTTGTCGGGGAAGCTGAGGTCCTTTCCATGGCTGCTCGCCTGTGTTGCCACCTGG
ATTCTGCGCGGGACGTCCTTCTGCTACGTCCCTTCGGCCCTCAATCCAGCGGACCTTCCTTCCC
GCGGCCTGCTGCCGGCTCTGCGGCCTCTTCCGCGTCTTCGCCTTCGCCCTCAGACGAGTCGGA
TCTCCCTTTGGGCCGCCTCCCCGCATCGGACGCGTGGTACCTTTAAGACCAATGACTTACAAGG
CAGCTGTAGATCTTAGCCACTTTTTAAAAGAAAAGGGGGGACTGGAAGGGCTAATTCACTCCCAA
CGAAGACAAGATCTGCTTTTTGCTTGTACTGGGTCTCTCTGGTTAGACCAGATCTGAGCCTGGGA
GCTCTCTGGCTAACTAGGGAACCCACTGCTTAAGCCTCAATAAAGCTTGCCTTGAGTGCTTCAAG
TAGTGTGTGCCCGTCTGTTGTGTGACTCTGGTAACTAGAGATCCCTCAGACCCTTTTAGTCAGTG
```

-continued

```
TGGAAAATCTCTAGCAGTAGTAGTTCATGTCATCTTATTATTCAGTATTTATAACTTGCAAAGAAAT

GAATATCAGAGAGTGAGAGGAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAAACTCATCAA

TGTATCTTATCATGTCTGGCTCTAGCTATCCCGCCCCTAACTCCGCCCATCCCGCCCCTAACTCC

GCCCAGTTCCGCCCATTCTCCGCCCCATGGCTGACTAATTTTTTTTATTTATGCAGAGGCCGAGG

CCGCCTCGGCCTCTGAGCTATTCCAGAAGTAGTGAGGAGGCTTTTTTGGAGGCCTAGGGACGTA

CCCAATTCGCCCTATAGTGAGTCGTATTACGCGCGCTCACTGGCCGTCGTTTTACAACGTCGTGA

CTGGGAAAACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAATGGCGAAT

GGGACGCGCCCTGTAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGG

AACAACACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGCTTACAA

TTTAGGTGGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAAGGAAGAG

TATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCA

ATGATGAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAAC

ACTGCGGCCAACTTACTTCTGACAACGATCGGAGGACCGAAGGAGCTAACCGCTTTTTTGCACAA

CATGGGGGATCATGTAACTCGCCTTGATCGTTGGGAACCGGAGCTGAATGAAGCCATACCAAAC

GACGAGCGTGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCCCGTATCGTAGTTAT

CTACACGACGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGGGAACGACCTACACCGAACTGAGATACCTACAGCGTGAGCTATG
```

-continued

AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGGCGGAGCCTATGGA

AAAACGCCAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT pSSI12112 (SEQ ID NO: 3):
AATGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCTGGTTAGACCAGATCTGAGCCT

GGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGGGAAACCAGAGG

AGCTCTCTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTGCGAGAGCG

TCAGTATTAAGCGGGGGAGAATTAGATCGCGATGGGAAAAAATTCGGTTAAGGCCAGGGGGAAA

GAAAAAATATAAATTAAAACATATAGTATGGGCAAGCAGGGAGCTAGAACGATTCGCAGTTAATCC

TGGCCTGTTAGAAACATCAGAAGGCTGTAGACAAATACTGGGACAGCTACAACCATCCCTTCAGA

CAGGATCAGAAGAACTTAGATCATTATATAATACAGTAGCAACCCTCTATTGTGTGCATCAAAGGA

TAGAGATAAAAGACACCAAGGAAGCTTTAGACAAGATAGAGGAAGAGCAAAACAAAAGTAAGACC

ACCGCACAGCAAGCGGCCGCTGATCTTCAGACCTGGAGGAGGAGATATGAGGGACAATTGGAG

AAGTGAATTATATAAATATAAAGTAGTAAAAATTGAACCATTAGGAGTAGCACCCACCAAGGCAAA

GAGAAGAGTGGTGCAGAGAGAAAAAAGAGCAGTGGGAATAGGAGCTTTGTTCCTTGGGTTCTTG

GGAGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTGTTG

CAACTCACAGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTGCTGTGCCT

TGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCA

AGAAAAGAATGAACAAGAATTATTGGAATTAGATAAATGGGCAAGTTTGTGGAATTGGTTTAACAT

AACAAATTGGCTGTGGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCATTATCGTTTCAGAC

CCACCTCCCAACCCCGAGGGGACCCGAGAGGCCCGAAGGAATAGAAGAAGAAGGTGGAGAGAG

AGACAGAGACAGATCCATTCGATTAGTGAACGGATCTCGACGGTATCGATACTAGTAATTTTTCTG

CAGAAAACGTACCCGGGGATCCTCTAGGATCCCACCGAAAGGTTGCTCCTTAACACAGGCTAAG

-continued

```
GACCAGCTTCTTTGGGAGAGAACAGACGCAGGGGCGGGAGGGAAAAAGGGAGAGGCAGACGTC
ACTTCCCCTTGGCGGCTCTGGCAGCAGATTGGTCGGTTGAGTGGCAGAAAGGCAGACGGGGAC
TGGGCAAGGCACTGTCGGTGACATCACGGACAGGGCGACTTCTATGTAGATGAGGCAGCGCAG
AGGCTGCTGCTTCGCCACTTGCTGCTTCGCCACGAAGGAGTTCCCGTGCCCTGGGAGCGGGTTC
AGGACCGCGGATCGGAAGTGAGAATCCCAGCTGTGTGTCAGGGCTGGAAAGGGCTCGGGAGTG
CGCGGGGCAAGTGACCGTGTGTGTAAAGAGTGAGGCGTATGAGGCTGTGTCGGGGCAGAGCCC
GAAGATCCGGGTTGCGGAGGGTGGGCCTGGGAGGGGTGGTGGCCATTTTTTGTCTAACCCTAAC
TGAGAAGGGCGTAGGCGCCGTGCTTTTGCTCCCCGCGCGCTGTTTTTCTCGCTGACTTTCAGCG
GGCGGAAAAGCCTCGGCCTGCCGCCTTCCACCGTTCATTCTAGAGCAAACAAAAAATGTCAGCT
GCTGGCCCGTTCGCCCCTCCCGGGGACCTGCGGCGGGTCGCCTGCCCAGCCCCCGAACCCCG
CCTGGAGGCCGCGGTCGGCCCGGGGCTTCTCCGGAGGCACCCACTGCCACCGCGAAGAGTTG
GGCTCTGTCAGCCGCGGGTCTCTCGGGGGCGAGGGCGAGGTTCAGGCCTTTCAGGCCGCAGG
AAGAGGAACGGAGCGAGTCCCCGCGCGCGGCGCGATTCCCTGAGCTGTGGGACGTGCACCCA
GGACTCGGCTCACACATGCAGTTCGCTTTCCTGTTGGTGGGGGGAACGCCGATCGTGCGCATCC
GTCACCCCTCGCCGGCAATGGGGGCTTGTGAACCCCCAAACCTGACTGACTGGGCCAGTGTGCT
GCAAATTGGCAGGAGACGTGAAGGCACCTCCAAAGTCGACTTTCTGGAGTTTCAAAAACAGACC
GTACATGTCCGCGGTCGCGACGTACCTACCGGGTAGGGGAGGCGCTTTTCCCAAGGCAGTCTG
GAGCATGCGCTTTAGCAGCCCCGCTGGGCACTTGGCGCTACACAAGTGGCCTCTGGCCTCGCA
CACATTCCACATCCACCGGTAGGCGCCAACCGGCTCCGTTCTTTGGTGGCCCCTTCGCGCCACC
TTCTACTCCTCCCCTAGTCAGGAAGTTCCCCCCCGCCCCGCAGCTCGCGTCGTGCAGGACGTGA
CAAATGGAAGTAGCACGTCTCACTAGTCTCGTGCAGATGGACAGCACCGCTGAGCAATGGAAGC
GGGTAGGCCTTTGGGGCAGCGGCCAATAGCAGCTTTGCTCCTTCGCTTTCTGGGCTCAGAGGCT
GGGAAGGGGTGGGTCCGGGGGCGGGCTCAGGGGCGGGCTCAGGGGCGGGCGGGCGCCCG
AAGTCCTCCGGAGGCCCGGCATTCTGCACGCTTCAAAAGCGCACGTCTGCCGCGCTGTTCTCCT
CTTCCTCATCTCCGGGCCTTTCGACTCTAGACACGTGTTGACAATTAATCATCGGCATAGTATATC
GGCATAGTATAATACGAGAAGGTGAGGAACTAAACCATGGCCAAGCCTTTGTCTCAAGAAGAATC
CACCCTCATTGAAAGAGCAACGGCTACAATCAACAGCATCCCCATCTCTGAAGACTACAGCGTCG
CCAGCGCAGCTCTCTCTAGCGACGGCCGCATCTTCACTGGTGTCAATGTATATCATTTTACTGGG
GGACCTTGTGCAGAACTCGTGGTGCTGGGCACTGCTGCTGCTGCGGCAGCTGGCAACCTGACTT
GTATCGTCGCGATCGGAAATGAGAAGAGGGGCATCTTGAGGCCCTGCGGAGGGTGCCGAGAGG
TGCTTCTCGATCTGCATCCTGGGATCAAAGCCATAGTGAAGGACAGTGATGGACAGCCGACGGC
AGTTGGGATTCGTGAATTGCTGCCCTCTGGTTATGTGTGGGAGGGCTAAGCACAATTCGAGCTC
GGTACGCGTATCGATGGCGCCAGCTGCAGGCGGCCGCCATATGCATCCTAGGCCTATTAATATT
CCGGAGTATACGTAGGCGGCTAACGTTAACAACCGGTACGATGCATTAGTTATTAATAGTAATCAA
TTACGGGGTCATTAGTTCATAGCCCATATATGGAGTTCCGCGTTACATAACTTACGGTAAATGGCC
CGCCTGGCTGACCGCCCAACGACCCCCGCCCATTGACGTCAATAATGACGTATGTTCCCATAGT
AACGCCAATAGGGACTTTCCATTGACGTCAATGGGTGGAGTATTTACGGTAAACTGCCCACTTGG
CAGTACATCAAGTGTATCATATGCCAAGTACGCCGCCTATTGAGGTCAATGAGGGTAAATGGCCC
GCCTGGCATTATGCCCAGTACATGACCTTATGGGACTTTCCTACTTGGCAGTACATCTACGTATTA
GTCATCGCTATTACCATGGTGATGCGGTTTTGGCAGTACATCAATGGGCGTGGATAGCGGTTTGA
CTCACGGGGATTTCCAAGTCTCCACCCCATTGACGTCAATGGGAGTTTGTTTTGGCACCAAAATC
```

-continued

```
AACGGGACTTTCCAAAATGTCGTAACAACTCCGCCCCATTGACGCAAATGGGCGGTAGGCGTGT
ACGGTGGGAGGTCTATATAAGCAGAGCTGGTTTAGTGAACCGTCAGATCCGCTAGCCCCACCAT
GCCGCGCGCTCCCCGCTGCCGAGCCGTGCGCTCCCTGCTGCGCAGCCACTACCGCGAGGTGCT
GCCGCTGGCCACGTTCGTGCGGCGCCTGGGGCCCCAGGGCTGGCGGCTGGTGCAGCGCGGG
GACCCGGCGGCTTTCCGCGCGCTGGTGGCCCAGTGCCTGGTGTGCGTGCCCTGGGACGCACG
GCCGCCCCCGCCGCCCCCTCCTTCCGCCAGGTGTCCTGCCTGAAGGAGCTGGTGGCCCGAGT
GCTGCAGAGGCTGTGCGAGCGCGGCGCGAAGAACGTGCTGGCCTTCGGCTTCGCGCTGCTGGA
CGGGGCCCGCGGGGGCCCCCCCGAGGCCTTCACCACCAGCGTGCGCAGCTACCTGCCCAACA
CGGTGACCGACGCACTGCGGGGAGCGGGGCGTGGGGCTGCTGTTGCGCCGCGTGGGCGA
CGACGTGCTGGTTCACCTGCTGGCACGCTGCGCGCTCTTTGTGCTGGTGGCTCCCAGCTGCGC
CTACCAGGTGTGCGGGCCGCCGCTGTACCAGCTCGGCGCTGCCACTCAGGCCCGGCCCCCGC
CACACGCTAGTGGACCCCGAAGGCGTCTGGGATGCGAACGGGCCTGGAACCATAGCGTCAGGG
AGGCCGGGGTCCCCCTGGGCCTGCCAGCCCCGGGTGCGAGGAGGCGCGGGGGCAGTGCCAG
CCGAAGTCTGCCGTTGCCCAAGAGGCCGAGGCGTGGCGCTGCCGCTGAGGCGGAGGGGAGGC
CCGTTGGGCAGGGGTCCTGGGCCCACCCGGGCAGGACGCGTGGACCGAGTGACCGTGGTTTCT
GTGTGGTGTCACCTGCCAGACCCGCCGAAGAAGCCACCTCTTTGGAGGGTGCGCTCTCTGGCAC
GCGCCACTCCCACCCATCCGTGGGCCGCCAGCACCACGCGGGCCCCCCATCCACATCGCGGCC
ACCACGTCCCTGGGACACGCCTTGTCCCCGGTGTACGCCGAGACCAAGCACTTCCTCTACTCC
TCAGGCGACAAGGAGCAGCTGCGGCCCTCCTTCCTACTCAGCTCTCTGAGGCCCAGCCTGACTG
GCGCTCGGAGGCTCGTGGAGACCATCTTTCTGGGTTCCAGGCCCTGGATGCCAGGGACTCCCC
GCAGGTTGCCCCGCCTGCCCCAGGGCTACTGGCAAATGCGGCCGCTGTTTCTGGAGCTGCTTG
GGAACCACGCGCAGTGCCCCTACGGGGTGCTCCTCAAGACGCACTGCCCGCTGCGAGCTGCGG
TCACCCCAGCAGCCGGTGTCTGTGCCCGGGAGAAGCCCCAGGGCTCTGTGGCGGCCCCCGAG
GAGGAGGACACAGACCCCCGTCGCCTGGTGCAGCTGCTCCGCCAGCACAGCAGCCCCTGGCAG
GTGTAGGGCTTCGTGCGGGCCTGCCTGCGCCGGCTGGTGCCGCCAGGCCTCTGGGGCTCCAG
GCACAACGAACGCCGCTTCCTCAGGAACACCAAGAAGTTCATCTCCCTGGGGAAGCATGCCAAG
CTCTCGCTGCAGGAGCTGACGTGGAAGATGAGCGTGCGGGGCTGCGCTTGGCTGCGCAGGAGC
CCAGGGGTTGGCTGTGTTCCGGCCGCAGAGCACCGTCTGCGTGAGGAGATCCTGGCCAAGTTC
CTGCACTGGCTGATGAGTGTGTACGTCGTCGAGCTGCTGAGGTCTTTCTTTTATGTCAGGGAGAG
CACGTTTCAAAAGAACAGGCTCTTTTTCTACCGGAAGAGTGTCTGGAGCAAGTTGCAAAGCATTG
GAATCAGACAGCACTTGAAGAGGGTGCAGCTGCGGGAGCTGTCGGAAGCAGAGGTCAGGCAGC
ATCGGGAAGCCAGGCCCGCCCTGCTGACGTCCAGACTCCGCTTCATCCCCAAGCCTGACGGGC
TGCGGCCGATTGTGAACATGGACTACGTCGTGGGAGCCAGAACGTTCCGCAGAGAAAAGAGGG
CCGAGCGTCTCACCTCCAGGGTGAAGGCACTGTTCAGCGTGCTCAACTACGAGCGGGCGCGGC
GCCCCGGCCTCCTGGGCGCCTCTGTGCTGGGCCTGGACGATATCCACAGGGCCTGGCGCACCT
TCGTGCTGCGTGTGCGGGCCCAGGACCCGCCGCCTGAGCTGTACTTTGTCAAGGTGGATGTGA
CGGGCGCGTACGACACCATCCCCCAGGACAGGCTCACGGAGGTCATCGCCAGCATCATCAAAC
CCCAGAACACGTACTGCGTGCGTCGGTATGCCGTGGTCCAGAAGGCCGCCCATGGGCACGTCC
GCAAGGCCTTCAAGAGCACGTCTCTACCTTGACAGACCTCCAGCCGTACATGCGACAGTTCGT
GGCTCACCTGCAGGAGACCAGCCCGCTGAGGGATGCCGTCGTCATCGAGCAGAGCTCCTCCCT
```

-continued

```
GAATGAGGCCAGCAGTGGCCTCTTCGACGTCTTCCTACGCTTCATGTGCCACCACGCCGTGCGC

ATCAGGGGCAAGTCCTACGTCCAGTGCCAGGGGATCCCGCAGGGCTCCATCCTCTCCACGCTG

CTCTGCAGCCTGTGCTACGGCGACATGGAGAACAAGCTGTTTGCGGGGATTCGGCGGGACGGG

CTGCTCCTGCGTTTGGTGGATGATTTCTTGTTGGTGACACCTCACCTCACCCACGCGAAAACCTT

CCTCAGGACCCTGGTCCGAGGTGTCCCTGAGTATGGCTGCGTGGTGAACTTGCGGAAGACAGTG

GTGAACTTCCCTGTAGAAGAGGAGGCCCTGGGTGGCAGGGCTTTTGTTGAGATGCCGGCCCAGG

GCCTATTCCCTGGTGCGGCCTGCTGCTGGATACCCGGACCCTGGAGGTGCAGAGCGACTACT

CCAGCTATGCCCGGACCTCCATCAGAGCCAGTCTCACCTTCAACCGCGGCTTCAAGGCTGGGAG

GAACATGCGTCGCAAACTCTTTGGGGTCTTGCGGCTGAAGTGTCACAGCCTGTTTCTGGATTTGC

AGGTGAAGAGCCTCCAGAGGGTGTGCACCAACATCTACAAGATCCTCCTGCTGCAGGCGTACAG

GTTTCACGCATGTGTGCTGCAGCTCCCATTTCATCAGCAAGTTTGGAAGAACCCCACATTTTTCCT

GCGCGTCATCTCTGACACGGCCTCCCTCTGCTACTCCATCCTGAAAGCCAAGAACGCAGGGATG

TCGCTGGGGGCCAAGGGCGCCGCCGGCCCTCTGCCCTCCGAGGCCGTGCAGTGGCTGTGCCA

CCAAGCATTCCTGCTCAAGCTGACTCGACACCGTGTCACCTACGTGCCACTCCTGGGGTCACTC

AGGACAGCCCAGACGCAGCTGAGTCGGAAGCTCCCGGGGACGACGCTGACTGCCCTGGAGGC

CGCAGCCAACCCGGCACTGCCCTCAGACTTCAAGACCATCCTGGACTGAGTCGAAACTCGCGGC

CGCATGCGTCGACGCGTATCGATGCATCTTAAGTAGATGTACCTTTAAGACCAATGACTTACAAG

GCAGCTGTAGATCTTAGCCACTTTTTAAAAGAAAAGGGGGACTGGAAGGGCTAATTCACTCCCA

ACGAAGACAAGATCTGCTTTTTGCTTGTACTGGGTCTCTCTGGTTAGACCAGATCTGAGCCTGGG

AGCTCTCTGGCTAACTAGGGAACCCACTGCTTAAGCCTCAATAAAGCTTGCCTTGAGTGCTTCAA

GTAGTGTGTGCCCGTCTGTTGTGTGACTCTGGTAACTAGAGATCCCTCAGACCCTTTTAGTCAGT

GTGGAAAATCTCTAGCAGTAGTAGTTCATGTCATCTTATTATTCAGTATTTATAACTTGCAAAGAAA

TGAATATCAGAGAGTGAGAGGAACTTGTTTATTGCAGCTTATAATGGTTACAAATAAAGCAATAGC

ATCACAAATTTCACAAATAAAGCATTTTTTCACTGCATTCTAGTTGTGGTTTGTCCAAACTCATCA

ATGTATCTTATCATGTCTGGCTCTAGCTATCCCGCCCCTAACTCCGCCCATCCCGCCCCTAACTC

CGCCCAGTTCCGCCCATTCTCCGCCCCATGGCTGACTAATTTTTTTATTTATGCAGAGGCCGAG

GCCGCCTCGGCCTCTGAGCTATTCCAGAAGTAGTGAGGAGGCTTTTTGGAGGCCTAGGGACGT

ACCCAATTCGCCCTATAGTGAGTCGTATTACGCGCGCTCACTGGCCGTCGTTTTACAACGTCGTG

ACTGGGAAAACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAATGGCGAAT

GGGACGCGCCCTGTAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGG

AACAACACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGCTTACAA

TTTAGGTGGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAAGGAAGAG

TATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTT
```

-continued

```
ACATCGAACTGGATCTCAACAGCGGTAAGATCCTTGAGAGTTTTCGCCCCGAAGAACGTTTTCCA

ATGATGAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAAC

ACTGCGGCCAACTTACTTCTGACAACGATCGGAGGACCGAAGGAGCTAACCGCTTTTTTGCACAA

CATGGGGATCATGTAACTCGCCTTGATCGTTGGGAACCGGAGCTGAATGAAGCCATACCAAAC

GACGAGCGTGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGGGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGGCGGAGCCTATGGA

AAAACGCCAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT
```

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating an age-related disorder in a subject comprising administering to the subject a nucleic acid vector comprising a coding sequence for telomerase reverse transcriptase (TERT), wherein the coding sequence is for human TERT and the vector expresses functional human TERT when present in a human cell.

2. The method of claim 1, wherein the vector further comprises a coding sequence for telomerase RNA (TR).

3. The method of claim 1, wherein the method is a gene therapy method.

4. The method of claim 1, wherein the nucleic acid sequence encoding TERT is operably linked to a regulatory sequence that drives expression of the coding sequence.

5. The method of claim 4, wherein the vector is a non-integrative vector.

6. The method of claim 4, wherein the vector is an adeno-associated virus-based vector.

7. The method of claim 4, wherein the vector is an lentivirus-based vector.

8. The method of claim 1, wherein the vector is represented by one of the following formulae:
LITR-U1-TR-CMV-TERT-SV40pA-RITR
LTR-CMV-TERT-SV40-Puro-CMV-AmCyan-LTR
LTR-U1-TR-PGK-BSD-CMV-TERT-LTR
LTR-PGK-BSD-CMV-TSS-TERT-LTR
or an active fragment or functional equivalent thereof.

9. The method of claim 8, wherein the vector is selected from pSSI14342, pSSI10902, pSSI12112 and pSSI12307.

10. The method of claim 1, wherein the method elicits an increase in lifespan in the subject.

11. A nucleic acid vector comprising a coding sequence for functional telomerase reverse transcriptase (TERT), wherein the coding sequence is for human TERT and the vector expresses functional human TERT when present in a human cell.

12. The vector of claim 11, wherein the vector further comprises a coding sequence for telomerase RNA (TR).

13. The vector of claim 11, wherein the functional equivalent is a nucleic acid having at least 80% or more sequence identity to human TERT.

14. The vector of claim 11, wherein the nucleic acid sequence encoding TERT is operably linked to a regulatory sequence capable of driving expression of the coding sequence.

15. The vector of claim 14, wherein the regulatory sequence comprises the cytomegalovirus (CMV) promoter.

16. The vector of claim 14, wherein the vector is a non-integrative vector.

17. The vector of claim 14, wherein the vector is an adeno-associated virus-based vector.

* * * * *

SEQUENCE LISTING

<160> NUMBER OF SEQ ID NOS: 3

<210> SEQ ID NO 1
<211> LENGTH: 38420
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (2450)..(2450)
<223> OTHER INFORMATION: n is a, c, g, or t

<400> SEQUENCE: 1

```
tcacagaacc ctagtattca acctgccacc tccctcccaa cacacagagt acacagtcct      60
ttctccccgg ctggccttaa aaagcatcat atcatgggta acagacatat tcttaggtgt     120
tatattccac acggtttcct gtcgagccaa acgctcatca agtgatatta ataaactccc     180
cgggcagctc acttaagttc atgtcgctgt ccagctgctg agccacaggc tgctgtccaa     240
cttgcggttg cttaacgggc ggcgaaggag aagtccacgc tacatggggg ggagagtcat     300
aatcgtgcat caggataggg cggtggtgct gcagcagcgc gcgaataaac tgctgccgcc     360
gccgctccgt cctgcaggaa tacaacatgg cagtggtctc ctcagcgatg attcgcaccg     420
cccgcagcat aaggcgcttg tcctccgggc acagcagcgc accctgatct cacttaaatc     480
agcacagtaa ctgcagcaca gcaccacaat attgttcaaa atcccacagt gcaaggcgct     540
gtatccaaag ctcatggcgg ggaccacaga acccacgtgg ccatcatacc acaagcgcag     600
gtagattaag tggcgacccc tcataaacac gctggacata acattaccct cttttggcat     660
gttgtaattc accacctccc ggtaccatat aaacctctga ttaaacatgg cgccatccac     720
caccatccta aaccagctgg ccaaaacctg ccccgccggg ntatacactg cagggaaccg     780
ggacttggac aatgacaagt gggagagccc aggactcgta accatggatc atcatgctcg     840
tcatgatatc aatgttggca caacacaggc acacgtgcat acacttcctc aggattacaa     900
gctcctcccg cgttagaacc atatcccagg gaacaaccca ttcctgaatc agcgtaaatc     960
ccacactgca gggaagacct cgcacgtaac tcacgttgtg cattgtcaaa gtgttacatt    1020
cgggcagcag cggatgatcc tccagtatgg tagcgcgggt ttctgtctca aaaggaggta    1080
gacgatccct actgtacgga gtgcgccgag acaaccgaga tcgtgttggt cgtagtgtca    1140
tgccaaatgg aacgccggac gtagtcatat ttcctgaagc aaaaccaggt gcgggcgtga    1200
caaacagatc tgcgtctccg gtctcgccgc ttagatcgct ctgtgtagta gttgtagtat    1260
atccactctc tcaaagcatc caggcgcccc ctggcttcgg gttctatgta aactccttca    1320
tgcgccgctg ccctgataac atccaccacc gcagaataag ccacacccag ccaacctaca    1380
cattcgttct gcgagtcaca cacgggagga gcgggaagag ctggaagaac catgttttt     1440
tttttattcc aaaagattat ccaaaacctc aaaatgaaga tctattaagt gaacgcgctc    1500
ccctccggtg gcgtggtcaa actctacagc caaagaacag ataatggcat ttgtaagatg    1560
ttgcacaatg gcttccaaaa ggcaaacggc cctcacgtcc aagtggacgt aaaggctaaa    1620
cccttcaggg tgaatctcct ctataaacat tccagcacct tcaaccatgc ccaaataatt    1680
ctcatctcgc caccttctca atatatctct aagcaaatcc gaatattta agtccgggcc     1740
attgtaaaaa atttggctcc agagcgccct ccaccttcag cctcaagcag cgaatcatga    1800
```

```
ttgcaaaaat tcaggttcct cacagacctg tataagattc aaaagcggaa cattaacaaa    1860
aataccgcga tcccgtaggt cccttcgcag ggccagctga acataatcgt gcaggtctgc    1920
acggaccagc gcggccactt ccccgccagg aaccatgaca aaagaaccca cactgattat    1980
gacacgcata ctcggagcta tgctaaccag cgtagccccg atgtaagctt gttgcatggg    2040
cggcgatata aaatgcaagg tgctgctcaa aaatcaggc aaagcctcgc gcaaaaaga     2100
aagcacatcg tagtcatgct catgcagata aaggcaggta agctccggaa ccaccacaga    2160
aaaagacacc attttctct caaacatgtc tgcgggtttc tgcataaaca caaaataaaa     2220
taacaaaaaa acatttaaac attagaagcc tgtcttacaa caggaaaaac aaccctttata   2280
agcataagac ggactacggc catgccggcg tgaccgtaaa aaaactggtc accgtgatta    2340
aaaagcacca ccgacagctc ctcggtcagt ccggagtcat aatgtaagac tcggtaaaca    2400
catcaggttg attcacatcg gtcagtgtta aaaagcgacc gaaatagccn ggggaatac     2460
aatacccgca ggcgtagaga caacattaca gcccccatag gaggtataac aaaattaata    2520
ggagagaaaa acacataaac acctgaaaaa ccctcctgcc taggcaaaat agcaccctcc    2580
cgctccagaa caacatacag cgcttccaca gcggcagcca taacagtcag ccttaccagt    2640
aaaaagaaa acctattaaa aaaacaccac tcgacacggc accagctcaa tcagtcacag     2700
tgtaaaaaag gccaagtgc agagcgagta tatataggac taaaaaatga cggtaacggt     2760
taaagtccac aaaaaacacc cagaaaaccg cacgcgaacc tacgcccaga acgaaagcc     2820
aaaaaaccca caacttcctc aaatcgtcac ttccgttttc ccacgttacg tcacttccca    2880
tttttaagaaa actacaattc ccaacacata caagttactc cgccctaaaa cctacgtcac   2940
ccgccccgtt cccacgcccc gcgccacgtc acaaactcca ccccctcatt atcatattgg    3000
cttcaatcca aaataaggta tattattgat gatgttaatt aacatgcatg gatccatatg    3060
cggtgtgaaa taccgcacag atgcgtaagg agaaaatacc gcatcaggcg ctcttccgct    3120
tcctcgctca ctgactcgct gcgctcggtc gttcggctgc ggcgagcggt atcagctcac    3180
tcaaaggcgg taatacggtt atccacagaa tcagggggata acgcaggaaa gaacatgtga    3240
gcaaaaggcc agcaaaaggc caggaaccgt aaaaaggccg cgttgctggc gttttttccat   3300
aggctccgcc cccctgacga gcatcacaaa aatcgacgct caagtcagag gtggcgaaac    3360
ccgacaggac tataaagata ccaggcgttt ccccctggaa gctccctcgt gcgctctcct    3420
gttccgaccc tgccgcttac cggatacctg tccgcctttc tcccttcggg aagcgtggcg    3480
ctttctcata gctcacgctg taggtatctc agttcggtgt aggtcgttcg ctccaagctg    3540
ggctgtgtgc acgaaccccc cgttcagccc gaccgctgcg ccttatccgg taactatcgt    3600
cttgagtcca acccggtaag acacgactta tcgccactgg cagcagccac tggtaacagg    3660
attagcagag cgaggtatgt aggcggtgct acagagttct tgaagtggtg gcctaactac    3720
ggctacacta aaggacagt atttggtatc tgcgctctgc tgaagccagt taccttcgga    3780
aaaagagttg gtagctcttg atccggcaaa caaaccaccg ctggtagcgg tggtttttttt   3840
gtttgcaagc agcagattac gcgcagaaaa aaggatctc aagaagatcc tttgatcttt     3900
tctacggggt ctgacgctca gtggaacgaa aactcacgtt aagggatttt ggtcatgaga    3960
ttatcaaaaa ggatcttcac ctagatcctt ttaaattaaa aatgaagttt taaatcaatc    4020
taaagtatat atgagtaaac ttggtctgac agttaccaat gcttaatcag tgaggcacct    4080
atctcagcga tctgtctatt tcgttcatcc atagttgcct gactccccgt cgtgtagata    4140
```

```
actacgatac gggagggctt accatctggc cccagtgctg caatgatacc gcgagaccca   4200
cgctcaccgg ctccagattt atcagcaata aaccagccag ccggaagggc cgagcgcaga   4260
agtggtcctg caactttatc cgcctccatc cagtctatta attgttgccg ggaagctaga   4320
gtaagtagtt cgccagttaa tagtttcgcg aacgttgttg ccattgctgc agccatgaga   4380
ttatcaaaaa ggatcttcac ctagatcctt ttcacgtaga aagccagtcc gcagaaacgg   4440
tgctgacccc ggatgaatgt cagctactgg gctatctgga caagggaaaa cgcaagcgca   4500
aagagaaagc aggtagcttg cagtgggctt acatggcgat agctagactg gcggttttta   4560
tggacagcaa gcgaaccgga attgccagct ggggcgccct ctggtaaggt tgggaagccc   4620
tgcaaagtaa actggatggc tttcttgccg ccaaggatct gatggcgcag gggatcaagc   4680
tctgatcaag agacaggatg aggatcgttt cgcatgattg aacaagatgg attcacgca   4740 ggttctccgg ccgcttgggt ggagaggcta ttcggctatg actgggcaca acagacaatc   4800
ggctgctctg atgccgccgt gttccggctg tcagcgcagg ggcgcccggt tcttttttgtc   4860 aagaccgacc tgtccggtgc cctgaatgaa ctgcaagacg aggcagcgcg gctatcgtgg   4920
ctggccacga cgggcgttcc ttgcgcagct gtgctcgacg ttgtcactga agcgggaagg   4980
gactggctgc tattgggcga agtgccgggg caggatctcc tgtcatctca ccttgctcct   5040
gccgagaaag tatccatcat ggctgatgca atgcggcggc tgcatacgct tgatccggct   5100
acctgcccat tcgaccacca agcgaaacat cgcatcgagc gagcacgtac tcggatggaa   5160
gccggtcttg tcgatcagga tgatctggac gaagagcatc aggggctcgc gccagccgaa   5220
ctgttcgcca ggctcaaggc gagcatgccc gacggcgagg atctcgtcgt gacccatggc   5280
gatgcctgct tgccgaatat catggtggaa aatggccgct tttctggatt catcgactgt   5340
ggccggctgg gtgtggcgga ccgctatcag gacatagcgt tggctacccg tgatattgct   5400
gaagagcttg gcggcgaatg ggctgaccgc ttcctcgtgc tttacggtat cgccgctccc   5460
gattcgcagc gcatcgcctt ctatcgcctt cttgacgagt tcttctgaat tttgttaaaa   5520 ttttttgttaa atcagctcat ttttttaacca ataggccgaa atcggcaaca tcccttataa   5580
atcaaaagaa tagaccgcga tagggttgag tgttgttcca gtttggaaca agagtccact   5640
attaaagaac gtggactcca acgtcaaagg gcgaaaaacc gtctatcagg gcgatggccc   5700
actacgtgaa ccatcaccca aatcaagttt tttgcggtcg aggtgccgta aagctctaaa   5760
tcggaaccct aaagggagcc cccgatttag agcttgacgg ggaaagccgg cgaacgtggc   5820
gagaaaggaa gggaagaaag cgaaaggagc gggcgctagg gcgctggcaa gtgtagcggt   5880
cacgctgcgc gtaaccacca cacccgcgcg cttaatgcgc cgctacaggg cgcgtccatt   5940
cgccattcag gatcgaatta attcttaatt aacatcatca ataatatacc ttattttgga   6000
ttgaagccaa tatgataatg aggggggtgga gtttgtgacg tggcgcgggg cgtgggaacg   6060
gggcgggtga cgtagtagtg tggcggaagt gtgatgttgc aagtgtggcg gaacacatgt   6120
aagcgacgga tgtggcaaaa gtgacgtttt tggtgtgcgc cggtgtacac aggaagtgac   6180
aattttcgcg cggttttagg cggatgttgt agtaaatttg ggcgtaaccg agtaagattt   6240
ggccattttc gcgggaaaac tgaataagag gaagtgaaat ctgaataatt ttgtgttact   6300
catagcgcgt aatactggta ccgcggccgc ctcgagtcta gagatatcga attcaagctt   6360
aaggtgcacg gcccacgtgg ccactagtaa ttttttctgca gaaaacgtac ccggggatcc   6420
tctaggatcc caccgaaagg ttgctcctta acacaggcta aggaccagct tctttgggag   6480
agaacagacg caggggcggg agggaaaaag ggagaggcag acgtcacttc cccttggcgg   6540
```

```
ctctggcagc agattggtcg gttgagtggc agaaaggcag acgggactg ggcaaggcac    6600 tgtcggtgac atcacggaca gggcgacttc tatgtagatg aggcagcgca gaggctgctg    6660
cttcgccact tgctgcttcg ccacgaagga gttcccgtgc cctgggagcg ggttcaggac    6720
cgcggatcgg aagtgagaat cccagctgtg tgtcagggct ggaaagggct cgggagtgcg    6780
cggggcaagt gaccgtgtgt gtaaagagtg aggcgtatga ggctgtgtcg gggcagagcc    6840
cgaagatccg ggttgcggag ggtgggcctg ggaggggtgg tggccatttt ttgtctaacc    6900
ctaactgaga agggcgtagg cgccgtgctt ttgctccccg cgcgctgttt ttctcgctga    6960 cttttcagcgg gcgaaaaagc ctcggcctgc cgccttccac cgttcattct agagcaaaca    7020
aaaaatgtca gctgctggcc cgttcgcccc tcccggggac ctgcggcggg tcgcctgccc    7080
agcccccgaa ccccgcctgg aggcgcggt cggcccgggg cttctccgga ggcacccact    7140
gccaccgcga agagttgggc tctgtcagcc gcgggtctct cgggggcgag ggcgaggttc    7200 aggccttca ggccgcagga agaggaacgg agcgagtccc cgcgcgcggc gcgattccct    7260
gagctgtggg acgtgcaccc aggactcggc tcacacatgc agttcgcttt cctgttggtg    7320
gggggaacgc cgatcgtgcg catccgtcac ccctcgccgg caatgggggc ttgtgaaccc    7380
ccaaacctga ctgactgggc cagtgtgctg caaattggca ggagacgtga aggcacctcc    7440
aaagtcgact ttctggagtt tcaaaaacag accgtacgat gcattagtta ttaatagtaa    7500
tcaattacgg ggtcattagt tcatagccca tatatggagt tccgcgttac ataacttacg    7560
gtaaatggcc cgcctggctg accgcccaac gacccccgcc cattgacgtc aataatgacg    7620
tatgttccca tagtaacgcc aatagggact ttccattgac gtcaatgggt ggagtattta    7680
cggtaaactg cccacttggc agtacatcaa gtgtatcata tgccaagtac gccccctatt    7740
gacgtcaatg acggtaaatg gcccgcctgg cattatgccc agtacatgac cttatgggac    7800
tttcctactt ggcagtacat ctacgtatta gtcatcgcta ttaccatggt gatgcggttt    7860
tggcagtaca tcaatgggcg tggatagcgg tttgactcac ggggatttcc aagtctccac    7920
cccattgacg tcaatgggag tttgttttgg caccaaaatc aacgggactt tccaaaatgt    7980
cgtaacaact ccgccccatt gacgcaaatg ggcggtaggc gtgtacggtg ggaggtctat    8040
ataagcagag ctggtttagt gaaccgtcag atccgctagc ccaccatgc cgcgcgctcc    8100 ccgctgccga gccgtcgct ccctgctgcg cagccactac cgcgaggtgc tgccgctggc    8160
cacgttcgtg cggcgcctgg ggccccaggg ctggcggctg gtgcagcgcg gggacccggc    8220
ggctttccgc gcgctggtgg cccagtgcct ggtgtgcgtg ccctgggacg cacggccgcc    8280
ccccgccgcc ccctccttcc gccaggtgtc ctgcctgaag gagctggtgg cccgagtgct    8340
gcagaggctg tgcgagcgcg gcgcgaagaa cgtgctggcc ttcggcttcg cgctgctgga    8400
cgggccccgc gggggccccc ccgaggcctt caccaccagc gtgcgcagct acctgcccaa    8460
cacggtgacc gacgcactgc gggggagcgg ggcgtggggg ctgctgttgc gccgcgtggg    8520
cgacgacgtg ctggttcacc tgctggcacg ctgcgcgctc tttgtgctgg tggctcccag    8580
ctgcgcctac caggtgtgcg ggccgccgct gtaccagctc ggcgctgcca ctcaggcccg    8640
gcccccgcca cacgctagtg gaccccgaag gcgtctggga tgcgaacggg cctggaacca    8700
tagcgtcagg gaggccgggg tccccctggg cctgccagcc ccgggtgcga ggaggcgcgg    8760
gggcagtgcc agccgaagtc tgccgttgcc caagaggccc aggcgtggcg ctgccctga    8820 gccggagcgg acgcccgttg ggcaggggtc ctggccccac ccgggcagga cgcgtggacc    8880
```

```
gagtgaccgt ggtttctgtg tggtgtcacc tgccagaccc gccgaagaag ccacctcttt    8940
ggagggtgcg ctctctggca cgcgccactc ccacccatcc gtgggccgcc agcaccacgc    9000
gggcccccca tccacatcgc ggccaccacg tccctgggac acgccttgtc ccccggtgta    9060
cgccgagacc aagcacttcc tctactcctc aggcgacaag gagcagctgc ggccctcctt    9120
cctactcagc tctctgaggc ccagcctgac tggcgctcgg aggctcgtgg agaccatctt    9180
tctgggttcc aggccctgga tgccagggac tccccgcagg ttgccccgcc tgcccccagcg   9240
ctactggcaa atgcggcccc tgtttctgga gctgcttggg aaccacgcgc agtgcccta    9300
cggggtgctc ctcaagacgc actgcccgct gcgagctgcg gtcacccag cagccggtgt     9360
ctgtgcccgg gagaagcccc agggctctgt ggcggccccc gaggaggagg acacagaccc   9420
ccgtcgcctg gtgcagctgc tccgccagca cagcagcccc tggcaggtgt acggcttcgt    9480
gcgggcctgc ctgcgccggc tggtgccccc aggcctctgg ggctccaggc acaacgaacg   9540
ccgcttcctc aggaacacca agaagttcat ctccctgggg aagcatgcca agctctcgct    9600
gcaggagctg acgtggaaga tgagcgtgcg gggctgcgct tggctgcgca ggagcccagg   9660
ggttggctgt gttccggccg cagagcaccg tctgcgtgag gagatcctgg ccaagttcct    9720
gcactggctg atgagtgtgt acgtcgtcga gctgctcagg tctttctttt atgtcacgga    9780
gaccacgttt caaaagaaca ggctcttttt ctaccggaag agtgtctgga gcaagttgca    9840
aagcattgga atcagacagc acttgaagag ggtgcagctg cggagctgt cggaagcaga     9900
ggtcaggcag catcgggaag ccaggcccgc cctgctgacg tccagactcc gcttcatccc    9960
caagcctgac gggctgcggc cgattgtgaa catggactac gtcgtgggag ccagaacgtt   10020
ccgcagagaa aagagggccg agcgtctcac ctccagggtg aaggcactgt tcagcgtgct   10080
caactacgag cgggcgcggc gccccggcct cctgggcgcc tctgtgctgg gcctggacga   10140
tatccacagg gcctggcgca ccttcgtgct gcgtgtgcgg gcccaggacc gccgcctga    10200
gctgtacttt gtcaaggtgg atgtgacggg cgcgtacgac accatccccc aggacaggct   10260
cacggaggtc atcgccagca tcatcaaacc ccagaacacg tactgcgtgc gtcggtatgc   10320
cgtggtccag aaggccgccc atgggcacgt ccgcaaggcc ttcaagagcc acgtctctac   10380
cttgacagac ctccagccgt acatgcgaca gttcgtggct cacctgcagg agaccagccc   10440
gctgagggat gccgtcgtca tcgagcagag ctcctccctg aatgaggcca gcagtggcct   10500
cttcgacgtc ttcctacgct tcatgtgcca ccacgccgtg cgcatcaggg gcaagtccta   10560
cgtccagtgc cagggggatcc cgcagggctc catcctctcc acgctgctct gcagcctgtg   10620
ctacggcgac atggagaaca agctgttttgc ggggattcgg cgggacgggc tgctcctgcg   10680
tttggtggat gatttcttgt tggtgacacc tcacctcacc cacgcgaaaa ccttcctcag   10740
gaccctggtc cgaggtgtcc ctgagtatgg ctgcgtggtg aacttgcgga agacagtggt   10800
gaacttccct gtagaagacg aggccctggg tggcacggct tttgttcaga tgccggccca   10860
cggcctattc ccctggtgcg gcctgctgct ggatacccgg accctggagg tgcagagcga   10920
ctactccagc tatgcccgga cctccatcag agccagtctc accttcaacc gcggcttcaa   10980
ggctgggagg aacatgcgtc gcaaactctt tgggtcttg cggctgaagt gtcacagcct    11040
gtttctggat ttgcaggtga acagcctcca gacggtgtgc accaacatct acaagatcct   11100
cctgctgcag gcgtacaggt ttcacgcatg tgtgctgcag ctcccatttc atcagcaagt   11160
ttggaagaac cccacatttt tcctgcgcgt catctctgac acggcctccc tctgctactc   11220
catcctgaaa gccaagaacg cagggatgtc gctgggggcc aagggcgccg ccggccctct   11280
```

```
gccctccgag gccgtgcagt ggctgtgcca ccaagcattc ctgctcaagc tgactcgaca    11340
ccgtgtcacc tacgtgccac tcctggggtc actcaggaca gcccagacgc agctgagtcg    11400
gaagctcccg gggacgacgc tgactgccct ggaggccgca gccaacccgg cactgccctc    11460
agacttcaag accatcctgg actgagtcga aactcgcggc cgccatatgc atcctaggcc    11520
tattaatatt ccggagtata cgtagccggc taacgttaac ttgtttattg cagcttataa    11580
tggttacaaa taaagcaata gcatcacaaa tttcacaaat aaagcatttt ttcactgca    11640 ttctagttgt ggtttgtcca aactcatcaa tgtatcttaa cgcggatctg ggcgtggtta    11700
agggtgggaa agaatatata aggtgggggt cttatgtagt tttgtatctg ttttgcagca    11760
gccgccgccg ccatgagcac caactcgttt gatggaagca ttgtgagctc atatttgaca    11820
acgcgcatgc ccccatgggc cggggtgcgt cagaatgtga tgggctccag cattgatggt    11880
cgccccgtcc tgcccgcaaa ctctactacc ttgacctacg agaccgtgtc tggaacgccg    11940
ttggagactg cagcctccgc cgccgcttca gccgctgcag ccaccgcccg cgggattgtg    12000
actgactttg ctttcctgag cccgcttgca agcagtgcag cttcccgttc atccgcccgc    12060
gatgacaagt tgacggctct tttggcacaa ttggattctt tgacccggga acttaatgtc    12120
gtttctcagc agctgttgga tctgcgccag caggtttctg ccctgaaggc ttcctcccct    12180
cccaatgcgg tttaaaacat aaataaaaaa ccagactctg tttggatttg atcaagcaa    12240 gtgtcttgct gtctttattt aggggttttg cgcgcgcggt aggcccggga ccagcggtct    12300
cggtcgttga gggtcctgtg tattttttcc aggacgtggt aaaggtgact ctggatgttc    12360
agatacatgg gcataagccc gtctctgggg tggaggtagc accactgcag agcttcatgc    12420
tgcggggtgg tgttgtagat gatccagtcg tagcaggagc gctgggcgtg gtgcctaaaa    12480
atgtctttca gtagcaagct gattgccagg ggcaggccct tggtgtaagt gtttacaaag    12540
cggttaagct gggatgggtg catacgtggg gatatgagat gcatcttgga ctgtatttt    12600 aggttggcta tgttcccagc catatccctc cggggattca tgttgtgcag aaccaccagc    12660
acagtgtatc cggtgcactt gggaaatttg tcatgtagct tagaaggaaa tgcgtggaag    12720
aacttggaga cgcccttgtg acctccaaga ttttccatgc attcgtccat aatgatggca    12780
atgggcccac gggcggcggc ctgggcgaag atatttctgg gatcactaac gtcatagttg    12840
tgttccagga tgagatcgtc ataggccatt tttacaaagc gcgggcggag ggtgccagac    12900
tgcggtataa tggttccatc cggcccaggg gcgtagttac cctcacagat ttgcatttcc    12960
cacgctttga gttcagatgg ggggatcatg tctacctgcg gggcgatgaa gaaaacggtt    13020
tccggggtag gggagatcag ctgggaagaa agcaggttcc tgagcagctg cgacttaccg    13080
cagccggtgg gcccgtaaat cacacctatt accgggtgca actggtagtt aagagagctg    13140
cagctgccgt catccctgag cagggggggcc acttcgttaa gcatgtccct gactcgcatg    13200 ttttcccctga ccaaatccgc cagaaggcgc tcgccgccca gcgatagcag ttcttgcaag    13260
gaagcaaagt ttttcaacgg tttgagaccg tccgccgtag gcatgctttt gagcgtttga    13320
ccaagcagtt ccaggcggtc ccacagctcg gtcacctgct ctacggcatc tcgatccagc    13380
atatctcctc gtttcgcggg ttggggcggc tttcgctgta cggcagtagt cggtgctcgt    13440
ccagacgggc cagggtcatg tctttccacg ggcgcagggt cctcgtcagc gtagtctggg    13500
tcacggtgaa ggggtgcgct ccgggctgcg cgctggccag ggtgcgcttg aggctggtcc    13560
tgctggtgct gaagcgctgc cggtcttcgc cctgcgcgtc ggccaggtag catttgacca    13620
```

```
tggtgtcata gtccagcccc tccgcggcgt ggcccttggc gcgcagcttg cccttggagg   13680
aggcgccgca cgaggggcag tgcagacttt tgagggcgta gagcttgggc gcgagaaata   13740
ccgattccgg ggagtaggca tccgcgccgc aggccccgca gacggtctcg cattccacga   13800
gccaggtgag ctctggccgt tcggggtcaa aaaccaggtt tcccccatgc tttttgatgc   13860
gtttcttacc tctggtttcc atgagccggt gtccacgctc ggtgacgaaa aggctgtccg   13920
tgtccccgta tacagacttg agaggcctgt cctcgagcgg tgttccgcgg tcctcctcgt   13980
atagaaactc ggaccactct gagacaaagg ctcgcgtcca ggccagcacg aaggaggcta   14040
agtgggaggg gtagcggtcg ttgtccacta ggggtccac tcgctccagg gtgtgaagac    14100
acatgtcgcc ctcttcggca tcaaggaagg tgattggttt gtaggtgtag gccacgtgac   14160
cgggtgttcc tgaaggggg ctataaaagg gggtggggc gcgttcgtcc tcactctctt    14220
ccgcatcgct gtctgcgagg gccagctgtt ggggtgagta ctccctctga aaagcgggca   14280
tgacttctgc gctaagattg tcagtttcca aaaacgagga ggatttgata ttcacctggc   14340
ccgcggtgat gcctttgagg gtggccgcat ccatctggtc agaaaagaca atcttttgt    14400 tgtcaagctt ggtggcaaac gacccgtaga gggcgttgga cagcaacttg gcgatggagc   14460
gcagggtttg gttttttgtcg cgatcggcgc gctcccttggc cgcgatgttt agctgcacgt  14520
attcgcgcgc aacgcaccgc cattcgggaa agacggtggt gcgctcgtcg ggcaccaggt   14580
gcacgcgcca accgcggttg tgcagggtga caaggtcaac gctggtggct acctctccgc   14640
gtaggcgctc gttggtccag cagaggcggc cgcccttgcg cgagcagaat ggcggtaggg   14700
ggtctagctg cgtctcgtcc ggggggtctg cgtccacggt aaagaccccg ggcagcaggc   14760
gcgcgtcgaa gtagtctatc ttgcatcctt gcaagtctag cgcctgctgc catgcgcggg   14820
cggcaagcgc gcgctcgtat gggttgagtg ggggacccca tggcatgggg tgggtgagcg   14880
cggaggcgta catgccgcaa atgtcgtaaa cgtagagggg ctctctgagt attccaagat   14940
atgtagggta gcatcttcca ccgcggatgc tggcgcgcac gtaatcgtat agttcgtgcg   15000
agggagcgag gaggtcggga ccgaggttgc tacgggcggg ctgctctgct cggaagacta   15060
tctgcctgaa gatggcatgt gagttggatg atatggttgg acgctggaag acgttgaagc   15120
tggcgtctgt gagacctacc gcgtcacgca cgaaggaggc gtaggagtcg cgcagcttgt   15180
tgaccagctc ggcggtgacc tgcacgtcta gggcgcagta gtccagggtt tccttgatga   15240
tgtcatactt atcctgtccc ttttttttcc acagctcgcg gttgaggaca aactcttcgc   15300
ggtctttcca gtactcttgg atcggaaacc cgtcggcctc cgaacggtaa gagcctagca   15360
tgtagaactg gttgacggcc tggtaggcgc agcatccctt ttctacgggt agcgcgtatg   15420
cctgcgcggc cttccggagc gaggtgtggg tgagcgcaaa ggtgtccctg accatgactt   15480
tgaggtactg gtatttgaag tcagtgtcgt cgcatccgcc ctgctcccag agcaaaaagt   15540
ccgtgcgctt tttggaacgc ggatttggca gggcgaaggt gacatcgttg aagagtatct   15600
ttcccgcgcg aggcataaag ttgcgtgtga tgcgaaggg tccggcacc tcggaacggt     15660 tgttaattac ctgggcggcg agcacgatct cgtcaaagcc gttgatgttg tgcccacaa    15720 tgtaaagttc caagaagcgc gggatgccct tgatggaagg caattttta agttcctcgt    15780 aggtgagctc ttcaggggag ctgagcccgt gctctgaaag ggcccagtct gcaagatgag   15840
ggttggaagc gacgaatgag ctccacaggt cacgggccat tagcatttgc aggtggtcgc   15900
gaaaggtcct aaactggcga cctatggcca ttttttctgg ggtgatgcag tagaaggtaa    15960
gcgggtcttg ttcccagcgg tcccatccaa ggttcgcggc taggtctcgc gcggcagtca   16020
```

```
ctagaggctc atctccgccg aacttcatga ccagcatgaa gggcacgagc tgcttcccaa    16080
aggcccccat ccaagtatag gtctctacat cgtaggtgac aaagagacgc tcggtgcgag    16140
gatgcgagcc gatcgggaag aactggatct cccgccacca attggaggag tggctattga    16200
tgtggtgaaa gtagaagtcc ctgcgacggg ccgaacactc gtgctggctt ttgtaaaaac    16260
gtgcgcagta ctggcagcgg tgcacgggct gtacatcctg cacgaggttg acctgacgac    16320
cgcgcacaag gaagcagagt gggaatttga gccctcgcc tggcgggttt ggctggtggt    16380
cttctacttc ggctgcttgt ccttgaccgt ctggctgctc gagggagtt acggtggatc    16440 ggaccaccac gccgcgcgag cccaaagtcc agatgtccgc gcgcggcggt cggagcttga    16500
tgacaacatc gcgcagatgg gagctgtcca tggtctggag ctcccgcggc gtcaggtcag    16560
gcgggagctc ctgcaggttt acctcgcata gacgggtcag ggcgcgggct agatccaggt    16620
gatacctaat ttccaggggc tggttggtgg cggcgtcgat ggcttgcaag aggccgcatc    16680
cccgcggcgc gactacggta ccgcgcgcg ggcggtgggc cgcgggggtg tccttggatg    16740
atgcatctaa aagcggtgac gcgggcgagc ccccggaggt agggggggct ccggacccgc    16800
cgggagaggg ggcaggggca cgtcggcgcc gcgcgcgggc aggagctggt gctgcgcgcg    16860
taggttgctg gcgaacgcga cgacgcggcg gttgatctcc tgaatctggc gcctctgcgt    16920
gaagacgacg ggcccggtga gcttgagcct gaaagagagt tcgacagaat caatttcggt    16980
gtcgttgacg gcggcctggc gcaaaatctc ctgcacgtct cctgagttgt cttgataggc    17040
gatctcggcc atgaactgct cgatctcttc ctcctggaga tctccgcgtc cggctcgctc    17100
cacggtggcg gcgaggtcgt tggaaatgcg ggccatgagc tgcgagaagg cgttgaggcc    17160
tccctcgttc cagacgcggc tgtagaccac gcccccttcg gcatcgcggg cgcgcatgac    17220
cacctgcgcg agattgagct ccacgtgccg ggcgaagacg gcgtagtttc gcaggcgctg    17280
aaagaggtag ttgagggtgg tggcggtgtg ttctgccacg aagaagtaca taacccagcg    17340
tcgcaacgtg gattcgttga tatcccccaa ggcctcaagg cgctccatgg cctcgtagaa    17400
gtccacggcg aagttgaaaa actgggagtt gcgcgccgac acggttaact cctcctccag    17460
aagacggatg agctcggcga cagtgtcgcg cacctcgcgc tcaaaggcta caggggcctc    17520
ttcttcttct tcaatctcct cttccataag ggcctcccct tcttcttctt ctggcggcgg    17580 tggggaggg gggacacggc ggcgacgacg gcgcaccggg aggcggtcga caaagcgctc    17640
gatcatctcc ccgcggcgac ggcgcatggt ctcggtgacg gcgcggccgt tctcgcgggg    17700
gcgcagttgg aagacgccgc ccgtcatgtc ccggttatgg gttggcgggg ggctgccatg    17760
cggcagggat acggcgctaa cgatgcatct caacaattgt tgtgtaggta ctccgccgcc    17820
gagggacctg agcgagtccg catcgaccgg atcggaaaac ctctcgagaa aggcgtctaa    17880
ccagtcacag tcgcaaggta ggctgagcac cgtggcgggc ggcagcgggc ggcggtcggg    17940
gttgtttctg gcggaggtgc tgctgatgat gtaattaaag taggcggtct tgagacggcg    18000
gatggtcgac agaagcacca tgtccttggg tccggcctgc tgaatgcgca ggcggtcggc    18060
catgccccag gcttcgtttt gacatcggcg caggtctttg tagtagtctt gcatgagcct    18120
ttctaccggc acttcttctt ctccttcctc ttgtcctgca tctcttgcat ctatcgctgc    18180
ggcggcggcg gagtttggcc gtaggtggcg ccctcttcct cccatgcgtg tgaccccgaa    18240 gccctcatc ggctgaagca gggctaggtc ggcgacaacg cgctcggcta atatggcctg    18300
ctgcacctgc gtgagggtag actggaagtc atccatgtcc acaaagcggt ggtatgcgcc    18360
```

```
cgtgttgatg gtgtaagtgc agttggccat aacggaccag ttaacggtct ggtgacccgg   18420
ctgcgagagc tcggtgtacc tgagacgcga gtaagccctc gagtcaaata cgtagtcgtt   18480
gcaagtccgc accaggtact ggtatcccac caaaaagtgc ggcggcggct ggcggtagag   18540
gggccagcgt agggtggccg gggctccggg ggcgagatct tccaacataa ggcgatgata   18600
tccgtagatg tacctggaca tccaggtgat gccggcggcg gtggtggagg cgcgcggaaa   18660
gtcgcggacg cggttccaga tgttgcgcag cggcaaaaag tgctccatgg tcggacgct    18720 ctggccggtc aggcgcgcgc aatcgttgac gctctaccgt gcaaaggag agcctgtaag    18780 cgggcactct tccgtggtct ggtggataaa ttcgcaaggg tatcatgcg gacgaccggg    18840 gttcgagccc cgtatccggc cgtccgccgt gatccatgcg gttaccgccc gcgtgtcgaa   18900
cccaggtgtg cgacgtcaga caacggggga gtgctccttt tggcttcctt ccaggcgcgg   18960
cggctgctgc gctagctttt ttggccactg gccgcgcgca gcgtaagcgg ttaggctgga   19020
aagcgaaagc attaagtggc tcgctccctg tagccggagg gttatttccc aagggttgag   19080
tcgcgggacc cccggttcga gtctcggacc ggccggactg cggcgaacgg gggtttgcct   19140
ccccgtcatg caagacccg cttgcaaatt cctccggaaa cagggacgag ccccttttt    19200 gcttttccca gatgcatccg gtgctgcggc agatgcgccc ccctcctcag cagcggcaag   19260
agcaagagca gcggcagaca tgcagggcac cctcccctcc tcctaccgcg tcaggagggg   19320
cgacatccgc ggttgacgcg gcagcagatg gtgattacga accccgcgg cgcccgggccc   19380 ggcactacct ggacttggag gagggcgagg gcctggcgcg gctaggagcg ccctctcctg   19440
agcggtaccc aagggtgcag ctgaagcgtg atacgcgtga ggcgtacgtg ccgcggcaga   19500
acctgtttcg cgaccgcgag ggagaggagc ccgaggagat gcgggatcga aagttccacg   19560
cagggcgcga gctgcggcat ggcctgaatc gcgagcggtt gctgcgcgag gaggactttg   19620
agcccgacgc gcgaaccggg attagtcccg cgcgcgcaca cgtggcggcc gccgacctgg   19680
taaccgcata cgagcagacg gtgaaccagg agattaactt tcaaaaaagc tttaacaacc   19740
acgtgcgtac gcttgtggcg cgcgaggagg tggctatagg actgatgcat ctgtgggact   19800
ttgtaagcgc gctggagcaa aacccaaata gcaagccgct catggcgcag ctgttcctta   19860
tagtgcagca cagcagggac aacgaggcat tcagggatgc gctgctaaac atagtagagc   19920
ccgagggccg ctggctgctc gatttgataa acatcctgca gagcatagtg gtgcaggagc   19980
gcagcttgag cctggctgac aaggtggccg ccatcaacta ttccatgctt agcctgggca   20040
agttttacgc ccgcaagata taccatacc cttacgttcc catagacaag gaggtaaaga   20100 tcgagggggtt ctacatgcgc atggcgctga aggtgcttac cttgagcgac gacctgggcg   20160
tttatcgcaa cgagcgcatc cacaaggccg tgagcgtgag ccggcggcgc gagctcagcg   20220
accgcgagct gatgcacagc ctgcaaaggg ccctggctgg cacgggcagc ggcgatagag   20280
aggccgagtc ctactttgac gcgggcgctg acctgcgctg gccccaagcc gacgcgcccc   20340
tggaggcagc tggggccgga cctggctgg cgtggcacc cgcgcgcgct ggcaacgtcg   20400
gcggcgtgga ggaatatgac gaggacgatg agtacgagcc agaggacggc gagtactaag   20460
cggtgatgtt tctgatcaga tgatgcaaga cgcaacggac ccggcggtgc gggcggcgct   20520
gcagagccag ccgtccggcc ttaactccac ggacgactgg cgccaggtca tggaccgcat   20580
catgtcgctg actgcgcgca atcctgacgc gttccggcag cagccgcagg ccaaccggct   20640
ctccgcaatt ctggaagcgg tggtcccggc gcgcgcaaac cccacgcacg agaaggtgct   20700
ggcgatcgta aacgcgctgg ccgaaaacag ggccatccgg cccgacgagg ccggcctggt   20760
```

```
ctacgacgcg ctgcttcagc gcgtggctcg ttacaacagc ggcaacgtgc agaccaacct    20820
ggaccggctg gtgggggatg tgcgcgaggc cgtggcgcag cgtgagcgcg cgcagcagca    20880
gggcaacctg ggctccatgg ttgcactaaa cgccttcctg agtacacagc ccgccaacgt    20940
gccgcgggga caggaggact acaccaactt tgtgagcgca ctgcggctaa tggtgactga    21000
gacaccgcaa agtgaggtgt accagtctgg gccagactat tttttccaga ccagtagaca    21060
aggcctgcag accgtaaacc tgagccaggc tttcaaaaac ttgcaggggc gtgggggggt    21120
gcgggctccc acaggcgacc gcgcgaccgt gtctagcttg ctgacgccca actcgcgcct    21180
gttgctgctg ctaatagcgc ccttcacgga cagtggcagc gtgtcccggg acacatacct    21240
aggtcacttg ctgacactgt accgcgaggc cataggtcag gcgcatgtgg acgagcatac    21300
tttccaggag attacaagtg tcagccgcgc gctggggcag gaggacacgg gcagcctgga    21360
ggcaacccta aactacctgc tgaccaaccg gcggcagaag atccctcgt tgcacagttt     21420 aaacagcgag gaggagcgca ttttgcgcta cgtgcagcag agcgtgagcc ttaacctgat    21480
gcgcgacggg gtaacgccca gcgtggcgct ggacatgacc gcgcgcaaca tggaaccggg    21540
catgtatgcc tcaaaccggc cgtttatcaa ccgcctaatg gactacttgc atcgcgcggc    21600
cgccgtgaac cccgagtatt tcaccaatgc catcttgaac ccgcactggc taccgccccc    21660
tggtttctac accgggggat tcgaggtgcc cgagggtaac gatggattcc tctgggacga    21720
catagacgac agcgtgtttt ccccgcaacc gcagaccctg ctagagttgc aacagcgcga    21780
gcaggcagag gcggcgctgc gaaaggaaag cttccgcagg ccaagcagct tgtccgatct    21840
aggcgctgcg gccccgcggt cagatgctag tagcccattt ccaagcttga tagggtctct    21900
taccagcact cgcaccaccc gcccgcgcct gctgggcgag gaggagtacc taaacaactc    21960
gctgctgcag ccgcagcgcg aaaaaaacct gcctccggca tttcccaaca acgggataga    22020
gagcctagtg gacaagatga gtagatggaa gacgtacgcg caggagcaca gggacgtgcc    22080
aggcccgcgc ccgcccaccc gtcgtcaaag gcacgaccgt cagcggggtc tggtgtggga    22140
ggacgatgac tcggcagacg acagcagcgt cctggatttg ggagggagtg caacccgtt     22200 tgcgcacctt cgccccaggc tggggagaat gttttaaaaa aaaaaagca tgatgcaaaa     22260 taaaaaactc accaaggcca tggcaccgag cgttggtttt cttgtattcc ccttagtatg    22320
cggcgcgcgg cgatgtatga ggaaggtcct cctccctcct acgagagtgt ggtgagcgcg    22380
gcgccagtgg cggcggcgct gggttctccc ttcgatgctc ccctggaccc gccgtttgtg    22440
cctccgcggt acctgcggcc taccgggggg agaaacagca tccgttactc tgagttggca    22500
cccctattcg acaccacccg tgtgtacctg gtggacaaca agtcaacgga tgtggcatcc    22560
ctgaactacc agaacgacca cagcaacttt ctgaccacgg tcattcaaaa caatgactac    22620
agcccggggg aggcaagcac acagaccatc aatcttgacg accggtcgca ctgggcggc     22680 gacctgaaaa ccatcctgca taccaacatg ccaaatgtga acgagttcat gtttaccaat    22740
aagtttaagg cgcgggtgat ggtgtcgcgc ttgcctacta aggacaatca ggtggagctg    22800
aaatacgagt gggtggagtt cacgctgccc gagggcaact actccgagac catgaccata    22860
gaccttatga acaacgcgat cgtggagcac tacttgaaag tgggcagaca gaacgggtt     22920 ctggaaagcg acatcggggt aaagtttgac acccgcaact tcagactggg gtttgacccc    22980
gtcactggtc ttgtcatgcc tgggtatat acaaacgaag ccttccatcc agacatcatt     23040
ttgctgccag gatgcgggt  ggacttcacc cacagccgcc tgagcaactt gttgggcatc    23100
```

```
cgcaagcggc aacccttcca ggagggcttt aggatcacct acgatgatct ggagggtggt    23160
aacattcccg cactgttgga tgtggacgcc taccaggcga gcttgaaaga tgacaccgaa    23220
cagggcgggg gtggcgcagg cggcagcaac agcagtggca gcggcgcgga agagaactcc    23280
aacgcggcag ccgcggcaat gcagccggtg gaggacatga acgatcatgc cattcgcggc    23340
gacacctttg ccacacgggc tgaggagaag cgcgctgagg ccgaagcagc ggccgaagct    23400 gccgccccg ctgcgcaacc cgaggtcgag aagcctcaga agaaaccggt gatcaaaccc    23460
ctgacagagg acagcaagaa acgcagttac aacctaataa gcaatgacag caccttcacc    23520
cagtaccgca gctggtacct tgcatacaac tacggcgacc ctcagaccgg aatccgctca    23580
tggaccctgc tttgcactcc tgacgtaacc tgcggctcgg agcaggtcta ctggtcgttg    23640
ccagacatga tgcaagaccc cgtgaccttc cgctccacgc gccagatcag caactttccg    23700
gtggtgggcg ccgagctgtt gcccgtgcac tccaagagct tctacaacga ccaggccgtc    23760
tactcccaac tcatccgcca gtttacctct ctgacccacg tgttcaatcg ctttcccgag    23820
aaccagattt tggcgcgccc gccagccccc accatcacca ccgtcagtga aaacgttcct    23880
gctctcacag atcacgggac gctaccgctg cgcaacagca tcggaggagt ccagcgagtg    23940
accattactg acgccagacg ccgcacctgc ccctacgttt acaaggccct gggcatagtc    24000
tcgccgcgcg tcctatcgag ccgcactttt tgagcaagca tgtccatcct tatatcgccc    24060
agcaataaca caggctgggg cctgcgcttc caagcaaga tgtttggcgg ggccaagaag    24120
cgctccgacc aacacccagt gcgcgtgcgc gggcactacc gcgcgccctg gggcgcgcac    24180
aaacgcggcc gcactgggcg caccaccgtc gatgacgcca tcgacgcggt ggtggaggag    24240
gcgcgcaact acacgcccac gccgccacca gtgtccacag tggacgcggc cattcagacc    24300
gtggtgcgcg gagcccggcg ctatgctaaa atgaagagac ggcggaggcg cgtagcacgt    24360
cgccaccgcc gccgacccgg cactgccgcc caacgcgcgg cggcggccct gcttaaccgc    24420
gcacgtcgca ccgccgacg ggcggccatg cgggccgctc gaaggctggc cgcgggtatt    24480
gtcactgtgc cccccaggtc caggcgacga gcggccgccg cagcagccgc ggccattagt    24540
gctatgactc agggtcgcag gggcaacgtg tattgggtgc gcgactcggt tagcggcctg    24600
cgcgtgcccg tgcgcacccg cccccgcgc aactagattg caagaaaaaa ctacttagac    24660
tcgtactgtt gtatgtatcc agcggcggcg gcgcgcaacg aagctatgtc caagcgcaaa    24720
atcaaagaag agatgctcca ggtcatcgcg ccggagatct atggccccc gaagaaggaa    24780 gagcaggatt acaagcccg aaagctaaag cgggtcaaaa agaaaaagaa agatgatgat    24840
gatgaacttg acgacgaggt ggaactgctg cacgctaccg cgcccaggcg acgggtacag    24900
tggaaaggtc gacgcgtaaa acgtgttttg cgacccggca ccaccgtagt ctttacgccc    24960
ggtgagcgct ccacccgcac ctacaagcgc gtgtatgatg aggtgtacgg cgacgaggac    25020
ctgcttgagc aggccaacga gcgcctcggg gagtttgcct acggaaagcg gcataaggac    25080
atgctggcgt tgccgctgga cgagggcaac ccaacaccta gcctaaagcc cgtaacactg    25140
cagcaggtgc tgcccgcgct tgcaccgtcc gaagaaaagc gcggcctaaa gcgcgagtct    25200
ggtgacttgg cacccaccgt gcagctgatg gtacccaagc gccagcgact ggaagatgtc    25260
ttggaaaaaa tgaccgtgga acctgggctg gagcccgagg tccgcgtgcg gccaatcaag    25320
caggtggcgc gggactgggg cgtgcagacc gtggacgttc agatacccac taccagtagc    25380
accagtattg ccaccgccac agagggcatg gagacacaaa cgtccccggt tgcctcagcg    25440
gtggcggatg ccgcggtgca ggcggtcgct gcggccgcgt ccaagacctc tacggaggtg    25500
```

```
caaacggacc cgtggatgtt tcgcgtttca gcccccggc gcccgcgcgg ttcgaggaag    25560 tacgcgccg  ccagcgcgct actgcccgaa tatgccctac atccttccat tgcgcctacc    25620
cccggctatc gtggctacac ctaccgcccc agaagacgag caactacccg acgccgaacc    25680
accactggaa cccgccgccg ccgtcgccgt cgccagcccg tgctggcccc gatttccgtg    25740
cgcagggtgg ctcgcgaagg aggcaggacc ctggtgctgc aacagcgcg  ctaccacccc    25800 agcatcgttt aaaagccggt ctttgtggtt cttgcagata tggccctcac ctgccgcctc    25860
cgtttcccgg tgccgggatt ccgaggaaga atgcaccgta ggaggggcat ggccggccac    25920
ggcctgacgg gcggcatgcg tcgtgcgcac caccggcggc ggcgcgcgtc gcaccgtcgc    25980
atgcgcggcg gtatcctgcc cctccttatt ccactgatcg ccgcggcgat tggcgccgtg    26040
cccggaattg catccgtggc cttgcaggcg cagagacact gattaaaaac aagttgcatg    26100
tggaaaaatc aaaataaaaa gtctggactc tcacgctcgc ttggtcctgt aactattttg    26160
tagaatggaa gacatcaact ttgcgtctct ggccccgcga cacggctcgc gcccgttcat    26220
gggaaactgg caagatatcg gcaccagcaa tatgagcggt ggcgccttca gctggggctc    26280
gctgtgcagc ggcattaaaa atttcggttc caccgttaag aactatggca gcaaggcctg    26340
gaacagcagc acaggccaga tgctgaggga taagttgaaa gagcaaaatt ccaacaaaa     26400 ggtggtagat ggcctggcct ctggcattag cggggtggtg gacctggcca accaggcagt    26460
gcaaaataag attaacagta agcttgatcc ccgccctccc gtagaggagc ctccaccggc    26520
cgtggagaca gtgtctccag aggggcgtgg cgaaaagcgt ccgcgcccg  acagggaaga    26580 aactctggtg acgcaaatag acgagcctcc ctcgtacgag gaggcactaa agcaaggcct    26640
gcccaccacc cgtcccatcg cgcccatggc taccggagtg ctgggccagc acacaccgt     26700 aacgctggac ctgcctcccc ccgccgacac ccagcagaaa cctgtgctgc caggcccgac    26760
cgccgttgtt gtaacccgtc ctagccgcgc gtccctgcgc cgcgccgcca gcggtccgcg    26820
atcgttgcgg cccgtagcca gtggcaactg gcaaagcaca ctgaacagca tcgtgggtct    26880
gggggtgcaa tccctgaagc gccgacgatg cttctgaata gctaacgtgt cgtatgtgtg    26940
tcatgtatgc gtccatgtcg ccgccagagg agctgctgag ccgccgcgcg cccgctttcc    27000
aagatggcta ccccttcgat gatgccgcag tggtcttaca tgcacatctc gggccaggac    27060
gcctcggagt acctgagccc cgggctggtg cagtttgccc gcgccaccga gacgtacttc    27120
agcctgaata acaagtttag aaacccccacg gtggcgccta cgcacgacgt gaccacagac    27180
cggtcccagc gtttgacgct gcggttcatc cctgtggacc gtgaggatac tgcgtactcg    27240
tacaaggcgc ggttcacccct agctgtgggt gataaccgtg tgctggacat ggcttccacg    27300
tactttgaca tccgcggcgt gctggacagg ggccctactt ttaagcccta ctctggcact    27360
gcctacaacg ccctggctcc caagggtgcc ccaaatcctt gcgaatggga tgaagctgct    27420
actgctcttg aaataaaacct agaagaagag gacgatgaca acgaagacga agtagacgag    27480
caagctgagc agcaaaaaac tcacgtattt gggcaggcgc cttattctgg tataaatatt    27540
acaaaggagg gtattcaaat aggtgtcgaa ggtcaaacac ctaaatatgc cgataaaaca    27600
tttcaacctg aacctcaaat aggagaatct cagtggtacg aaactgaaat taatcatgca    27660
gctgggagag tccttaaaaa gactaccccca atgaaaccat gttacggttc atatgcaaaa    27720
cccacaaatg aaaatggagg gcaaggcatt cttgtaaagc aacaaatgg  aaagctagaa    27780 agtcaagtgg aaatgcaatt tttctcaact actgaggcga ccgcaggcaa tggtgataac    27840
```

```
ttgactccta aagtggtatt gtacagtgaa gatgtagata tagaaacccc agacactcat    27900
atttcttaca tgcccactat taaggaaggt aactcacgag aactaatggg ccaacaatct    27960
atgcccaaca ggcctaatta cattgctttt agggacaatt ttattggtct aatgtattac    28020
aacagcacgg gtaatatggg tgttctggcg ggccaagcat cgcagttgaa tgctgttgta    28080
gatttgcaag acagaaacac agagctttca taccagcttt tgcttgattc cattggtgat    28140
agaaccaggt acttttctat gtggaatcag gctgttgaca gctatgatcc agatgttaga    28200
attattgaaa atcatggaac tgaagatgaa cttccaaatt actgctttcc actgggaggt    28260
gtgattaata cagagactct taccaaggta aaacctaaaa caggtcagga aaatggatgg    28320
gaaaaagatg ctacagaatt ttcagataaa aatgaaataa gagttggaaa taattttgcc    28380
atggaaatca atctaaatgc caacctgtgg agaaatttcc tgtactccaa catagcgctg    28440
tatttgcccg acaagctaaa gtacagtcct tccaacgtaa aaatttctga taacccaaac    28500
acctacgact acatgaacaa gcgagtggtg gctcccgggt tagtggactg ctacattaac    28560
cttggagcac gctggtccct tgactatatg gacaacgtca cccatttaa ccaccaccgc    28620 aatgctggcc tgcgctaccg ctcaatgttg ctgggcaatg gtcgctatgt gcccttccac    28680
atccaggtgc ctcagaagtt ctttgccatt aaaaacctcc ttctcctgcc gggctcatac    28740
acctacgagt ggaacttcag gaaggatgtt aacatggttc tgcagagctc cctaggaaat    28800
gacctaaggg ttgacggagc cagcattaag tttgatagca tttgccttta cgccaccttc    28860
ttccccatgg cccacaacac cgcctccacg cttgaggcca tgcttagaaa cgacaccaac    28920
gaccagtcct ttaacgacta tctctccgcc gccaacatgc tctaccctat acccgccaac    28980
gctaccaacg tgcccatatc catcccctcc cgcaactggg cggctttccg cggctgggcc    29040
ttcacgcgcc ttaagactaa ggaaaccca tcactgggct cgggctacga cccttattac    29100
acctactctg gctctatacc ctacctagat ggaacctttt acctcaacca cacctttaag    29160
aaggtggcca ttacctttga ctcttctgtc agctggcctg gcaatgaccg cctgcttacc    29220
cccaacgagt ttgaaattaa gcgctcagtt gacggggagg gttacaacgt tgcccagtgt    29280
aacatgacca aagactggtt cctggtacaa atgctagcta actacaacat ggcctaccag    29340
ggcttctata tcccagagag ctacaaggac cgcatgtact ccttctttag aaacttccag    29400
cccatgagcc gtcaggtggt ggatgatact aaatacaagg actaccaaca ggtgggcatc    29460
ctacaccaac acaacaactc tggatttgtt ggctaccttg cccccaccat gcgcgaagga    29520
caggcctacc ctgctaactt cccctatccg cttataggca agaccgcagt tgacagcatt    29580
acccagaaaa agtttctttg cgatcgcacc ctttggcgca tcccattctc cagtaacttt    29640
atgtccatgg gcgcactcac agacctgggc caaaaccttc tctacgccaa ctccgcccac    29700
gcgctagaca tgactttga ggtggatccc atggacgagc ccaccttct ttatgttttg    29760 tttgaagtct ttgacgtggt ccgtgtgcac cggccgcacc gcggcgtcat cgaaaccgtg    29820
tacctgcgca cgcccttctc ggccggcaac gccacaacat aaagaagcaa gcaacatcaa    29880
caacagctgc cgccatgggc tccagtgagc aggaactgaa agccattgtc aaagatcttg    29940
gttgtgggcc atatttttg ggcacctatg acaagcgctt tccaggcttt gtttctccac    30000
acaagctcgc ctgcgccata gtcaatacgg ccggtcgcga gactggggc gtacactgga    30060 tggccttgc ctggaacccc cactcaaaaa catgctacct ctttgagccc tttggctttt    30120
ctgaccagcg actcaagcag gtttaccagt ttgagtacga gtcactcctg cgccgtagcc    30180
ccattgcttc ttcccccgac cgctgtataa cgctggaaaa gtccacccaa agcgtacagg    30240
```

```
ggcccaactc ggccgcctgt ggactattct gctgcatgtt tctccacgcc tttgccaact    30300
ggccccaaac tcccatggat cacaacccca ccatgaacct tattaccggg gtacccaact    30360
ccatgctcaa cagtccccag gtacagccca ccctgcgtcg caaccaggaa cagctctaca    30420
gcttcctgga gcgccactcg ccctacttcc gcagccacag tgcgcagatt aggagcgcca    30480 cttcttttg tcacttgaaa aacatgtaaa aataatgtac tagagacact ttcaataaag    30540
gcaaatgctt ttatttgtac actctcgggt gattatttac ccccaccctt gccgtctgcg    30600
ccgtttaaaa atcaaagggg ttctgccgcg catcgctatg cgccactggc agggacacgt    30660
tgcgatactg gtgtttagtg ctccacttaa actcaggcac aaccatccgc ggcagctcgg    30720
tgaagttttc actccacagg ctgcgcacca tcaccaacgc gtttagcagg tcgggcgccg    30780
atatcttgaa gtcgcagttg gggcctccgc cctgcgcgcg cgagttgcga tacacagggt    30840
tgcagcactg gaacactatc agcgccgggt ggtgcacgct ggccagcacg ctcttgtcgg    30900
agatcagatc cgcgtccagg tcctccgcgt tgctcagggc gaacggagtc aactttggta    30960
gctgccttcc caaaaagggc gcgtgcccag gctttgagtt gcactcgcac cgtagtggca    31020
tcaaaaggtg accgtgcccg gtctgggcgt taggatacag cgcctgcata aaagccttga    31080
tctgcttaaa agccacctga gcctttgcgc cttcagagaa gaacatgccg caagacttgc    31140
cggaaaactg attggccgga caggccgcgt cgtgcacgca gcaccttgcg tcggtgttgg    31200
agatctgcac cacatttcgg ccccaccggt tcttcacgat cttggccttg ctagactgct    31260
ccttcagcgc gcgctgcccg ttttcgctcg tcacatccat ttcaatcacg tgctccttat    31320
ttatcataat gcttccgtgt agacacttaa gctcgccttc gatctcagcg cagcggtgca    31380
gccacaacgc gcagcccgtg ggctcgtgat gcttgtaggt cacctctgca aacgactgca    31440
ggtacgcctg caggaatcgc cccatcatcg tcacaaaggt cttgttgctg gtgaaggtca    31500
gctgcaaccc gcggtgctcc tcgttcagcc aggtcttgca tacggccgcc agagcttcca    31560
cttggtcagg cagtagtttg aagttcgcct ttagatcgtt atccacgtgg tacttgtcca    31620
tcagcgcgcg cgcagcctcc atgcccttct cccacgcaga cacgatcggc acactcagcg    31680
ggttcatcac cgtaatttca ctttccgctt cgctgggctc ttcctcttcc tcttgcgtcc    31740
gcataccacg cgccactggg tcgtcttcat tcagccgccg cactgtgcgc ttacctcctt    31800
tgccatgctt gattagcacc ggtgggttgc tgaaacccac catttgtagc gccacatctt    31860
ctctttcttc ctcgctgtcc acgattacct ctggtgatgg cgggcgctcg ggcttgggag    31920
aagggcgctt cttttttcttc ttgggcgcaa tggccaaatc cgccgccgag gtcgatggcc    31980
gcgggctggg tgtgcgcggc accagcgcgt cttgtgatga gtcttcctcg tcctcggact    32040
cgatacgccg cctcatccgc ttttttgggg gcgcccgggg aggcggcggc gacgggacg    32100 gggacgacac gtcctccatg gttggggac gtcgcgccgc accgcgtccg cgctcggggg    32160
tggtttcgcg ctgctcctct tcccgactgg ccatttcctt ctcctatagg cagaaaaaga    32220
tcatggagtc agtcgagaag aaggacagcc taaccgcccc ctctgagttc gccaccaccg    32280
cctccaccga tgccgccaac gcgcctacca ccttccccgt cgaggcaccc ccgcttgagg    32340
aggaggaagt gattatcgag caggacccag gttttgtaag cgaagacgac gaggaccgct    32400
cagtaccaac agaggataaa aagcaagacc aggacaacgc agaggcaaac gaggaacaag    32460
tcgggcgggg ggacgaaagg catggcgact acctagatgt gggagacgac gtgctgttga    32520
agcatctgca gcgccagtgc gccattatct gcgacgcgtt gcaagagcgc agcgatgtgc    32580
```

```
ccctcgccat agcggatgtc agccttgcct acgaacgcca cctattctca ccgcgcgtac    32640
cccccaaacg ccaagaaaac ggcacatgcg agcccaaccc gcgcctcaac ttctaccccg    32700
tatttgccgt gccagaggtg cttgccacct atcacatctt tttccaaaac tgcaagatac    32760
ccctatcctg ccgtgccaac cgcagccgag cggacaagca gctggccttg cggcagggcg    32820
ctgtcatacc tgatatcgcc tcgctcaacg aagtgccaaa atctttgag ggtcttggac     32880 gcgacgagaa gcgcgcggca aacgctctgc aacaggaaaa cagcgaaaat gaaagtcact    32940
ctggagtgtt ggtggaactc gagggtgaca acgcgcgcct agccgtacta aaacgcagca    33000
tcgaggtcac ccactttgcc tacccggcac ttaacctacc ccccaaggtc atgagcacag    33060
tcatgagtga gctgatcgtg cgccgtgcgc agccctgga gagggatgca aatttgcaag     33120
aacaaacaga ggagggccta cccgcagttg gcgacgagca gctagcgcgc tggcttcaaa    33180
cgcgcgagcc tgccgacttg gaggagcgac gcaaactaat gatggccgca gtgctcgtta    33240
ccgtggagct tgagtgcatg cagcggttct ttgctgaccc ggagatgcag cgcaagctag    33300
aggaaacatt gcactacacc tttcgacagg gctacgtacg ccaggcctgc aagatctcca    33360
acgtggagct ctgcaacctg gtctcctacc ttggaatttt gcacgaaaac cgccttgggc    33420
aaaacgtgct tcattccacg ctcaagggcg aggcgcgccg cgactacgtc cgcgactgcg    33480
tttacttatt tctatgctac acctggcaga cggccatggg cgtttggcag cagtgcttgg    33540
aggagtgcaa cctcaaggag ctgcagaaac tgctaaagca aaacttgaag gacctatgga    33600
cggccttcaa cgagcgctcc gtggccgcgc acctggcgga catcattttc cccgaacgcc    33660
tgcttaaaac cctgcaacag ggtctgccag acttcaccag tcaaagcatg ttgcagaact    33720
ttaggaactt tatcctagag cgctcaggaa tcttgcccgc cacctgctgt gcacttccta    33780
gcgactttgt gccattaag taccgcgaat gccctccgcc gctttggggc cactgctacc     33840
ttctgcagct agccaactac cttgcctacc actctgacat aatggaagac gtgagcggtg    33900
acggtctact ggagtgtcac tgtcgctgca acctatgcac cccgcaccgc tcctggtttt    33960
gcaattcgca gctgcttaac gaaagtcaaa ttatcggtac ctttgagctg cagggtccct    34020
cgcctgacga aaagtccgcg gctccggggt tgaaactcac tccggggctg tggacgtcgg    34080
cttaccttcg caaatttgta cctgaggact accacgccca cgagattagg ttctacgaag    34140
accaatcccg cccgccaaat gcggagctta ccgcctgcgt cattacccag gccacattc     34200 ttggccaatt gcaagccatc aacaaagccc gccaagagtt tctgctacga aagggacggg    34260
gggtttactt ggaccccccag tccggcgagg agctcaaccc aatcccccg ccgccgcagc     34320 cctatcagca gcagccgcgg gcccttgctt cccaggatgg cacccaaaaa gaagctgcag    34380
ctgccgccgc cacccacgga cgaggaggaa tactgggaca gtcaggcaga ggaggttttg    34440
gacgaggagg aggaggacat gatggaagac tgggagagcc tagacgagga agcttccgag    34500
gtcgaagagg tgtcagacga aacaccgtca ccctcggtcg cattccctc gccggcgccc    34560 cagaaatcgg caaccggttc cagcatggct acaacctccg ctcctcaggc gccgccggca    34620
ctgcccgttc gccgacccaa ccgtagatgg acaccactg gaaccagggc cggtaagtcc     34680
aagcagccgc cgccgttagc ccaagagcaa caacagcgcc aaggctaccg ctcatggcgc    34740
gggcacaaga acgccatagt tgcttgcttg caagactgtg ggggcaacat ctccttcgcc    34800
cgccgctttc ttctctacca tcacggcgtg gccttccccc gtaacatcct gcattactac    34860
cgtcatctct acagcccata ctgcaccggc ggcagcggca cggcagcaa cagcagcggc     34920 cacacagaag caaaggcgac cggatagcaa gactctgaca aagcccaaga aatccacagc    34980
```

| | |
|---|---|
| ggcggcagca gcaggaggag gagcgctgcg tctggcgccc aacgaacccg tatcgacccg | 35040 |
| cgagcttaga aacaggattt ttcccactct gtatgctata tttcaacaga gcagggggcca | 35100 |
| agaacaagag ctgaaaataa aaaacaggtc tctgcgatcc ctcacccgca gctgcctgta | 35160 |
| tcacaaaagc gaagatcagc ttcggcgcac gctggaagac gcggaggctc tcttcagtaa | 35220 |
| atactgcgcg ctgactctta aggactagtt tcgcgccctt tctcaaattt aagcgcgaaa | 35280 |
| actacgtcat ctccagcggc cacacccggc gccagcacct gtcgtcagcg ccattatgag | 35340 |
| caaggaaatt cccacgccct acatgtggag ttaccagcca caaatgggac ttgcggctgg | 35400 |
| agctgcccaa gactactcaa cccgaataaa ctacatgagc gcgggacccc acatgatatc | 35460 |
| ccgggtcaac ggaatccgcg cccaccgaaa ccgaattctc ttggaacagg cggctattac | 35520 |
| caccacacct cgtaataacc ttaatccccg tagttggccc gctgccctgg tgtaccagga | 35580 |
| aagtcccgct cccaccactg tggtacttcc cagagacgcc caggccgaag ttcagatgac | 35640 |
| taactcaggg gcgcagcttg cgggcggctt tcgtcacagg gtgcggtcgc ccgggcaggg | 35700 |
| tataactcac ctgacaatca gagggcgagg tattcagctc aacgacgagt cggtgagctc | 35760 |
| ctcgcttggt ctccgtccgg acgggacatt tcagatcggc ggcgccggcc gtccttcatt | 35820 |
| cacgcctcgt caggcaatcc taactctgca gacctcgtcc tctgagccgc gctctggagg | 35880 |
| cattggaact ctgcaattta ttgaggagtt tgtgccatcg gtctacttta acccccttctc | 35940 |
| gggacctccc ggccactatc cggatcaatt tattcctaac tttgacgcgg taaaggactc | 36000 |
| ggcggacggc tacgactgaa tgttaagtgg agaggcagag caactgcgcc tgaaacacct | 36060 |
| ggtccactgt cgccgccaca agtgctttgc ccgcgactcc ggtgagtttt gctactttga | 36120 |
| attgcccgag gatcatatcg agggcccggc gcacggcgtc cggcttaccg cccagggaga | 36180 |
| gcttgcccgt agcctgattc gggagtttac ccagcgcccc ctgctagttg agcgggacag | 36240 |
| gggaccctgt gttctcactg tgatttgcaa ctgtcctaac cttggattac atcaagatcc | 36300 |
| tctagttata actagagtac ccggggatct tattccctt aactaataaa aaaaaataat | 36360 |
| aaagcatcac ttacttaaaa tcagttagca aatttctgtc cagtttattc agcagccct | 36420 |
| ccttgccctc ctcccagctc tggtattgca gcttcctcct ggctgcaaac tttctccaca | 36480 |
| atctaaatgg aatgtcagtt tcctcctgtt cctgtccatc cgcacccact atcttcatgt | 36540 |
| tgttgcagat gaagcgcgca agaccgtctg aagataccttt caaccccgtg tatccatatg | 36600 |
| acacggaaac cggtcctcca actgtgcctt ttcttactcc tcccttgta tcccccaatg | 36660 |
| ggtttcaaga gagtccccct ggggtactct ctttgcgcct atccgaacct ctagttacct | 36720 |
| ccaatggcat gcttgcgctc aaaatgggca acggcctctc tctggacgag gccggcaacc | 36780 |
| ttacctccca aaatgtaacc actgtgagcc cacctctcaa aaaaaccaag tcaaacataa | 36840 |
| acctggaaat atctgcaccc ctcacagtta cctcagaagc cctaactgtg gctgccgccg | 36900 |
| cacctctaat ggtcgcgggc aacacactca ccatgcaatc acaggcccccg ctaaccgtgc | 36960 |
| acgactccaa acttagcatt gccacccaag gacccctcac agtgtcagaa ggaaagctag | 37020 |
| ccctgcaaac atcaggcccc ctcaccacca ccgatagcag taccctttact atcactgcct | 37080 |
| cacccctctct aactactgcc actggtagct gggcattga cttgaaagag ccattttata | 37140 |
| cacaaaatgg aaaactagga ctaaagtacg gggctccttt gcatgtaaca gacgacctaa | 37200 |
| acactttgac cgtagcaact ggtccaggtg tgactattaa taatacttcc ttgcaaacta | 37260 |
| aagttactgg agccttgggt tttgattcac aaggcaatat gcaacttaat gtagcaggag | 37320 |

```
gactaaggat tgattctcaa aacagacgcc ttatacttga tgttagttat ccgtttgatg    37380
ctcaaaacca actaaatcta agactaggac agggccctct tttttataaac tcagcccaca    37440 acttggatat taactacaac aaaggccttt acttgtttac agcttcaaac aattccaaaa    37500
agcttgaggt taacctaagc actgccaagg ggttgatgtt tgacgctaca gccatagcca    37560
ttaatgcagg agatgggctt gaatttggtt cacctaatgc accaaacaca aatcccctca    37620
aaacaaaaat tggccatggc ctagaatttg attcaaacaa ggctatggtt cctaaactag    37680
gaactggcct tagttttgac agcacaggtg ccattacagt aggaaacaaa aataatgata    37740
agctaacttt gtggaccaca ccagctccat ctcctaactg tagactaaat gcagagaaag    37800
atgctaaact cactttggtc ttaacaaaat gtggcagtca atacttgct acagtttcag     37860 ttttggctgt taaaggcagt ttggctccaa tatctggaac agttcaaagt gctcatctta    37920
ttataagatt tgacgaaaat ggagtgctac taaacaattc cttcctggac ccagaatatt    37980
ggaactttag aaatggagat cttactgaag gcacagccta tacaaacgct gttggattta    38040
tgcctaacct atcagcttat ccaaaatctc acggtaaaac tgccaaaagt aacattgtca    38100
gtcaagttta cttaaacgga gacaaaacta aacctgtaac actaaccatt acactaaacg    38160
gtacacagga aacaggagac acaactccaa gtgcatactc tatgtcattt tcatgggact    38220
ggtctggcca caactacatt aatgaaatat ttgccacatc ctcttacact ttttcataca    38280
ttgcccaaga ataagaatc gtttgtgtta tgtttcaacg tgtttatttt tcaattgcag     38340
aaaatttcaa gtcattttc attcagtagt atagccccac caccacatag cttatacaga    38400
tcaccgtacc ttaatcaaac                                                38420
```

<210> SEQ ID NO 2
<211> LENGTH: 12741
<212> TYPE: DNA
<213> ORGANISM: Artificial Sequence
<220> FEATURE:
<223> OTHER INFORMATION: Synthetic polynucleotide

<400> SEQUENCE: 2

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
```

```
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgatt    1800
gggcccgaga tctcgcgcgc gaggcctgcc atgggcatgc ctgcaggtcg atgcgtggcc    1860
ggcctaggat ccatatggta ccggtaaatg gcccgcctgg ctgaccgccc aacgaccccc    1920
gcccattgac gtcaataatg acgtatgttc ccatagtaac gccaataggg actttccatt    1980
gacgtcaatg ggtggagtat ttacggtaaa ctgcccactt ggcagtacat caagtgtatc    2040
atatgccaag tacgcccct attgacgtca atgacggtaa atggcccgcc tggcattatg    2100
cccagtacat gaccttatgg gactttccta cttggcagta catctagtat tagtcatcgc    2160
tattaccatg gtgatgcggt tttggcagta catcaatggg cgtggatagc ggtttgactc    2220
acggggattt ccaagtctcc accccattga cgtcaatggg agtttgtttt ggcaccaaaa    2280
tcaacgggac tttccaaaat gtcgtaacaa ctccgcccca ttgacgcaaa tgggcggtag    2340
gcgtgtacgg tggaggtct atataagcag agctcgttta gtgaaccgtc agatcgcctg    2400
gagacgccat ccacgctgtt ttgacctcca tagaagacac cgggaccgat ccagcctccg    2460
cggccgggaa cggtgcattg gaacgcggat tccccgtgcc aagagtgacg taagtaccgc    2520
ctatagactc tataggcaca ccctttggc tcttatgcat gaattaatac gactcactat    2580
agggagacag actgttcctt tcctgggtct tttctgcagg ctagccccac catgccgcgc    2640 gctcccccgct gccgagccgt gcgctccctg ctgcgcagcc actaccgcga ggtgctgccg    2700
ctggccacgt tcgtgcggcg cctggggccc cagggctggc ggctggtgca gcgcggggac    2760
ccggcggctt tccgcgcgct ggtggcccag tgcctggtgt gcgtgccctg ggacgcacgg    2820
ccgccccccg ccgccccctc cttccgccag gtgtcctgcc tgaaggagct ggtggcccga    2880
gtgctgcaga ggctgtgcga gcgcggcgcg aagaacgtgc tggccttcgg cttcgcgctg    2940
ctggacgggg cccgcggggg ccccccgag gccttcacca ccagcgtgcg cagctacctg    3000
cccaacacgg tgaccgacgc actgcggggg agcggggcgt gggggctgct gttgcgccgc    3060
gtgggcgacg acgtgctggt tcacctgctg gcacgctgcg cgctctttgt gctggtggct    3120
cccagctgcg cctaccaggt gtgcgggccg ccgctgtacc agctcggcgc tgccactcag    3180
gcccggcccc cgccacacgc tagtggaccc cgaaggcgtc tgggatgcga acgggcctgg    3240
aaccatagcg tcagggaggc cggggtcccc ctgggcctgc cagccccggg tgcgaggagg    3300
```

```
cgcgggggca gtgccagccg aagtctgccg ttgcccaaga ggcccaggcg tggcgctgcc    3360
cctgagccgg agcggacgcc cgttgggcag gggtcctggg cccacccggg caggacgcgt    3420
ggaccgagtg accgtggttt ctgtgtggtg tcacctgcca gacccgccga agaagccacc    3480
tctttggagg gtgcgctctc tggcacgcgc cactcccacc catccgtggg ccgccagcac    3540
cacgcgggcc cccatccac atcgcggcca ccacgtccct gggacacgcc ttgtcccccg    3600
gtgtacgccg agaccaagca cttcctctac tcctcaggcg acaaggagca gctgcggccc    3660
tccttcctac tcagctctct gaggcccagc ctgactggcg ctcggaggct cgtggagacc    3720
atctttctgg gttccaggcc ctggatgcca gggactcccc gcaggttgcc ccgcctgccc    3780
cagcgctact ggcaaatgcg gcccctgttt ctggagctgc ttgggaacca cgcgcagtgc    3840
ccctacgggg tgctcctcaa gacgcactgc ccgctgcgag ctgcggtcac ccagcagcc    3900 ggtgtctgtg cccgggagaa gccccagggc tctgtggcgg ccccgagga ggaggacaca    3960 gaccccgtc gcctggtgca gctgctccgc cagcacagca gccccctggca ggtgtacggc    4020 ttcgtgcggg cctgcctgcg ccggctggtg ccccaggcc tctgggctc caggcacaac    4080 gaacgccgct tcctcaggaa caccaagaag ttcatctccc tggggaagca tgccaagctc    4140
tcgctgcaga agctgacgtg aagatgagc gtgcggggct cgcttggct cgcaggagc    4200 ccaggggttg gctgtgttcc ggccgcagag caccgtctgc gtgaggagat cctggccaag    4260
ttcctgcact ggctgatgag tgtgtacgtc gtcgagctgc tcaggtcttt cttttatgtc    4320
acggagacca cgtttcaaaa gaacaggctc tttttctacc ggaagagtgt ctggagcaag    4380
ttgcaaagca ttggaatcag acagcacttg aagagggtgc agctgcggga gctgtcggaa    4440
gcagaggtca ggcagcatcg ggaagccagg cccgccctgc tgacgtccag actccgcttc    4500
atccccaagc ctgacgggct gcggccgatt gtgaacatgg actacgtcgt gggagccaga    4560
acgttccgca gagaaaagag ggccgagcgt ctcacctcca gggtgaaggc actgttcagc    4620
gtgctcaact acgagcgggc gcggcgcccc ggcctcctgg gcgcctctgt gctgggcctg    4680
gacgatatcc acagggcctg gcgcaccttc gtgctgcgtg tgcgggccca ggacccgccg    4740
cctgagctgt actttgtcaa ggtggatgtg acgggcgcgt acgacaccat cccccaggac    4800
aggctcacgg aggtcatcgc cagcatcatc aaaccccaga acacgtactg cgtgcgtcgg    4860
tatgccgtgt tccagaaggc cgcccatggg cacgtccgca aggccttcaa gagccacgtc    4920
tctaccttga cagacctcca gccgtacatg cgacagttcg tggctcacct gcaggagacc    4980
agcccgctga gggatgccgt cgtcatcgag cagagctcct ccctgaatga ggccagcagt    5040
ggcctcttcg acgtcttcct acgcttcatg tgccaccacg ccgtgcgcat caggggcaag    5100
tcctacgtcc agtgccaggg gatcccgcag ggctccatcc tctccacgct gctctgcagc    5160
ctgtgctacg gcgacatgga gaacaagctg tttgcgggga ttcggcggga cgggctgctc    5220
ctgcgtttgg tggatgattt cttgttggtg acacctcacc tcacccacgc gaaaaccttc    5280
ctcaggaccc tggtccgagg tgtccctgag tatggctgcg tggtgaactt gcggaagaca    5340
gtggtgaact ccctgtaga agacgaggcc ctgggtggca cggcttttgt tcagatgccg    5400
gcccacggcc tattccctg gtgcggcctg ctgctggata cccggaccct ggaggtgcag    5460
agcgactact ccagctatgc ccggacctcc atcagagcca gtctcacctt caaccgcggc    5520
ttcaaggctg gaggaacat gcgtcgcaaa ctctttgggg tcttgcggct gaagtgtcac    5580
agcctgtttc tggatttgca ggtgaacagc ctccagacgg tgtgcaccaa catctacaag    5640
atcctcctgc tgcaggcgta caggtttcac gcatgtgtgc tgcagctccc atttcatcag    5700
```

```
caagtttgga agaaccccac attttccctg cgcgtcatct ctgacacggc ctccctctgc   5760
tactccatcc tgaaagccaa gaacgcaggg atgtcgctgg gggccaaggg cgccgccggc   5820
cctctgccct ccgaggccgt gcagtggctg tgccaccaag cattcctgct caagctgact   5880
cgacaccgtg tcacctacgt gccactcctg gggtcactca ggacagccca gacgcagctg   5940
agtcggaagc tcccggggac gacgctgact gccctggagg ccgcagccaa cccggcactg   6000
ccctcagact tcaagaccat cctggactga gtcgaaactc gaggatccgg ctgtggaatg   6060
tgtgtcagtt agggtgtgga aagtccccag ctccccagc aggcagaagt atgcaaagca   6120
tgcatctcaa ttagtcagca accaggtgtg gaaagtcccc aggctcccca gcaggcagaa   6180
gtatgcaaag catgcatctc aattagtcag caaccatagt cccgcccta actccgccca   6240
tcccgccct aactccgccc agttccgccc attctccgcc ccatggctga ctaatttttt   6300
ttatttatgc agaggccgag gccgcctcgg cctctgagct attccagaag tagtgaggag   6360
gcttttttgg aggcctgtcgg ccgccacgac cggtgccgcc accatcccct gacccacgcc   6420
cctgacccct cacaaggaga cgaccttcca tgaccgagta caagcccacg gtgcgcctcg   6480
ccacccgcga cgacgtcccc cgggccgtac gcaccctcgc cgccgcgttc gccgactacc   6540
ctgcaacacg ccatacagtg gaccctgacc gccacatcga gcgggtcacc gagctgcaag   6600
aactcttcct cacgcgcgtc gggctcgaca tcggcaaggt gtgggtcgcg gacgacggcg   6660
ccgcggtggc ggtctggacc acgccggaga cgtcgaagc gggggcggtg ttcgccgaga   6720
tcggcccgcg catggccgag ttgagcggtt cccggctggc cgcgcagcaa cagatggaag   6780
gcctcctggc gccgcaccgg cccaaggagc ccgcgtggtt cctggccacc gtcggcgtct   6840
cgcccgacca ccagggcaag ggtctgggca gcgccgtcgt gctccccgga gtggaggcgg   6900
ccgagcgcgc cggggtgccc gccttcctgg agacctccgc gccccgcaac ctccccttct   6960
acgagcggct cggcttcacc gtcaccgccg acgtcgaggt gccgaagga ccgcgcacct   7020
ggtgcatgac ccgcaagccc ggtgcctgac gcccgcccca cgacccgcag cgcccgaccg   7080
aaaggagcgc acgaccccat gcatcgataa aataaaagat tttatttagt ctccagaaaa   7140
agggggggaat gaaagacccc acctgtaggt ttggcaagct aggcctatta atattccgga   7200
gtatacgtag ccggctaacg ttaacaaccg gtacgatgca ttagttatta atagtaatca   7260
attacggggt cattagttca tagcccatat atggagttcc gcgttacata acttacggta   7320
aatggcccgc ctggctgacc gcccaacgac ccccgcccat tgacgtcaat aatgacgtat   7380
gttcccatag taacgccaat agggactttc cattgacgtc aatgggtgga gtatttacgg   7440
taaactgccc acttggcagt acatcaagtg tatcatatgc caagtacgcc ccctattgac   7500
gtcaatgacg gtaaatggcc cgcctggcat tatgcccagt acatgacctt atgggacttt   7560
cctacttggc agtacatcta cgtattagtc atcgctatta ccatggtgat gcggttttgg   7620
cagtacatca atgggcgtgg atagcggttt gactcacggg gatttccaag tctccacccc   7680
attgacgtca atgggagttt gttttggcac caaaatcaac gggactttcc aaaatgtcgt   7740
aacaactccg ccccattgac gcaaatgggc ggtaggcgtg tacggtggga ggtctatata   7800
agcagagctg gtttagtgaa ccgtcagatc cgctagcgct accggactca gatctcgagc   7860
tcaagcttcg aattctgcag tcgacccacc atggctcttt caaacaagtt tatcggagat   7920
gacatgaaaa tgacctacca tatggatggc tgtgtcaatg gcattactt taccgtcaaa   7980
ggtgaaggca gcgggaagcc atacgaaggg acgcagacct cgactttaa agtcaccatg   8040
```

```
gccaacggtg ggccccttgc attctccttt gacatactat ctacagtgtt catgtatgga    8100
aatcgatgct ttactgcgta tcctaccagt atgcccgact atttcaaaca agcatttcct    8160
gacggaatgt catatgaaag acttttacc tatgaagatg gaggagttgc tacagccagt    8220
tgggaaataa gccttaaagg caactgcttt gagcacaaat ccacgtttca tggagtgaac    8280
tttcctgctg atggacctgt gatggcgaag atgacaactg gttgggaccc atcttttgag    8340
aaaatgactg tctgcgatgg aatattgaag ggtgatgtca ccgcgttcct catgctgcaa    8400
ggaggtggca attacagatg ccaattccac acttcttaca agacaaaaaa accggtgacg    8460
atgccaccaa accatgcggt ggaacatcgc attgcgagga ccgaccttga caaaggtggc    8520
aacagtgttc agctgacgga gcacgctgtt gcacatataa cctctgttgt cccttttctag   8580
cggccgcgat aatcaacctc tggattacaa aatttgtgaa agattgactg gtattcttaa    8640
ctatgttgct cctttttacgc tatgtggata cgctgcttta atgcctttgt atcatgctat    8700
tgcttcccgt atggctttca ttttctcctc cttgtataaa tcctggttgc tgtctcttta    8760
tgaggagttg tggcccgttg tcaggcaacg tggcgtggtg tgcactgtgt ttgctgacgc    8820
aaccccact ggttggggca ttgccaccac ctgtcagctc ctttccggga ctttcgcttt    8880
ccccctcct attgccacgg cggaactcat cgccgcctgc cttgcccgct gctggacagg    8940
ggctcggctg ttgggcactg acaattccgt ggtgttgtcg gggaagctga cgtcctttcc    9000
atggctgctc gcctgtgttg ccacctggat tctgcgcggg acgtccttct gctacgtccc    9060
ttcggccctc aatccagcgg accttccttc ccgcggcctg ctgccggctc tgcggcctct    9120
tccgcgtctt cgccttcgcc ctcagacgag tcggatctcc ctttgggccg cctccccgca    9180
tcggacgcgt ggtacctttta agaccaatga cttacaaggc agctgtagat cttagccact    9240
ttttaaaaga aaagggggga ctggaagggc taattcactc ccaacgaaga caagatctgc    9300
tttttgcttg tactgggtct ctctggttag accagatctg agcctgggag ctctctggct    9360
aactagggaa cccactgctt aagcctcaat aaagcttgcc ttgagtgctt caagtagtgt    9420
gtgcccgtct gttgtgtgac tctggtaact agagatccct cagacccttt tagtcagtgt    9480
ggaaaatctc tagcagtagt agttcatgtc atcttattat tcagtattta aacttgcaa    9540
agaaatgaat atcagagagt gagaggaact tgtttattgc agcttataat ggttacaaat    9600
aaagcaatag catcacaaat ttcacaaata aagcattttt ttcactgcat tctagttgtg    9660
gtttgtccaa actcatcaat gtatcttatc atgtctggct ctagctatcc cgcccctaac    9720
tccgcccatc ccgcccctaa ctccgcccag ttccgcccat tctccgcccc atggctgact    9780
aattttttt atttatgcag aggccgaggc cgcctcggcc tctgagctat tccagaagta    9840
gtgaggaggc ttttttggag gcctaggac gtacccaatt cgccctatag tgagtcgtat    9900
tacgcgcgct cactggccgt cgttttacaa cgtcgtgact gggaaaaccc tggcgttacc    9960
caacttaatc gccttgcagc acatccccct ttcgccagct ggcgtaatag cgaagaggcc   10020
cgcaccgatc gcccttccca acagttgcgc agcctgaatg gcgaatggga cgcgccctgt   10080
agcggcgcat taagcgcggc gggtgtggtg gttacgcgca gcgtgaccgc tacacttgcc   10140
agcgccctag cgcccgctcc tttcgctttc ttcccttcct ttctcgccac gttcgccggc   10200
tttccccgtc aagctctaaa tcgggggctc cctttagggt tccgatttag tgctttacgg   10260
cacctcgacc ccaaaaaact tgattagggt gatggttcac gtagtgggcc atcgccctga   10320
tagacggttt ttcgcccttt gacgttggag tccacgttct ttaatagtgg actcttgttc   10380
caaactggaa caacactcaa ccctatctcg gtctattctt ttgatttata agggattttg   10440
```

```
ccgatttcgg cctattggtt aaaaaatgag ctgatttaac aaaaatttaa cgcgaatttt    10500
aacaaaatat taacgcttac aatttaggtg gcacttttcg gggaaatgtg cgcggaaccc    10560
ctatttgttt attttttctaa atacattcaa atatgtatcc gctcatgaga caataaccct    10620
gataaatgct tcaataatat tgaaaaagga agagtatgag tattcaacat ttccgtgtcg    10680
cccttattcc ctttttttgcg gcattttgcc ttcctgtttt tgctcaccca gaaacgctgg    10740
tgaaagtaaa agatgctgaa gatcagttgg gtgcacgagt gggttacatc gaactggatc    10800
tcaacagcgg taagatcctt gagagttttc gccccgaaga acgttttcca atgatgagca    10860
cttttaaagt tctgctatgt ggcgcggtat tatcccgtat tgacgccggg caagagcaac    10920
tcggtcgccg catacactat tctcagaatg acttggttga gtactcacca gtcacagaaa    10980
agcatcttac ggatggcatg acagtaagag aattatgcag tgctgccata accatgagtg    11040
ataacactgc ggccaactta cttctgacaa cgatcggagg accgaaggag ctaaccgctt    11100
ttttgcacaa catgggggat catgtaactc gccttgatcg ttgggaaccg gagctgaatg    11160
aagccatacc aaacgacgag cgtgacacca cgatgcctgt agcaatggca acaacgttgc    11220
gcaaactatt aactggcgaa ctacttactc tagcttcccg gcaacaatta atagactgga    11280
tggaggcgga taaagttgca ggaccacttc tgcgctcggc ccttccggct ggctggttta    11340
ttgctgataa atctggagcc ggtgagcgtg ggtctcgcgg tatcattgca gcactggggc    11400
cagatggtaa gccctcccgt atcgtagtta tctacacgac ggggagtcag gcaactatgg    11460
atgaacgaaa tagacagatc gctgagatag gtgcctcact gattaagcat tggtaactgt    11520
cagaccaagt ttactcatat atactttaga ttgatttaaa acttcatttt taatttaaaa    11580
ggatctaggt gaagatcctt tttgataatc tcatgaccaa aatcccttaa cgtgagtttt    11640
cgttccactg agcgtcagac cccgtagaaa agatcaaagg atcttcttga gatcctttttt    11700 ttctgcgcgt aatctgctgc ttgcaaacaa aaaaaccacc gctaccagcg gtggtttgtt    11760
tgccggatca agagctacca actctttttc cgaaggtaac tggcttcagc agagcgcaga    11820
taccaaatac tgttcttcta gtgtagccgt agttaggcca ccacttcaag aactctgtag    11880
caccgcctac atacctcgct ctgctaatcc tgttaccagt ggctgctgcc agtggcgata    11940
agtcgtgtct taccgggttg gactcaagac gatagttacc ggataaggcg cagcggtcgg    12000
gctgaacggg gggttcgtgc acacagccca gcttggagcg aacgacctac accgaactga    12060
gatacctaca gcgtgagcta tgagaaagcg ccacgcttcc cgaagggaga aaggcggaca    12120
ggtatccggt aagcggcagg gtcggaacag gagagcgcac gagggagctt ccagggggaa    12180
acgcctggta tctttatagt cctgtcgggt ttcgccacct ctgacttgag cgtcgatttt    12240
tgtgatgctc gtcagggggg cggagcctat ggaaaaacgc cagcaacgcg gcctttttac    12300
ggttcctggc cttttgctgg ccttttgctc acatgttctt tcctgcgtta tcccctgatt    12360
ctgtggataa ccgtattacc gcctttgagt gagctgatac cgctcgccgc agccgaacga    12420
ccgagcgcag cgagtcagtg agcgaggaag cggaagagcg cccaatacgc aaaccgcctc    12480
tccccgcgcg ttggccgatt cattaatgca gctggcacga caggtttccc gactggaaag    12540
cgggcagtga gcgcaacgca attaatgtga gttagctcac tcattaggca ccccaggctt    12600
tacactttat gcttccggct cgtatgttgt gtggaattgt gagcggataa caatttcaca    12660
caggaaacag ctatgaccat gattacgcca agcgcgcaat taaccctcac taaagggaac    12720
aaaagctgga gctgcaagct t                                              12741
```

<210> SEQ ID NO 3
<211> LENGTH: 11626
<212> TYPE: DNA
<213> ORGANISM: Artificial Sequence
<220> FEATURE:
<223> OTHER INFORMATION: Synthetic polynucleotide

<400> SEQUENCE: 3

| | | | | | |
|---|---|---|---|---|---|
| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | ccttttagtc | agtgtggaaa | atctctagca | gtggcgcccg | 420 |
| aacagggact | tgaaagcgaa | agggaaacca | gaggagctct | ctcgacgcag | gactcggctt | 480 |
| gctgaagcgc | gcacggcaag | aggcgagggg | cggcgactgg | tgagtacgcc | aaaaattttg | 540 |
| actagcggag | gctagaagga | gagagatggg | tgcgagagcg | tcagtattaa | gcggggggaga | 600 |
| attagatcgc | gatgggaaaa | aattcggtta | aggccagggg | gaaagaaaaa | atataaatta | 660 |
| aaacatatag | tatgggcaag | cagggagcta | gaacgattcg | cagttaatcc | tggcctgtta | 720 |
| gaaacatcag | aaggctgtag | acaaatactg | ggacagctac | aaccatccct | tcagacagga | 780 |
| tcagaagaac | ttagatcatt | atataataca | gtagcaaccc | tctattgtgt | gcatcaaagg | 840 |
| atagagataa | aagacaccaa | ggaagcttta | gacaagatag | aggaagagca | aaacaaaagt | 900 |
| aagaccaccg | cacagcaagc | ggccgctgat | cttcagacct | ggaggaggag | atatgaggga | 960 |
| caattggaga | agtgaattat | ataaatataa | agtagtaaaa | attgaaccat | taggagtagc | 1020 |
| acccaccaag | gcaaagagaa | gagtggtgca | gagagaaaaa | agagcagtgg | gaataggagc | 1080 |
| tttgttcctt | gggttcttgg | gagcagcagg | aagcactatg | ggcgcagcgt | caatgacgct | 1140 |
| gacggtacag | gccagacaat | tattgtctgg | tatagtgcag | cagcagaaca | atttgctgag | 1200 |
| ggctattgag | gcgcaacagc | atctgttgca | actcacagtc | tggggcatca | agcagctcca | 1260 |
| ggcaagaatc | ctggctgtgg | aaagatacct | aaaggatcaa | cagctcctgg | ggatttgggg | 1320 |
| ttgctctgga | aaactcattt | gcaccactgc | tgtgccttgg | aatgctagtt | ggagtaataa | 1380 |
| atctctggaa | cagatttgga | atcacacgac | ctggatggag | tgggacagag | aaattaacaa | 1440 |
| ttacacaagc | ttaatacact | ccttaattga | agaatcgcaa | aaccagcaag | aaaagaatga | 1500 |
| acaagaatta | ttggaattag | ataaatgggc | aagtttgtgg | aattggttta | acataacaaa | 1560 |
| ttggctgtgg | tatataaaat | tattcataat | gatagtagga | ggcttggtag | gtttaagaat | 1620 |
| agttttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggtatcgata | 1800 |
| ctagtaattt | ttctgcagaa | aacgtacccg | gggatcctct | aggatcccac | cgaaaggttg | 1860 |
| ctccttaaca | caggctaagg | accagcttct | tgggagaga | acagacgcag | gggcgggagg | 1920 |
| gaaaaaggga | gaggcagacg | tcacttccc | ttggcggctc | tggcagcaga | ttggtcggtt | 1980 |
| gagtggcaga | aaggcagacg | gggactgggc | aaggcactgt | cggtgacatc | acggacaggg | 2040 |
| cgacttctat | gtagatgagg | cagcgcagag | gctgctgctt | cgccacttgc | tgcttcgcca | 2100 |

```
cgaaggagtt cccgtgccct gggagcgggt tcaggaccgc ggatcggaag tgagaatccc    2160
agctgtgtgt cagggctgga aagggctcgg gagtgcgcgg ggcaagtgac cgtgtgtgta    2220
aagagtgagg cgtatgaggc tgtgtcgggg cagagcccga agatccgggt tgcggagggt    2280
gggcctggga ggggtggtgg ccattttttg tctaacccta actgagaagg gcgtaggcgc    2340
cgtgcttttg ctccccgcgc gctgtttttc tcgctgactt tcagcgggcg gaaaagcctc    2400
ggcctgccgc cttccaccgt tcattctaga gcaaacaaaa aatgtcagct gctggcccgt    2460
tcgcccctcc cggggacctg cggcgggtcg cctgcccagc ccccgaaccc cgcctggagg    2520
ccgcggtcgg cccggggctt ctccggaggc acccactgcc accgcgaaga gttgggctct    2580
gtcagccgcg ggtctctcgg gggcgagggc gaggttcagg cctttcaggc cgcaggaaga    2640
ggaacggagc gagtccccgc gcgcggcgcg attccctgag ctgtgggacg tgcacccagg    2700
actcggctca cacatgcagt tcgctttcct gttggtgggg ggaacgccga tcgtgcgcat    2760
ccgtcacccc tcgccggcaa tgggggcttg tgaaccccca aacctgactg actgggccag    2820
tgtgctgcaa attggcagga gacgtgaagg cacctccaaa gtcgactttc tggagtttca    2880
aaaacagacc gtacatgtcc gcggtcgcga cgtacctacc gggtagggga ggcgcttttc    2940
ccaaggcagt ctggagcatg cgctttagca gccccgctgg gcacttggcg ctacacaagt    3000
ggcctctggc ctcgcacaca ttccacatcc accggtaggc gccaaccggc tccgttcttt    3060
ggtggcccct tcgcgccacc ttctactcct cccctagtca ggaagttccc ccccgccccg    3120
cagctcgcgt cgtgcaggac gtgacaaatg gaagtagcac gtctcactag tctcgtgcag    3180
atggacagca ccgctgagca atggaagcgg gtaggccttt ggggcagcgg ccaatagcag    3240
ctttgctcct tcgctttctg ggctcagagg ctgggaaggg gtgggtccgg gggcgggctc    3300
aggggcgggc tcagggcgg ggcgggcgcc cgaagtcctc cggaggcccg gcattctgca    3360
cgcttcaaaa gcgcacgtct gccgcgctgt tctcctcttc ctcatctccg ggcctttcga    3420
ctctagacac gtgttgacaa ttaatcatcg gcatagtata tcggcatagt ataatacgac    3480
aaggtgagga actaaaccat ggccaagcct ttgtctcaag aagaatccac cctcattgaa    3540
agagcaacgg ctacaatcaa cagcatcccc atctctgaag actacagcgt cgccagcgca    3600
gctctctcta gcgacggccg catcttcact ggtgtcaatg tatatcattt tactggggga    3660
ccttgtgcag aactcgtggt gctgggcact gctgctgctg cggcagctgg caacctgact    3720
tgtatcgtcg cgatcggaaa tgagaacagg ggcatcttga gccctgcgg acggtgccga    3780 caggtgcttc tcgatctgca tcctgggatc aaagccatag tgaaggacag tgatggacag    3840
ccgacggcag ttgggattcg tgaattgctg ccctctggtt atgtgtggga gggctaagca    3900
caattcgagc tcggtacgcg tatcgatggc gccagctgca ggcggccgcc atatgcatcc    3960
taggcctatt aatattccgg agtatacgta gccggctaac gttaacaacc ggtacgatgc    4020
attagttatt aatagtaatc aattacgggg tcattagttc atagcccata tatggagttc    4080
cgcgttacat aacttacggt aaatggcccg cctggctgac cgcccaacga ccccgcccca    4140
ttgacgtcaa taatgacgta tgttcccata gtaacgccaa tagggacttt ccattgacgt    4200
caatgggtgg agtatttacg gtaaactgcc cacttggcag tacatcaagt gtatcatatg    4260
ccaagtacgc ccctattga cgtcaatgac ggtaaatggc ccgcctggca ttatgcccag    4320
tacatgacct tatgggactt tcctacttgg cagtacatct acgtattagt catcgctatt    4380
accatggtga tgcggttttg gcagtacatc aatgggcgtg gatagcggtt tgactcacgg    4440
```

```
ggatttccaa gtctccaccc cattgacgtc aatgggagtt tgttttggca ccaaaatcaa    4500
cgggactttc caaaatgtcg taacaactcc gccccattga cgcaaatggg cggtaggcgt    4560
gtacggtggg aggtctatat aagcagagct ggtttagtga accgtcagat ccgctagccc    4620
caccatgccg cgcgctcccc gctgccgagc cgtgcgctcc ctgctgcgca gccactaccg    4680
cgaggtgctg ccgctggcca cgttcgtgcg gcgcctgggg ccccagggct ggcggctggt    4740
gcagcgcggg gacccggcgg cttccgcgc gctggtggcc cagtgcctgg tgtgcgtgcc     4800
ctgggacgca cggccgcccc ccgccgcccc ctccttccgc caggtgtcct gcctgaagga    4860
gctggtggcc cgagtgctgc agaggctgtg cgagcgcggc gcgaagaacg tgctggcctt    4920
cggcttcgcg ctgctggacg gggcccgcgg gggcccccc gaggccttca ccaccagcgt     4980
gcgcagctac ctgcccaaca cggtgaccga cgcactgcgg gggagcgggg cgtgggggct    5040
gctgttgcgc cgcgtgggcg acgacgtgct ggttcacctg ctggcacgct gcgcgctctt    5100
tgtgctggtg gctcccagct gcgcctacca ggtgtgcggg ccgccgctgt accagctcgg    5160
cgctgccact caggcccggc ccccgccaca cgctagtgga ccccgaaggc gtctgggatg    5220
cgaacgggcc tggaaccata cgtcaggga ggccggggtc cccctgggcc tgccagcccc     5280
gggtgcgagg aggcgcgggg gcagtgccag ccgaagtctg ccgttgccca agaggcccag    5340
gcgtggcgct gccctgagc cggagcggac gcccgttggg cagggtcct gggcccaccc      5400 gggcaggacg cgtggaccga gtgaccgtgg tttctgtgtg gtgtcacctg ccagacccgc    5460
cgaagaagcc acctctttgg agggtgcgct ctctggcacg cgccactccc acccatccgt    5520
gggccgccag caccacgcgg gccccccatc cacatcgcgg ccaccacgtc cctgggacac    5580
gccttgtccc ccggtgtacg ccgagaccaa gcacttcctc tactcctcag gcgacaagga    5640
gcagctgcgg ccctccttcc tactcagctc tctgaggccc agcctgactg cgctcggag     5700 gctcgtggag accatctttc tgggttccag gccctggatg ccaggactc cccgcaggtt      5760 gccccgcctg ccccagcgct actggcaaat gcggcccctg tttctggagc tgcttgggaa    5820
ccacgcgcag tgcccctacg gggtgctcct caagacgcac tgcccgctgc gagctgcggt    5880 cacccccagca gccggtgtct gtgcccggga aagcccccag ggctctgtgg cggccccga     5940 ggaggaggac acagaccccc gtcgcctggt gcagctgctc cgccagcaca gcagcccctg    6000
gcaggtgtac ggcttcgtgc gggcctgcct gcgccggctg gtgcccccag gcctctgggg    6060
ctccaggcac aacgaacgcc gcttcctcag gaacaccaag aagttcatct ccctggggaa    6120
gcatgccaag ctctcgctgc aggagctgac gtggaagatg agcgtgcggg gctgcgcttg    6180
gctgcgcagg agcccagggg ttggctgtgt tccggccgca gagcaccgtc tgcgtgagga    6240
gatcctggcc aagttcctgc actggctgat gagtgtgtac gtcgtcgagc tgctcaggtc    6300 tttctttat gtcacggaga ccacgtttca aaagaacagg ctcttttct accggaagag      6360 tgtctggagc aagttgcaaa gcattggaat cagacagcac ttgaagaggg tgcagctgcg    6420
ggagctgtcg gaagcagagg tcaggcagca tcggaagcc aggcccgccc tgctgacgtc     6480
cagactccgc ttcatcccca agcctgacgg gctgcggccg attgtgaaca tggactacgt    6540
cgtgggagcc agaacgttcc gcagagaaaa gagggccgag cgtctcacct ccagggtgaa    6600
ggcactgttc agcgtgctca actacgagcg ggcgcggcgc cccggcctcc tgggcgcctc    6660
tgtgctgggc ctggacgata tccacagggc ctggcgcacc ttcgtgctgc gtgtgcgggc    6720
ccaggacccg ccgcctgagc tgtactttgt caaggtggat gtgacgggcg cgtacgacac    6780
catcccccag gacaggctca cggaggtcat cgccagcatc atcaaacccc agaacacgta    6840
```

```
ctgcgtgcgt cggtatgccg tggtccagaa ggccgcccat gggcacgtcc gcaaggcctt    6900
caagagccac gtctctacct tgacagacct ccagccgtac atgcgacagt tcgtggctca    6960
cctgcaggag accagcccgc tgagggatgc cgtcgtcatc gagcagagct cctccctgaa    7020
tgaggccagc agtggcctct tcgacgtctt cctacgcttc atgtgccacc acgccgtgcg    7080
catcaggggc aagtcctacg tccagtgcca ggggatcccg cagggctcca tcctctccac    7140
gctgctctgc agcctgtgct acggcgacat ggagaacaag ctgtttgcgg ggattcggcg    7200
ggacgggctg ctcctgcgtt tggtggatga tttcttgttg gtgacacctc acctcaccca    7260
cgcgaaaacc ttcctcagga ccctggtccg aggtgtccct gagtatggct gcgtggtgaa    7320
cttgcggaag acagtggtga acttccctgt agaagacgag gccctgggtg cacggctttt    7380
tgttcagatg ccggcccacg gcctattccc ctggtgcggc ctgctgctgg atacccggac    7440
cctggaggtg cagagcgact actccagcta tgcccggacc tccatcagag ccagtctcac    7500
cttcaaccgc ggcttcaagg ctgggaggaa catgcgtcgc aaactctttg ggtcttgcg    7560
gctgaagtgt cacagcctgt ttctggattt gcaggtgaac agcctccaga cggtgtgcac    7620
caacatctac aagatcctcc tgctgcaggc gtacaggttt cacgcatgtg tgctgcagct    7680
cccatttcat cagcaagttt ggaagaaccc cacattttc ctgcgcgtca tctctgacac    7740
ggcctccctc tgctactcca tcctgaaagc caagaacgca gggatgtcgc tgggggccaa    7800
gggcgccgcc ggccctctgc cctccgaggc cgtgcagtgg ctgtgccacc aagcattcct    7860
gctcaagctg actcgacacc gtgtcaccta cgtgccactc ctggggtcac tcaggacagc    7920
ccagacgcag ctgagtcgga agctcccggg gacgacgctg actgccctgg aggccgcagc    7980
caacccggca ctgccctcag acttcaagac catcctggac tgagtcgaaa ctcgcggccg    8040
catgcgtcga cgcgtatcga tgcatcttaa gtagatgtac ctttaagacc aatgacttac    8100
aaggcagctg tagatcttag ccactttta aaagaaaagg ggggactgga agggctaatt    8160
cactcccaac gaagacaaga tctgcttttt gcttgtactg ggtctctctg gttagaccag    8220
atctgagcct gggagctctc tggctaacta gggaacccac tgcttaagcc tcaataaagc    8280
ttgccttgag tgcttcaagt agtgtgtgcc cgtctgttgt gtgactctgg taactagaga    8340
tccctcagac ccttttagtc agtgtggaaa atctctagca gtagtagttc atgtcatctt    8400
attattcagt atttataact tgcaaagaaa tgaatatcag agagtgagag gaacttgttt    8460
attgcagctt ataatggtta caaataaagc aatagcatca caaatttcac aaataaagca    8520
tttttttcac tgcattctag ttgtggtttg tccaaactca tcaatgtatc ttatcatgtc    8580
tggctctagc tatcccgccc ctaactccgc ccatcccgcc ctaactcccg cccagttccg    8640
cccattctcc gccccatggc tgactaattt tttttattta tgcagaggcc gaggccgcct    8700
cggcctctga gctattccag aagtagtgag gaggcttttt tggaggccta gggacgtacc    8760
caattcgccc tatagtgagt cgtattacgc gcgctcactg gccgtcgttt tacaacgtcg    8820
tgactgggaa aaccctggcg ttacccaact taatcgcctt gcagcacatc cccctttcgc    8880
cagctggcgt aatagcgaag aggcccgcac cgatcgccct tcccaacagt tgcgcagcct    8940
gaatggcgaa tgggacgcgc cctgtagcgg cgcattaagc gcggcgggtg tggtggttac    9000
gcgcagcgtg accgctacac ttgccagcgc cctagcgccc gctcctttcg ctttcttccc    9060
ttcctttctc gccacgttcg ccggctttcc ccgtcaagct ctaaatcggg gctcccttt    9120
agggttccga tttagtgctt tacggcacct cgaccccaaa aaacttgatt agggtgatgg    9180
```

```
ttcacgtagt gggccatcgc cctgatagac ggttttttcgc cctttgacgt tggagtccac    9240
gttctttaat agtggactct tgttccaaac tggaacaaca ctcaacccta tctcggtcta    9300
ttcttttgat ttataaggga ttttgccgat ttcggcctat tggttaaaaa atgagctgat    9360
ttaacaaaaa tttaacgcga attttaacaa aatattaacg cttacaattt aggtggcact    9420
tttcggggaa atgtgcgcgg aacccctatt tgtttatttt tctaaataca ttcaaatatg    9480
tatccgctca tgagacaata accctgataa atgcttcaat aatattgaaa aaggaagagt    9540
atgagtattc aacatttccg tgtcgccctt attccctttt ttgcggcatt ttgccttcct    9600 gttttttgctc acccagaaac gctggtgaaa gtaaaagatg ctgaagatca gttgggtgca    9660
cgagtgggtt acatcgaact ggatctcaac agcggtaaga tccttgagag ttttcgcccc    9720
gaagaacgtt ttccaatgat gagcactttt aaagttctgc tatgtggcgc ggtattatcc    9780
cgtattgacg ccgggcaaga gcaactcggt cgccgcatac actattctca gaatgacttg    9840
gttgagtact caccagtcac agaaaagcat cttacggatg gcatgacagt aagagaatta    9900
tgcagtgctg ccataaccat gagtgataac actgcggcca acttacttct gacaacgatc    9960
ggaggaccga aggagctaac cgcttttttg cacaacatgg gggatcatgt aactcgcctt   10020
gatcgttggg aaccggagct gaatgaagcc ataccaaacg acgagcgtga ccacacgatg   10080
cctgtagcaa tggcaacaac gttgcgcaaa ctattaactg gcgaactact tactctagct   10140
tcccggcaac aattaataga ctggatggag gcggataaag ttgcaggacc acttctgcgc   10200
tcggcccttc cggctggctg gtttattgct gataaatctg gagccggtga gcgtgggtct   10260
cgcggtatca ttgcagcact ggggccagat ggtaagccct cccgtatcgt agttatctac   10320
acgacgggga gtcaggcaac tatggatgaa cgaaatagac agatcgctga gataggtgcc   10380
tcactgatta agcattggta actgtcagac caagtttact catatatact ttagattgat   10440
ttaaaacttc atttttaatt taaaaggatc taggtgaaga tcctttttga atctcatg    10500 accaaaatcc cttaacgtga gttttcgttc cactgagcgt cagacccgt agaaaagatc    10560 aaaggatctt cttgagatcc tttttttctg cgcgtaatct gctgcttgca acaaaaaaa    10620 ccaccgctac cagcggtggt ttgtttgccg gatcaagagc taccaactct ttttccgaag   10680
gtaactggct tcagcagagc gcagatacca aatactgttc ttctagtgta gccgtagtta   10740
ggccaccact tcaagaactc tgtagcaccg cctacatacc tcgctctgct aatcctgtta   10800
ccagtggctg ctgccagtgg cgataagtcg tgtcttaccg ggttggactc aagacgatag   10860
ttaccggata aggcgcagcg tcgggctga acggggggtt cgtgcacaca gcccagcttg   10920
gagcgaacga cctacaccga actgagatac ctacagcgtg agctatgaga aagcgccacg   10980
cttcccgaag ggagaaaggc ggacaggtat ccggtaagcg gcagggtcgg aacaggagag   11040
cgcacgaggg agcttccagg gggaaacgcc tggtatcttt atagtcctgt cgggtttcgc   11100
cacctctgac ttgagcgtcg attttttgtga tgctcgtcag ggggcggag cctatggaaa   11160 aacgccagca acgcggcctt tttacggttc ctggccttt gctggccttt tgctcacatg   11220
ttctttcctg cgttatcccc tgattctgtg gataaccgta ttaccgcctt tgagtgagct   11280
gataccgctc gccgcagccg aacgaccgag cgcagcgagt cagtgagcga ggaagcgaa   11340 gagcgcccaa tacgcaaacc gcctctcccc gcgcgttggc cgattcatta atgcagctgg   11400
```

-continued

```
cacgacaggt ttcccgactg gaaagcgggc agtgagcgca acgcaattaa tgtgagttag    11460
ctcactcatt aggcacccca ggctttacac tttatgcttc cggctcgtat gttgtgtgga    11520
attgtgagcg gataacaatt tcacacagga aacagctatg accatgatta cgccaagcgc    11580
gcaattaacc ctcactaaag ggaacaaaag ctggagctgc aagctt                   11626
```